US012734160B2

(12) United States Patent
Crawford et al.

(10) Patent No.: US 12,734,160 B2
(45) Date of Patent: Sep. 15, 2026

(54) METHODS FOR TREATING SYMPTOMS AND DISORDERS ASSOCIATED WITH LYSOSOMAL STORAGE DISEASES

(71) Applicant: GENZYME CORPORATION, Cambridge, MA (US)

(72) Inventors: Nigel Patrick Somerville Crawford, Califon, NJ (US); Tanya Zaremba Fischer, Newton, MA (US)

(73) Assignee: Genzyme Corporation, Cambridge, MA (US)

( * ) Notice: Subject to any disclaimer, the term of this patent is extended or adjusted under 35 U.S.C. 154(b) by 953 days.

(21) Appl. No.: 17/428,504

(22) PCT Filed: Feb. 3, 2020

(86) PCT No.: PCT/US2020/016440
§ 371 (c)(1),
(2) Date: Aug. 4, 2021

(87) PCT Pub. No.: WO2020/163244
PCT Pub. Date: Aug. 13, 2020

(65) Prior Publication Data

US 2022/0023273 A1 Jan. 27, 2022

Related U.S. Application Data

(60) Provisional application No. 62/962,647, filed on Jan. 17, 2020, provisional application No. 62/937,618, filed on Nov. 19, 2019, provisional application No. 62/894,167, filed on Aug. 30, 2019, provisional application No. 62/851,433, filed on May 22, 2019, provisional application No. 62/800,996, filed on Feb. 4, 2019.

(51) Int. Cl.

| | |
|---|---|
| ***A61K 31/439*** | (2006.01) |
| ***A61K 38/47*** | (2006.01) |
| ***A61P 3/00*** | (2006.01) |
| ***A61P 17/00*** | (2006.01) |
| ***A61P 25/02*** | (2006.01) |

(52) U.S. Cl.
CPC ............ *A61K 31/439* (2013.01); *A61K 38/47* (2013.01); *A61P 3/00* (2018.01); *A61P 17/00* (2018.01); *A61P 25/02* (2018.01); *C12Y 302/01045* (2013.01)

(58) Field of Classification Search
None
See application file for complete search history.

(56) References Cited

U.S. PATENT DOCUMENTS

| | | | |
|---|---|---|---|
| 3,119,742 | A | 1/1964 | Heimlich et al. |
| 3,492,397 | A | 1/1970 | Peters et al. |
| 3,538,214 | A | 11/1970 | Polli et al. |
| 3,749,787 | A | 7/1973 | Hepworth et al. |
| 4,060,598 | A | 11/1977 | Groppenbacher et al. |
| 4,173,626 | A | 11/1979 | Dempski et al. |
| 4,593,034 | A | 6/1986 | Munson et al. |
| 4,683,195 | A | 7/1987 | Mullis et al. |
| 4,983,600 | A | 1/1991 | Ward et al. |
| 5,025,022 | A | 6/1991 | Naylor et al. |
| 5,106,851 | A | 4/1992 | Turconi et al. |
| 5,236,838 | A | 8/1993 | Rasmussen et al. |
| 5,242,929 | A | 9/1993 | Varasi et al. |
| 5,272,071 | A | 12/1993 | Chappel |
| 5,330,990 | A | 7/1994 | Hansen |
| 5,549,892 | A | 8/1996 | Friedman et al. |
| 5,668,144 | A | 9/1997 | Sabb et al. |
| 5,968,502 | A | 10/1999 | Treco et al. |
| 5,998,429 | A | 12/1999 | Macor et al. |
| 6,066,626 | A | 5/2000 | Yew et al. |
| 6,124,354 | A | 9/2000 | Aakerblom et al. |
| 6,468,998 | B1 | 10/2002 | Kuroita et al. |
| 6,492,386 | B2 | 12/2002 | Myers et al. |
| 6,599,916 | B2 | 7/2003 | Myers et al. |
| 6,780,861 | B2 | 8/2004 | Nozulak et al. |
| 6,916,828 | B2 | 7/2005 | Farrerons et al. |
| 6,953,855 | B2 | 10/2005 | Mazurov et al. |

(Continued)

FOREIGN PATENT DOCUMENTS

| | | |
|---|---|---|
| AU | 15909/95 A | 8/1995 |
| CA | 2066696 A1 | 3/1991 |

(Continued)

OTHER PUBLICATIONS

Politei, et al., (2016), Pain in Fabry Disease: Practical Recommendations for Diagnosis and Treatment. CNS Neurosci Ther, 22: 568-576 (Year: 2016).*

(Continued)

*Primary Examiner* — Jeffrey S Lundgren
*Assistant Examiner* — Anthony Joseph Seitz
(74) *Attorney, Agent, or Firm* — MORRISON & FOERSTER LLP

(57) ABSTRACT

This disclosure to methods for treating or preventing particular symptoms and disorders which are associated with lysosomal storage diseases using quinuclidine compounds of formula (I), optionally in combination with enzyme replacement therapy. This includes pain, such as abdominal pain, and dermatological disorders, such as angiokeratoma, in a patient having a disease such as Fabry disease. Also disclosed is a pharmaceutical composition comprising a quinuclidine compound for use in said methods.

19 Claims, No Drawings

(56) References Cited

U.S. PATENT DOCUMENTS

| | | | |
|---|---|---|---|
| 6,987,106 | B1 | 1/2006 | Gallet et al. |
| 7,091,227 | B2 | 8/2006 | Scott |
| 7,115,629 | B2 | 10/2006 | Gallemi et al. |
| 7,138,410 | B2 | 11/2006 | Luithle et al. |
| 7,273,872 | B2 | 9/2007 | Tracey et al. |
| 7,332,524 | B2 | 2/2008 | Linders et al. |
| 7,435,742 | B2 | 10/2008 | Prat Quinones et al. |
| 7,776,879 | B2 | 8/2010 | Buil Albero et al. |
| 7,840,109 | B2 | 11/2010 | Lu et al. |
| 7,985,760 | B2 | 7/2011 | Ali et al. |
| 8,003,617 | B2 | 8/2011 | Cheng et al. |
| 8,039,483 | B2 | 10/2011 | Amari et al. |
| 8,178,551 | B2 | 5/2012 | Lee et al. |
| 8,252,789 | B2 | 8/2012 | Lingwood et al. |
| 8,349,319 | B2 | 1/2013 | Schuchman et al. |
| 8,367,696 | B2 | 2/2013 | Nagashima et al. |
| 8,389,517 | B2 | 3/2013 | Ibraghimov-beskrovnaya et al. |
| 8,729,075 | B2 | 5/2014 | Ibraghimov Beskrovnaya et al. |
| 8,791,123 | B2 | 7/2014 | Allen et al. |
| 8,993,556 | B2 | 3/2015 | Brasca et al. |
| 9,108,975 | B2 | 8/2015 | Tamura et al. |
| 9,126,993 | B2 | 9/2015 | Bourque et al. |
| 9,139,580 | B2 | 9/2015 | Bourque et al. |
| 9,440,976 | B2 | 9/2016 | Dyke et al. |
| 9,481,671 | B2 | 11/2016 | Ibraghimov Beskrovnaya et al. |
| 9,518,049 | B2 | 12/2016 | Siegel et al. |
| 9,655,946 | B2 | 5/2017 | Alexiou et al. |
| 9,682,975 | B2 | 6/2017 | Siegel et al. |
| 9,845,327 | B2 | 12/2017 | Krainc et al. |
| 10,065,949 | B2 | 9/2018 | Siegel et al. |
| 10,604,518 | B2 | 3/2020 | Siegel et al. |
| 10,954,230 | B2 | 3/2021 | Siegel et al. |
| 11,008,316 | B2 | 5/2021 | Bourque et al. |
| 11,065,238 | B2 | 7/2021 | Darios et al. |
| 11,116,755 | B2 | 9/2021 | Moreno et al. |
| 11,857,512 | B2 | 1/2024 | Jeanjean et al. |
| 12,060,349 | B2 | 8/2024 | Bourque et al. |
| 12,083,115 | B2 | 9/2024 | Crawford et al. |
| 2002/0177591 | A1 | 11/2002 | Odonnell et al. |
| 2004/0002513 | A1 | 1/2004 | Mazurov et al. |
| 2005/0031683 | A1 | 2/2005 | Kapoor et al. |
| 2005/0239774 | A1 | 10/2005 | Ernst et al. |
| 2006/0058349 | A1 | 3/2006 | Ali et al. |
| 2007/0213350 | A1 | 9/2007 | Tracey et al. |
| 2007/0249588 | A1 | 10/2007 | Ernst et al. |
| 2008/0234324 | A1 | 9/2008 | Orchard et al. |
| 2009/0017847 | A1 | 1/2009 | Mendiola et al. |
| 2009/0131470 | A1 | 5/2009 | Walmsley et al. |
| 2009/0163500 | A1 | 6/2009 | Lingwood et al. |
| 2009/0163545 | A1 | 6/2009 | Goldfarb |
| 2009/0170847 | A1 | 7/2009 | Lee et al. |
| 2009/0318491 | A1 | 12/2009 | Picciotto et al. |
| 2010/0113517 | A1 | 5/2010 | Palling |
| 2010/0190761 | A1 | 7/2010 | Ogawa et al. |
| 2011/0052559 | A1 | 3/2011 | Schuchman et al. |
| 2012/0157464 | A1 | 6/2012 | Feurbach et al. |
| 2014/0228575 | A1 | 8/2014 | Bessa Bellunt et al. |
| 2014/0255381 | A1 | 9/2014 | Bourque et al. |
| 2014/0371460 | A1 | 12/2014 | Bourque et al. |
| 2015/0210681 | A1 | 7/2015 | Bourque et al. |
| 2016/0039805 | A1 | 2/2016 | Siegel et al. |
| 2016/0039806 | A1 | 2/2016 | Siegel et al. |
| 2016/0207933 | A1 | 7/2016 | Bourque et al. |
| 2016/0361301 | A1 | 12/2016 | Leonard et al. |
| 2017/0258828 | A1 | 9/2017 | Liu et al. |
| 2017/0334903 | A1 | 11/2017 | Siegel et al. |
| 2018/0036295 | A1* | 2/2018 | Cheng .................... A61P 25/28 |
| 2018/0065957 | A1 | 3/2018 | Bourque et al. |
| 2019/0015380 | A1 | 1/2019 | Sun et al. |
| 2019/0030082 | A1 | 1/2019 | Bae et al. |
| 2019/0031652 | A1 | 1/2019 | Siegel et al. |
| 2019/0248790 | A1 | 8/2019 | Li et al. |
| 2020/0048266 | A1 | 2/2020 | Bourque et al. |
| 2020/0124624 | A1 | 4/2020 | Sardi et al. |
| 2020/0181137 | A1 | 6/2020 | Siegel et al. |
| 2020/0197374 | A1 | 6/2020 | Cheng et al. |
| 2020/0222310 | A1 | 7/2020 | Purohit et al. |
| 2021/0251982 | A1 | 8/2021 | Crawford et al. |
| 2021/0261557 | A1 | 8/2021 | Bourque et al. |
| 2022/0016092 | A1 | 1/2022 | Crawford et al. |
| 2022/0023272 | A1 | 1/2022 | Jeanjean et al. |
| 2022/0073508 | A1 | 3/2022 | Bourque et al. |
| 2022/0110922 | A1 | 4/2022 | Ibraghimov-Beskrovnaya et al. |
| 2022/0193059 | A1 | 6/2022 | Hayden et al. |
| 2022/0409595 | A1 | 12/2022 | Leonard et al. |
| 2023/0372313 | A1 | 11/2023 | Fischer et al. |
| 2024/0091208 | A1 | 3/2024 | Jeanjean et al. |
| 2025/0026749 | A1 | 1/2025 | Bourque et al. |

FOREIGN PATENT DOCUMENTS

| | | | |
|---|---|---|---|
| CA | 2182568 | A1 | 8/1995 |
| CA | 2398754 | A1 | 8/2001 |
| DE | 1326510 | U | 6/1958 |
| DE | 1768808 | U | 6/1958 |
| DE | 4326510 | A1 | 2/1995 |
| EP | 0382687 | A2 | 8/1990 |
| EP | 0505778 | A1 | 9/1992 |
| EP | 0747355 | A1 | 12/1996 |
| EP | 1231212 | A1 | 8/2002 |
| EP | 1300407 | A1 | 4/2003 |
| EP | 2119716 | A1 | 11/2009 |
| EP | 2154136 | A1 | 2/2010 |
| EP | 2895484 | A1 | 7/2015 |
| GB | 725228 | A | 3/1955 |
| JP | H08198751 | A | 8/1996 |
| JP | 2002302490 | A | 10/2002 |
| JP | 2003267977 | | 9/2003 |
| JP | 2014-517808 | A | 7/2014 |
| RU | 2296762 | C2 | 4/2007 |
| RU | 2430089 | C2 | 9/2011 |
| RU | 2436782 | C1 | 12/2011 |
| WO | 1995/021820 | | 8/1995 |
| WO | 199717348 | A1 | 5/1997 |
| WO | 97/30998 | A1 | 8/1997 |
| WO | 199804517 | A1 | 2/1998 |
| WO | 00/06186 | A1 | 2/2000 |
| WO | 200026186 | A1 | 5/2000 |
| WO | 00/58311 | A1 | 10/2000 |
| WO | 00/58313 | A1 | 10/2000 |
| WO | 01/85727 | A1 | 11/2001 |
| WO | 02/05662 | A1 | 1/2002 |
| WO | 02/15662 | A2 | 2/2002 |
| WO | 02/16356 | A2 | 2/2002 |
| WO | 2003078431 | A1 | 9/2003 |
| WO | 2004/000840 | A2 | 12/2003 |
| WO | 2004/007453 | A1 | 1/2004 |
| WO | 2004/016617 | A1 | 2/2004 |
| WO | 2004011430 | A1 | 2/2004 |
| WO | 2004/019947 | A1 | 3/2004 |
| WO | 2004/052365 | A2 | 6/2004 |
| WO | 2004/056745 | A2 | 7/2004 |
| WO | 2005/061510 | A1 | 7/2005 |
| WO | 2005/068426 | A1 | 7/2005 |
| WO | 2005073183 | A1 | 8/2005 |
| WO | WO 2005/073183 | | 8/2005 |
| WO | 2006/002375 | A2 | 1/2006 |
| WO | 2006/053043 | A2 | 5/2006 |
| WO | 2006/134318 | A1 | 12/2006 |
| WO | 2007038367 | A1 | 4/2007 |
| WO | WO 2007/038367 | | 4/2007 |
| WO | 2007/083978 | A1 | 7/2007 |
| WO | 2007/100430 | A2 | 9/2007 |
| WO | 2008/156721 | A1 | 12/2008 |
| WO | 2010/014455 | A2 | 2/2010 |
| WO | 2010/014554 | A1 | 2/2010 |
| WO | 2010/015324 | A1 | 2/2010 |
| WO | 2010/015816 | A2 | 2/2010 |
| WO | 2010091104 | A1 | 8/2010 |
| WO | 2010091164 | A1 | 8/2010 |
| WO | WO 2010/091104 | | 8/2010 |
| WO | WO 2010/091164 | | 8/2010 |
| WO | 2010/121963 | A1 | 10/2010 |
| WO | 2011/006074 | A1 | 1/2011 |

(56) References Cited

FOREIGN PATENT DOCUMENTS

| | | | | |
|---|---|---|---|---|
| WO | 2011/009890 | A2 | 1/2011 | |
| WO | 2011/073263 | A1 | 6/2011 | |
| WO | 2011/141483 | A2 | 11/2011 | |
| WO | 2012/063933 | A1 | 5/2012 | |
| WO | WO-2012129084 | A2 * | 9/2012 | .......... A61K 31/439 |
| WO | 2012/175119 | A1 | 12/2012 | |
| WO | 2012/177997 | A1 | 12/2012 | |
| WO | 2014/041425 | A1 | 3/2014 | |
| WO | 2014/043068 | A1 | 3/2014 | |
| WO | 2014/152215 | A1 | 9/2014 | |
| WO | 2016/145046 | A1 | 9/2016 | |
| WO | 2017087409 | A1 | 5/2017 | |
| WO | 2017/192841 | A1 | 11/2017 | |
| WO | 2020163244 | A1 | 8/2020 | |
| WO | 2020163245 | A1 | 8/2020 | |
| WO | 2020163337 | A1 | 8/2020 | |
| WO | WO 2020/163245 | | 8/2020 | |
| WO | WO 2020/163337 | | 8/2020 | |
| WO | 2021/061701 | A1 | 4/2021 | |
| WO | 2022/018695 | A1 | 1/2022 | |
| WO | 2025/219951 | A1 | 10/2025 | |
| WO | 2025/219952 | A1 | 10/2025 | |
| WO | 2025/262570 | A1 | 12/2025 | |

OTHER PUBLICATIONS

Hoffmann et al., Fabry disease—often seen, rarely diagnosed. Dtsch Arztebl Int. Jun. 2009;106(26):440-7 (Year: 2009).*

Buda et al., Gastrointestinal phenotype of fabry disease in a patient with pseudoobstruction syndrome. JIMD Rep. 2012;4:25-8 (Year: 2012).*

Nordbeck et al., Lucerastat, an oral therapy for Fabry disease: results from a pivotal randomized phase 3 study and its open-label extension. Nat Commun 17, 1534 (2026) (Year: 2026).*

Thurberg, B., et al., "Monitoring the 3-Year Efficacy of Enzyme Replacement Therapy in Fabry Disease by Repeated Skin Biopsies" The Journal of Investigative Dermatology, 2004, vol. 122, pp. 900-908.

Ashe et al, "Efficacy of Enzyme and Substrate Reduction Therapy with a Novel Antagonist of Glucosylceramide Synthase for Fabry Disease" Molecular Medicine, pp. 389-399, 2015.

Politei et al, "Pain in Fabry Disease: Practical Recommendations for Diagnosis and Treatment" Neuroscience & Therapeutics, pp. 568-576, 2016.

Sardi et al, "Glucosylceramide synthase inhibition alleviates aberrations in synucleinopathy models" PNAS, vol. 114, No. 10, pp. 2699-2704, 2017.

Auray-Blais C., et al., "How Well Does Urinary Lyso-gb3 Function as a Biomarker in Fabry Disease?," Clinica Chimica Acta, 2010, vol. 411 (23-24), pp. 1906-1914.

Bangari, et al., "Progressive Organ Pathology Resembles the Type 2 Later-Onset Phenotype of Fabry Disease," The American Journal of Pathology, 185(3):651-665 (2015).

Branco L., et al., "Selective Deletion of Antigen-Specific, Activated T Cells by a Humanized MAB to CO2 {Medi-507) s Mediated by NK Cells," Transplantation, 1999, vol. 68 (10), pp. 1588-1596.

Conradi, et al., Neuropathology of the Norrbottnian Type of Gaucher Disease, Acta Neuropathologica 65: 99-109 (1984).

Gaenslen, A., et al., "The Patient's Perception of Prodromal Symptoms Before the Initial Diagnosis of Parkinson's Disease," Movement Disorders: Official Journal of Movement Disorder Society, 26(4): 653-658, 656 (2011).

Gambarin, F., et al., "When Should Cardiologists Suspect Anderson-Fabry Disease?" The American Journal of Cardiology, 106(10): 1492-1499 (2010).

International Preliminary Report on Patentability for Application No. PCT/US2013/058896, mailed on Mar. 17, 2015, 9pages.

International Search Report and Written Opinion for Application No. PCT/US2013/058896, mailed on Nov. 18, J013, 15 pages.

Kodanko J.J., et al., "Synthesis of Diethynyltriptycene-linked Dipyridyl Ligands," Organic Letters, 2005, vol. 7 (21), pp. 4585-4588.

Kurlberg G., et al., "Blockade of the B7-CD28 Pathway by CTLA4-lg Counteracts Rejection and Prolongs Survival n Small Bowel Transplantation," Scandinavian Journal of Immunology, 2000, vol. 51 (3), pp. 224-230.

Lee, V., "Mechanisms of Parkinson's Disease Linked to Pathological α-Synuclein: New Targets for Drug Discovery," Elsevier Inc., Neuron 52:33-38 (2006).

Merrill et al., Sphingolipidomics: High-throughput, structure-speciWc, and quantitative analysis of sphingolipids by liquid chromatographytandem mass spectrometry, Methods 36: 207-224 (2005).

Naito, R., et al., "Selective Muscarinic Antagonists. II.(1) Synthesis and Antimuscarinic Properties of Biphenylylcarbamate Derivatives," Chem. Pharm. Bull., 1998, vol. 46(8), pp. 1286-1294.

Nilsson 0., et al., "Accumulation of Glucosylceramide and Glucosylsphingosine (Psychosine) in Cerebrum and Cerebellum in Infantile and Juvenile Gaucher Disease," Journal of Neurochemistry, 1982, vol. 39 (3), pp. 709-718.

Noelker, C., et al., "Glucocerebrosidase deficiency and mitochondrial impairment in experimental Parkinson disease," Journal of the Neurological Sciences, Elsevier, 356(1-2): 129-136 (2015).

Orvisky et al., Glucosylsphingosine accumulation in tissues from patients with Gaucher disease: correlation with phenotype and genotype, Molecular Genetics and Metabolism 76: 262-270 (2002).

Ross, C. & Poirier, M., "Protein aggregation and neurodegenerative disease," Nature Medicine 10, S10-S17, Abstract (2004).

Ryan E.A., et al., "Clinical Outcomes and Insulin Secretion after Islet Transplantation with the Edmonton Protocol,"Diabetes, 2001, vol. 50 (4), pp. 710-719.

Scholl, M., et al., "In Vivo Braak Staging Using 18F-AV1451 Tau PET Imaging," Alzheimer's & Dementia 11(7): Suppl. P4 (Jul. 2015).

Shen, W., et al., "Inhibition of glucosylceramide synthase stimulates autophagy flux in neurons," Journal of Neurochemistry, 129: 884-894 (2014).

Thurberg, et al., "Cardiac Microvascular Pathology in Fabry Disease Evaluation of Endomyocardial Biopsies Before and After Enzyme Replacement Therapy," Circulation, 119(19):2561-2567 (2009).

Urbanelli, L., et al., "Therapeutic Approaches for Lysosomal Storage Diseases: A Patent Update," Recent Patents on CNS Drug Discovery, 8(2): 1-19 (2013).

Wemheuer, W., et al., "Types and Strains: Their Essential Role in Understanding Protein Aggregation in Neurodegenerative Diseases," Frontiers in Aging Neuroscience, 9:187 (2017).

Firsov, et al., "The neurological manifestations of Fabry disease. A review" Journal of Neurology and Psychiatry, vol. 9, pp. 98-105, Sep. 2016 (English Language Translation of Russian).

"Tauopathy," Standardofcare.com, http://ps/standardofcare.com/tauopathy/ (2022).

Aerts, et al., "Elevated Globotriaosylsphingosine is a Hallmark of Fabry Disease," PNAS USA, 105: 2812-2817 (2008).

Alam, et al., "Glucosylceramide synthase inhibitors differentially affect expression of glycosphingolipds," Glycobiology, 25(4): 351-356 (2015).

Baosheng Fu, et al. (Eds.), "Highlights and Difficult Cases in Neurology," Science and Technology Literature Press, 1st edition, Feb. 2017, p. 53 (Partial English Translation).

Barranger, Glucosylceramide lipidosis: Gaucher disease. In: Scriver CR BA, Sly WS, Valle D, editor. The Metabolic Basis of inherited Disease. New York: McGraw-Hill. pp. 3635-3668 (2001).

Barton, et al., "Replacement Therapy for Inherited Enzyme Deficiency Macrophage-targeted Glucocerebrosidase for Gaucher's Disease," New England Journal of Medicine, 324: 1464-1470 (1991).

Beta-Glucocerebrosidase (GBA1/GCASE), The Michael J. Fox Foundation for Parkinson's Research.

Blandini et al., "Glucocerebrosidase Mutations and Synucleinopathies: Toward a Model of Precision Medicine" Mov Disord 2019; 34: 9-21.

(56) References Cited

OTHER PUBLICATIONS

Boyd et al. "Correction of lysosomal dysfunction as a therapeutic strategy for neurodegenerative diseases" Bioorg Med Chem Lett Jul. 15, 2014;24(14):3001-5.
Brat, et al., "Tau-associated Neuropathology in ganglion cell tumours increases with patient age but appears unrelated to ApoE genotype," Neuropathology and Applied Neurobiology, vol. 27 (2001), pp. 197-205.
Bremova-Ertl et al., "Oculomotor and Vestibular Findings in Gaucher Disease Type 3 and Their correlation with neurological Findings" Frontiers in Neurology 2018, vol. 8, pp. 1-19.
Brenkert, et al., "Synthesis of Galactosyl Ceramide and Glucosyl Ceramide by Rat Brain: Assay Procedures and Changes with Age," Brain Research, 36: 183-193 (1971).
Cabrera-Salazar, et al., "Intracerebroventricular Delivery of Glucocerebrosidase Reduces Substrates and Increases Lifespan in a Mouse Model of Neuronopathic Gaucher Disease," Experimental Neurology, 225: 436-444 (2010).
Czartoryska, et al., "Serum Chitotriosidase Activity in Gaucher Patients on Enzyme Replacement Therapy (ERT)," Clin. Biochem., 31: 417-420 (1998).
Davidson et al., The Neuronal Ceroid Lipofuscinosis, Clinical Features and Molecular Basis of Disease, Lysosomal Storage Disorders, {2007), pp. 371-388. Springer, New York, U.S.A.
Desnick R.J., et al., "Alpha-Galactosidase A Deficiency: Fabry Disease," In: The Metabolic and Molecular Bases of Inherited Disease, 7.sup.th Edition., Scriver., et al., Eds., McGraw-Hill, NY., pp. 2741-2784.
El Alwani, M. et al., "Regulation of the Sphingolipidsignaling Pathways in the Growing and Hypoxic Rat Heart," Prostaglandins & Other Lipid Mediators, vol. 78, No. 1-4, pp. 249-263, (2005).
Enquist, et al., "Murine Models of Acute Neuronopathic Gaucher Disease," PNAS, 104: 17483-17488 (2007).
Goker-Alpan O., et al., "Phenotypic Continuum in Neuronopathic Gaucher Disease: An Intermediate Phenotype Between Type 2 and Type 3," The Journal of Pediatrics, 2003, vol. 143 (2), pp. 273-276.
Grabowski G.A., et al., "Enzyme Therapy in Type 1 Gaucher Disease: Comparative Efficacy of Mannose-Terminated Glucocerebrosidase from Natural and Recombinant Sources," Annals of Internal Medicine, 1995, vol. 122 1), pp. 33-39.
Graler et al., Lysophospholipids and their G protein-coupled receplorsin inflammation and immunity, Molecular and Cell Biology of Lipids 1582: 168-174 (2002).
Guo, Y. et al., "Elevated Plasma Chiotriosidase Activity in Various Lysosomal Storage Disorders," J. Inher. Metab. Dis., 1995, 18, 717-722.
Hers H.G., "Inborn Lysosomal Diseases," Gastroenterology, 1965, vol. 48, pp. 625-633.
Hollak, et al., "Marked Elevation of Plasma Chitotriosidase Activity: A Novel Hallmark of Gaucher Disease," J. Clin. Invest., 93: 1288-1292 (1994).
Hsu, et al., "Endomyocardial biopsies in patients with left ventricular hypertrophy and a common Chinese later-onset fabry mutation (IVS4 + 919G > A)" Orphan et Journal of Rare Diseases, 2014, 9:96, pp. 2-11.
Ida, et al., "Clinical and Genetic Studies of Japanese Homozygotes for the Gaucher Disease L444P Mutation," Human Genetics, 105: 120-126 (1999).
James Shayman "Eliglustat tartrate, a prototypic glucosylceramide synthase inhibitor" Expert Rev Endocrinol Metab. Nov. 2013;8(6): 491-504.
Marshall, et al., "Substrate Reduction Augments the Efficacy of Enzyme Therapy in a Mouse Model of the Fabry Disease," PLoS One, 53: 15033 (2010).
Mehta, et al., "Fabry disease: a review of current management strategies," 2010, vol. 103, pp. 641-659.
Morales L.E., "Gaucher's Disease: A Review," Annals of Pharmacotherapy, 1996, vol. 30 (4), pp. 381-388.
Ortiz, et al., "Fabry disease revisited: Management and treatment recommendations for adult patients" Molecular Genetics and Metabolism 123, 2018, pp. 416-427.
Pastores, et al., "Enzyme Therapy in Gaucher Disease Type 1: Dosage Efficacy and Adverse Effects in 33 Patients Treated for 6 to 24 Months," Blood, 82: 408-416 (1993).
Pelled et al., The increased sensitivity of neurons with elevated glucocerebroside to neurotoxic agents can be reversed by imiglucerase, Journal of Inherited Metabolic Disease 23: 175-184 (2000).
Polinski, et al. "Decreased glucocerebrosidase activity and substrate accumulation of glycosphingolipids in a novel GBA 1 D409V knock-in mouse model" Plos One, 1-31, 2021.
Sardi et al., Proc Natl Acad Sci USA 2017; 114: 2699-704.
Treiber A., et al., "The Pharmacokinetics and Tissue Distribution of the Glucosylceramide Synthase Inhibitor Miglustat in the Rat," Xenobiotica, vol. 37 (3), pp. 298-314.
Yamashita, et al., "A vital role for glycosphingolipid synthesis during development and differentiation." Acad. Sci., 99(16): 9142-9147 (1999).
Buda, P. et al. (2012, e-pub. Nov. 4, 2011). "Gastrointestinal Phenotype Of Fabry Disease In A Patient With Pseudoobstruction Syndrome," JIMD Reports—Case And Research Reports Jan. 2012:25-28.
Hilz, M. J. et al. (2018, e-pub. Mar. 1, 2018). "Non-specific Gastrointestinal Features: Could it be Fabry Disease?." Digestive and Liver Disease 50(5):429-437.
Zar-Kessler, C. et al. (2016). "Understanding The Gastrointestinal Manifestations Of Fabry Disease: Promoting Prompt Diagnosis," Therapeutic Advances In Gastroenterology 9(4):626-634.
Ashe, K.M. et al. (2015, e-pub. Apr. 30, 2015). "Efficacy of Enzyme and Substrate Reduction Therapy with a Novel Antagonist of Glucosylceramide Synthase for Fabry Disease," Molecular Medicine 21:389-399.
Auray-Blais, C. et al. (2010, e-pub Aug. 14, 2010). "How Well Does Urinary Lyso-gb3 Function as Biomarker in Fabry Disease?" Clinica Chimica Acta 411 (23-24):1906-1914.
Bangari, D.S. et al. (Mar. 2015). "α-Galactosidase A Knockout Mice: Progressive Organ Pathology Resembles the Type 2 Later-Onset Phenotype of Fabry Disease," The American Journal of Pathology 185(3):651-665.
Banker, G.S. et al. (2002). "Prodrugs," Modern Pharmaceutics, pp. 451 and 596.
Bastin, R.J. et al. (Jan. 1, 2000). "Salt Selections and Optimisation for Pharmaceutical New Chemical Entities," Organic Process Research and Development 4(5):427-435.
Beniaminovitz, A. et al. (2000) "Prevention of Rejection in Cardiac Transplantation by Blockade of the Interleukin-2 Receptor with a Monoclonal Antibody," New England Journal of Medicine 342(9):613-619.
Berard, J.L. et al. (1999). "A Review of Interleukin-2 Receptor Antagonists in Solid Organ Transplantation," Pharmacotherapy 19(10):1127-1137.
Branco, L. et al. (Nov. 27, 1999). "Selective Deletion of Antigen-Specific, Activated T Cells by a Humanized MAB to CO2(Medi-507) is Mediated by NK Cells," Transplantation 68(10):1588-1596.
Bremova-Ertl, T. et al. (Jan. 15, 2018). "Oculomotor and Vestibular Findings in gaucher Disease Type 3 and Their correlation with neurological Findings," Frontiers in Neurology 8(711):1-19.
Bundgard, H. (1985)."Design of Prodrugs," Elsevier Science Publishers B.V. (Biomedical Division), pp. 7-9, 21-24.
Caira, M.R. (1999, e-pub. Jan. 1, 1999). "Crystalline Polymorphism of Organic Compounds," Topics in Current Chemistry 198:163-208.
CAS Registration No. 1070460-12-6.
CAS Registration No. 865147-82-6.
Ceravolo, R. et al. (2016, e-pub. Dec. 8, 2015). "A Review Of Adverse Events Linked To Dopamine Agonists In The Treatment Of Parkinson's Disease," Expert Opinion on Drug Safety 15(2):181-198.
Cerbai, G. et al. (Mar. 1972). "Acetylene Derivatives With Antispastic Activity. II. Amino Esters Of Propylpropargylacetic Acid," Farmaco, Edizione Scientifica 27(3):217-234.
Chinese Search Report for CN 202080025346.0, mailed May 25, 2023, English Translation.

(56) References Cited

OTHER PUBLICATIONS

Chirmule, N. et al. (Apr. 2000). "Readministration of Adenovirus Vector in Nonhuman Primate Lungs by Blockade of CD40-CD40 Ligand Interactions," J. Virol. 74(7): 3345-3352.
Conradi, N.et al. (Jul. 1991). "Late-infantile Gaucher Disease in a Child with Myoclonus and Bulbar Signs: Neuropathological and Neurochemical Findings," Acta Neuropathologica 82(2):152-157.
Conradi, N.G. et al. (Jun. 1984). "Neuropathology of the Norrbottnian Type of Gaucher Disease," Acta Neuropathologica 65(2):99-109.
Cullen, V. et al. (2011). "Acid-Glucosidase Mutants Linked to Gaucher Disease, Parkinson Disease, and Lewy Body Dementia Alter a-Synuclein Processing," American Neurological Association 69:940-953.
Czartoryska, B. et al. (Mar. 2000). "Changes in Serum Chitotriosidase Activity with Cessation of Replacement Enzyme (Cerebrosidase) Administration in Gaucher Disease," Clin. Biochem. 33(2):147-149.
De Kloe, G.E. et al. (2010, e-pub. Sep. 9, 2010). "Surface Plasmon Resonance Biosensor Based Fragment Screening Using Acetylcholine Binding Protein Identifies Ligand Efficiency Hot Spots (LE Hot Spots) by Deconstruction of Nicotinic Screening Using Acetylcholine Binding Protein Identifies Ligand Efficiency Hot Spots (LE Hot Spots) by Deconstruction of Nicotinic Screening Using Acetylcholine Binding Protein Identifies Ligand Efficiency Hot Spots (LE Hot Spots) by Deconstruction of Nicotinic Acetylcholine Receptor $\alpha7$ Ligands," Journal of Medicinal Chemistry 53.
Demaagd, G. et al. (Aug. 2015). "Parkinson's Disease and Its Management: Part 1: Disease Entity, Risk Factors, Pathophysiology, Clinical Presentation, and Diagnosis," Pharmacy and Therapeutics 40(8):504-532.
Demain, I. et al. (1989). "Enantiomeric Purity Determination Of 3-Aminoquinuclidine By Diastereomeric Derivatization And High-Performance Liquid Chromatographic Separation," Journal of Chromatography 466:415-420.
Den Tandt, W.R. et al. (May 1996). "Marked Increase of Methylumbelliferyl-tetra-N-acetylchitotetraoside Hydrolase Activity in Plasma from Gaucher Disease Patients," J. Inherit. Metab. Dis. 19(3):344-350.
Dodelson De Kremer, R. et al. (Jan. 1997). "[Plasma Chitotriosidase Activity in Argentinian Patients with Gaucher Disease, Various Lysosomal Diseases and Other Inherited Metabolic Disorders]," Medicina 57 (6):677-684.
Dorwald, F. Zaragoza. Side Reactions in Organic Synthesis: A Guide to Successful Synthesis Design, Weinheim: Wiley-VCR Verlag GmbH & Co. KGaA, 2005, Preface.
Eckhoff, D.E. et al. (May 15, 2000). "The Safety and Efficacy of a Two-Dose Daclizumab (Zenapax) Induction Therapy in Liver Transplant Recipients," Transplantation 69(9):1867-1872.
Ekberg, H. et al. (2000). "Daclizumab Prevents Acute Rejection and Improves Patient Survival Post Transplantation: 1 Year Pooled Analysis," Transplant International 13(2):151-159.
European Search Report for EP 2685986, "Glucosylceramide Synthase Inhibitors," mailed Feb. 4, 2015.
Feuerbach, D. et al. (Apr. 6, 2007). "JN403, In Vitro Characterization Of A Novel Nicotinic Acetylcholine Receptor A7 Selective Agonist," Neuroscience Letters, pp. 61-65.
Fishwild, D.M. et al. (Aug. 1999). "Differential Effects of Administration of a Human Anti-CD4 Monoclonal Antibody, HM6G, in Nonhuman Primates," Clin. Immunol. 92(2): 138-152.
Gaenslen, A. et al. (2011, e-pub. Mar. 2, 2011). "The Patient's Perception of Prodromal Symptoms Before the Initial Diagnosis of Parkinson's Disease," Movement Disorders: Official Journal of Movement Disorder Society 26(4):653-658.
Gambarin, F.I. et al. (2010). "When Should Cardiologists Suspect Anderson-Fabry Disease?" The American Journal of Cardiology 106(10):1492-1499.
Gaziev, D. et al. (Mar. 27, 2000). "Chronic graft-versus-host disease: is there an alternative to the conventional treatment?" Bone Marrow Transplant 25:689-696.
Giri, S. et al. (2006, e-pub. Apr. 27, 2006). "Krabbe Disease: Psychosine-mediated Activation of Phospholipase A2 in Oligodendrocyte Cell Death," Journal of Lipid Research 47:1478-1492.
Goedert, M. (2005). "Tau Gene Mutations and Their Effects," Movement Disorders 20(12):S45-S52.
Goetz, C.G. et al. (2007, e-pub. Nov. 17, 2006). "Movement Disorder Society-Sponsored Revision of the Unified Parkinson's Disease Rating Scale (MDS-UPDRS): Process, Format, and Clinimetric Testing Plan," Mov Disord 22: 41-47.
Goetz, C.G. et al. (2008). "Movement Disorder Society-Sponsored Revision of the Unified Parkinson's Disease Rating Scale (MDS-UPDRS): Scale Presentation and Clinimetric Testing Results," Mov Disord 23:2129-2170, 33 pages.
Grover, S. et al. (Jan.-Mar. 2015). "Psychiatric Aspects Of Parkinson's Disease," Journal Of Neurosciences In Rural Practice 6(1):65-76.
Gummert, J.F. et al. (1999). "Newer Immunosuppressive Drugs: A Review," J. Am. Soc. Nephrol. 10: 1366-1380.
Gundisch, D. et al. (2004, e-pub. Jul. 27, 2004). "Synthesis And Evaluation Of Phenylcarbamate Derivatives As Ligands For Nicotinic Acetylcholine Receptors," Bioorganic & Medicinal Chemistry 12(18):4953-4962.
Gura, T. (Nov. 7, 1997). "Systems For Identifying New Drugs Are Often Faulty," Science 278 (5340):1041-1042.
He, L. et al. (Eds.), Clinical Genetics (Shanghai Science and Technology Press, pt edition, May 31, 2013), p. 447, left col., paragraph 1, and p. 448, left col., paragraph 2, English Language Translation.
Henry, M.L. et al. (Dec. 25, 2001). "Cyclosporine and Tacrolimus (FK506): A Comparison of Efficacy and Safety Profiles," Clinical Transplantation 13(3)209-220.
Hildebrandt, F. et al. (Apr. 21, 2011). "Mechanisms of Disease," N Engl J Med, 364:1533-1543.
Hoehn, M. M. et al. (May 1967). "Parkinsonism: Onset, Progression, and Mortality," Neurology 17(5):427-442.
Hollak, C. E. (2007). "Novel Therapeutic Targets for the Treatment of Fabry Disease," Expert Opinion on Therapeutic Targets 11(6):821-833.
Hong, J.C. et al. (Mar. 1, 2000). "Immunosuppressive Agents in Organ Transplantation: Past, Present, and Future," Seminars in Nephrology 20(2):108-125.
Horak, J. et al. (Dec. 15, 2010, e-pub. Oct. 30, 2010). "Optimization Of A Ligand Immobilization And Azide Group Endcapping Concept Via "Click-Chemistry" For The Preparation Of Adsorbents For Antibody Purification," Journal of Chromatography B, Analytical Technologies in the Biomedical and Life Science 878(32):3382-3394.
Ideguchi, M. et al. (2000). "Local Adenovirus-Mediated CTLA4-Immunoglobulin Expression Suppresses the Immune Responses to Adenovirus Vectors in the Brain," Neuroscience 95(1):217-226.
International Preliminary Report on Patentability issued Mar. 17, 2015, mailed Nov. 18, 2013, for Patent Application No. PCT/US2013/058896, filed Sep. 10, 2013, 9 pages.
International Search Report and Written Opinion of the Searching Authority mailed on Nov. 18, 2013, for Patent Application No. PCT/US2013/058896, 15 pages.
International Search Report for International Application No. PCT/US2014/069338, mailed Mar. 12, 2015, 4 pages.
International Search Report for International Application No. PCT/US2016/021512, mailed May 23, 2016, 4 pages.
Irvine, G.B. et al. (Jul.-Aug. 2008). "Protein Aggregation in the Brain: The Molecular Basis for Alzheimer's and Parkinson's Diseases," Mol Med. 14(7-8):451-464.
Ito, D. et al. (2000). "Induction of CTL Responses by Simultaneous Administration of Liposomal Peptide Vaccine with Anti-CD40 and Anti-CTLA-4 mAb," J. Immunol. 164:1230-1235.
Johnson, J.I. et al. (2001). "Relationship Between Drug Activity In NCI Preclinical In Vitro And In Vivo Models And Early Clinical Trials," British Journal of Cancer 84(10):1424-1431.
Jordan, V.C. (Mar. 2003). "Tamoxifen: A most Unlikely Pioneering Medicine," Nature Reviews 2:205-213.

(56) References Cited

OTHER PUBLICATIONS

Kodanko, J.J. et al. (Oct. 13, 2005). "Synthesis of Diethynyltriptycene-linked Dipyridyl Ligands," Organic Letters 7(21):4585-4588.
Kurlberg, G. et al. (2000). "Blockade of the B7-CD28 Pathway by CTLA4-Ig Counteracts Rejection and Prolongs Survival n Small Bowel Transplantation," Scandinavian Journal of Immunology 51(3):224-230.
Lal, T.R. et al. (Mar. 2, 2017). "The Spectrum of Neurological Manifestations Associated with Gaucher Diseases," Diseases 5(10):1-11.
Lee, V.M.Y. (Oct. 6, 2006)."Mechanisms of Parkinson's Disease Linked to Pathological α-Synuclein: New Targets for Drug Discovery," Elsevier Inc., Neuron 52:33-38.
Leonard, W.J. et al. (2000). "Cytokine Receptor Signaling Pathways," J. Allergy Clin. Immunol. 105:877-888.
Liu, Y. et al. (Mar. 1998). "Mice with type 2 and 3 Gaucher Disease Point Mutations Generated by a Single Insertion Mutagenesis Procedure (SIMP)," PNAS 95:2503-2508.
Marinova-Mutafchieva, L. et al. (Mar. 2000). "A Comparative Study into the Mechanisms of Action and Anti-Tumor Necrosis Factor a/Anti-CD4, and Combined Anti-Tumor Necrosis Factor a/Anti-CD4 Treatment in Early Collagen-Induced Arthritis," Arthritis Rheum. 43(3):638-644.
Marks, D.L. et al. (Jul. 13, 2001, e-pub. May 3, 2001). "Identification of Active Site Residues in Glucosylceramide Synthase," Journal of Biological Chemistry 276(28):26492-26498.
Marshall, J. et al. (Jun. 2016, e-pub. Apr. 5, 2016)."CNS-accessible Inhibitor of Glucosylceramide Synthase for Substrate Reduction Therapy ofNeuronpathic Gaucher Disease," Official Journal of the American Society of Gene & Cell Therapy 24(6):1019-1029.
Mashkovsky, M.D. (1961) "The Relationship Between the Chemical Structure and Pharmacological Activity of Some Esters of 3-Hydroxyquinuclidine (Quinuclidine-3-OL)," Proc. Intern. Pharmacol. Meeting, 1st, Stockholm, 1963, 7: 356-366, 8 pages.
Masjedizadeh, M.R. et al. (1996). "Synthesis of Tritium Labelled (R) and (S)-3-Aminoquinuclidine: A Ubiquitous Component of Serotonin Receptor Lignads, Part I," Journal of Labelled Compounds and Radiopharmaceuticals, 11 pages.
Mazurov, A. et al. (2005, e-pub. Mar. 19, 2005). "2-(Arylmethyl)-3-Substituted Quinuclidines as Selective Alpha 7 Nicotinic Receptor Ligands," Bioorganic & Medicinal Chemistry Letters 15(8):2073-2077.
Mazzulli, J.R. et al. (2011). "Gaucher Disease Glucocerebrosidase and a-Synuclein Form a Bidirectional Pathogenic Loop in Synucleinopathies," Cell 146:37-52.
Merrill, A.H. Jr. et al. (Jun. 2005, e-pub. May 13, 2005). "Sphingolipidomics: High-Throughput, Structure-Speciwc, And Quantitative Analysis Of Sphingolipids By Liquid Chromatographytandem Mass Spectrometry," Methods 36(2):207-224.
Migdalska-Richards, A. et al. (2016). "The Relationship Between Glucocerebrosidase Mutations And Parkinson Disease," J Neurochem 139(Suppl. 1):77-90.
Mistry, P.K. et al. (Dec. 1997). "A Practical Approach to Diagnosis and Management of Gaucher's Disease," Baillieres Clinical Haematology 10(4):817-838.
Mistui, J. et al. (May 2009). "Mutations for Gaucher Disease Confer High Susceptibility to Parkinson Disease," Arch Neurol 66(5):571-576.
Naito, R. et al. (Aug. 1998). "Selective Muscarinic Antagonists. II. 1) Synthesis and Antimuscarinic Properties of Biphenylylcarbamate Derivatives," Chem. Pharm. Bull. 46(8):286-1294.
Nasreddine, Z. (2005). "The Montreal Cognitive Assessment, MoCA: A Brief Screening Tool For Mild Cognitive Impairment" J Am Geriatr Soc 53(4):695-699.
Natoli, T.A. (Jul. 2010). "Inhibition Of Glucosylceramide Accumulation Results In Effective Blockade Of Polycystic Kidney Disease In Mouse Models," Nat Med. 16(7):788-792, 13 pages.
Nevins, T.E. (Apr. 2000). "Overview of New Immunosuppressive Therapies," Curr. Opin. Pediatr. 12(2):146-150.
Nilsson, O. et al. (Sep. 1982). "Accumulation of Glucosylceramide and Glucosylsphingosine (Psychosine) in Cerebrum and Cerebellum in Infantile and Juvenile Gaucher Disease," Journal of Neurochemistry 39(3):709-718.
Noelker, C. et al. (2015). "Glucocerebrosidase Deficiency And Mitochondrial Impairment In Experimental Parkinson Disease," Journal of the Neurological Sciences 356(1-2):129-136, 30 pages.
O'Donnell, C.J. et al. (2009, e-pub. Jun. 17, 2009). "Synthesis and SAR Studies of 1,4-diazibicyclo[3.2.2]nonane phenyl carbamates—Subtype Selective, High Affinity a7 Nicotinic Acetylcholine Receptor Agonists," Bioorganic and Medicinal Chemistry Letters 19(16):4747-4751.
Oberholzer, A. et al. (Apr. 2000). "Cytokine Signaling-Regulation of the Immune Response in Normal and Critically ill States," Critical Care Medicine 28(4):N3-N12, 16 pages.
Ohshima, T. et al. (Mar. 1997). "α-Galactosidase A Deficient Mice: A Model Of Fabry Disease," Proceedings Of The National Academy Of Sciences 94(6):2540-2544.
Orr, M.E. et al. (Jul. 2017). "A Brief Overview of Tauopathy: Causes, Consequences, and Therapeutic Strategies," Trends Pharmacol Sci. 38(7):637-648.
Orvisky, E. et al. (2000). "Glucosylsphingosine Accumulation in Mice and Patients with Type 2 Gaucher Disease Begins Early in Gestation," Pediatric Research 48(2):233-237.
Orvisky, E. et al. (2002). "Glucosylsphingosine Accumulation In Tissues From Patients With Gaucher Disease: Correlation With Phenotype And Genotype," Molecular Genetics and Metabolism 76:262-270.
Palavra, N.C. et al. (2013). "Mild Cognitive Impairment In Parkinson's Disease: A Review Of Current Concepts," Neurology Research International 2013(576091), 8 pages.
Pfeiffer, B. (Mar. 2017). "Instantly Curbing Alzheimer's Disease," Shanghai Popular Science Press, 1st edition, p. 100 (Partial English Translation).
Poirier, A-A. et al. (2016). "Gastrointestinal Dysfunctions in Parkinson's Disease: Symptoms and Treatments" Parkinsons Dis 2016(6762528), 23 pages.
Politei, J.M. et al. (2016). "Pain in Fabry Disease: Practical Recommendations for Diagnosis and Treatment" CNS Neuroscience & Therapeutics 22:568-576.
Ponticelli, C. et al. (Jan. 1999). "Promising New Agents in the Prevention of Transplant Rejection," Drugs in R&D 1(1):55-60.
Potter, M.A. et al. (1999). "Review—The Use of Immunosuppressive Agents to Prevent Neutralizing Antibodies against a Transgene Product," Annals of the New York Academy of Sciences 875:159-174.
Przepiorka, D. et al. (Dec. 1, 1998). "A Phase II Study ofBTI-322, a Monoclonal Anti-CD2 Antibody, for Treatment of Steroid-Resistant Acute Graft-Versus-Host Disease," Blood 92(11):4066-4071.
Qi, S. et al. (Apr. 15, 2000). "Effect of Tacrolimus (FK506) and Sirolimus (Rapamycin) Mono-and Combination Therapy in Prolongation of Renal Allograft Survival in the Monkey," Transplantation 69(7):1275-1283.
Riboldi, G.M. et al. (Apr. 19, 2019). "GBA, Gaucher Disease, and Parkinson's Disease: From Genetic to Clinic to New Therapeutic Approaches" Cells 8(4):364, 16 pages.
Rosenthal, D.I. et al. (Oct. 1995). "Enzyme Replacement Therapy for Gaucher Disease: Skeletal Responses to Macrophage-Targeted Glucocerebrosidase," Pediatrics 96(4):629-637.
Ross, C. et al. (2004, e-pub. Jul. 1, 2004) "Protein Aggregation and Neurodegenerative Disease," Nature Medicine 10:S10-S17.
Rubinstein, M. et al. (Jun. 1, 1998). "Recent Advances in Cytokines, Cytokine Receptors and Signal Transduction," Cytokine & Growth Factor Reviews 9(2):175-181.
Ryan, E.A. et al. (Apr. 2001). "Clinical Outcomes and Insulin Secretion after Islet Transplantation with the Edmonton Protocol," Diabetes 50(4):710-719.
Salsano, E. et al. (2012). "Vertical Supranuclear Gaze Palsy in Niemann-Pick Type C Disease," Neurol Sci 33:1225-1232.
Sardi, P.S. et al. (Mar. 7, 2017). "Glucosylceramide Synthase Inhibition Alleviates Aberrations In Synucleinopathy Models," Proceedings of the National Academy of Sciences 114(10):2699-2704.

(56) References Cited

OTHER PUBLICATIONS

Sardi, S.P. et al. (2016). "Glucosylceramide Synthase Inhibition Reduces A-Synuclein Pathology And Improves Cognition In Murine Models Of Synucleinopathy," Molecular Genetics and Metabolism 117(2): S102. (Abstract Only).
Scholl, M. et al. (Jul. 2015). "In Vivo Braak Staging Using 18F-AV1451 Tau PET Imaging," Alzheimer's & Dementia 11(7):P4, Abstract No. IC-01-05.
Schueler, U.H. et al. (2003). "Toxicity Of Glucosylsphingosine (Glucopsychosine) To Cultured Neuronalcells: A Model System For Assessing Neuronal Damage In Gaucher Disease Type 2 And 3," Neurobiology of Disease 14:595-601.
Shapiro, A.M.J. et al. (Jul. 27, 2000). "Islet Transplantation in Seven Patients with Type 1 Diabetes Mellitus Using a Glucocorticoid-Free Immunosuppressive Regimen," New England Journal of Medicine 343:230-238.
Shayman, J.A. (Mar. 2018). "Targeting Glucosylceramide Synthesis in the Treatment of Rare and Common Renal Disease," Semin Nephrol. 38(2):183-192.
Shen, W. et al. (2014). "Inhibition Of Glucosylceramide Synthase Stimulates Autophagy Flux In Neurons," Journal of Neurochemistry 129:884-894.
Sidransky, E. et al. (Oct. 22, 2009). "Multi-Center Analysis Of Glucocerebrosidase Mutations In Parkinson Disease," N Enzl J Med 361(17):1651-1661.
Skorvanek, M. et al. (2017). "Differences In MDS-UPDRS Scores Based On Hoehn And Yahr Stage And Disease Duration," Movement Disorders Clinical Practice 4(4):536-544.
Slavik, J.M. et al. (Feb. 1999). "CD28/CTLA-4 and CD80/CD86 Families: Signaling and Function," Immunologic Research 19(1):1-24.
Stella, V. J. (Dec. 2010). "Prodrugs: Some Thoughts And Current Issues," Journal Of Pharmaceutical Sciences 99(12):4755-4765.
Sun, D. et al. (2022). "Why 90% of Clinical Drug Development Fails And How To Improve It?" Acta Pharmaceutica Sinica B 12(7):3049-3062.
Sun, Y. et al. (2010, e-pub. Jan. 4, 2010). "Neuronopathic Gaucher Disease in the Mouse Viable Combined Selective Saposin C Deficiency and Mutant Glucocerebrosidase (V394L) Mice with Glucosylsphingosine and Glucosylceramide Accumulation and Progressive Neurological Deficits," Hum. Mol. Genet. 19(6):1088-1097.
Thurberg, B. et al. (2004). "Monitoring the 3-Year Efficacy of Enzyme Replacement Therapy in Fabry Disease by Repeated Skin Biopsies," The Journal of Investigative Dermatology 122:900-908.
Thurberg, B.L. et al. (2009)."Cardiac Microvascular Pathology in Fabry Disease Evaluation of Endomyocardial Biopsies Before and After Enzyme Replacement Therapy," Circulation 119(19):2561-2567.
Turzanski, J. et al. (2005). "P-Glycoprotein is Implicated in the Inhibition of Ceramide-induced Apoptosis in TF-1 Acute Myeloid Leukemia Cells by Modulation of the Glucosylceramide Synthase Pathway," Experimental Hematology 33(1):62-72.
Urbanelli, L. et al. (2013). "Therapeutic Approaches for Lysosomal Storage Diseases: A Patent Update," Recent Patents on CNS Drug Discovery 8(2):1-19.
Wang, G. et al. (2009, e-pub. Apr. 16, 2009). "Regulation of Primary Cilia Formation by Ceramide," Journal of Lipid Research 50(10):2103-2110.
Weidong, Z. (Aug. 2013). (Ed.), "Cognitive Neurology," Military Medical Sciences Press, 1st edition, p. 227 (Partial English Translation).
Weinreb, N.J., et al. (Aug. 1, 2002). "Effectiveness of Enzyme Replacement Therapy in I 028 Patients with Type I Gaucher Disease after 2 To 5 Years of Treatment: A Report from the Gaucher Registry," The American Journal of Medicine 113(2):112-119.
Wemheuer, W. et al. (Jun. 16, 2017). "Types and Strains: Their Essential Role in Understanding Protein Aggregation in Neurodegenerative Diseases," Frontiers in Aging Neuroscience 9(187):1-13.
Wiersma, V.I. et al. (2020). "Untangling The Origin And Function Of Granulovacuolar Degeneration Bodies In Neurodegenerative Proteinopathies," Acta Neuropathologica Communications 8(153), 21 pages.
Wiseman, L.R. et al. (Dec. 1999). "Daclizumab: A Review of its use in the Prevention of Acute Rejection in Renal Transplant Recipients," Drugs 58(6):1029-1042.
Wolff, M.E. (1995). "Chapter 9—Some Consideration For Prodrug Design," in Burger's Medicinal Chemistry and Drug Discovery, 5th Edition, vol. 1: Principles and Practice, pp. 975-977, 4 pages.
Wong, K. et al. (2004, e-pub. Jun. 9, 2004). "Neuropathology Provides Clues to the Pathophysiology of Gaucher Disease," Molecular Genetics and Metabolism 82:192-207.
Young, E. et al. (Aug. 1, 1997). "Plasma Chitotriosidase Activity in Gaucher Disease Patients Who Have Been Treated either by Bone Marrow Transplantation or by Enzyme Replacement Therapy with Alglucerase," Journal of Inherited Metabolic Disease 20(4):595-602.
Zhao, J. et al. (Apr. 2, 2015). "Process Development of a GCS Inhibitor Including Demonstration of Lossen Rearrangement on Kilogram Scale," Organic Process Research Development 19(5), 22 pages.
Alzforum—"Feedback Loop"—Jun. 27, 2011, 12 pages.
Arends, M. et al. (2017). "Characterization Of Classical And Nonclassical Fabry Disease: A Multicenter Study," Journal Of The American Society Of Nephrology 28(5):1631-1641.
Bagirova, V.L. et al. (1998). "Modern Aspects of the Use of Excipients in Drug Technology," Pharmateka (6):34-36, (English Translation), 13 pages.
Balwani, M. et al. (2016). "Recommendations For The Use Of Eliglustat In The Treatment Of Adults With Gaucher Disease Type 1 In The United States," Molecular Genetics And Metabolism 117(2):95-103.
Beck, M. (2017, e-pub. Nov. 1, 2017). "Treatment Strategies For Lysosomal Storage Disorders," Developmental Medicine & Child Neurology 60(1):13-18.
Belikov, V.G. (2007). "Pharmaceutical Chemistry," MEDpress-inform 27-29, 10 pages (English Translation).
Bennett, L. L. et al. (2018). "Pharmacotherapy Of Gaucher Disease: Current And Future Options," Pharmacy and Therapeutics 43(5):274-280.
Beutler, E. et al. (2001) Gaucher disease. In: Scriver, C.R., Beaudet, A.L., Sly, W.S., and Valle, D., Eds., The Metabolic and Molecular Bases of Inherited Disease. McGraw-Hill, New York, 3635-3668.
Burlakova, E.B. et al. (Aug. 15, 2020). "Effects of Ultra-Small Doses of Biologically Active Substances and Low-Intensity Physical Factors," Problems of Regulation in Living and Prebiological Systems, Table 2, pp. 390-424, (English Translation), 43 pages.
Cabrera-Salazar, M.A. et al. (Aug. 17, 2012). "Systemic Delivery of a Glucosylceramide Synthase Inhibitor Reduces CNS Substrates and Increases Lifespan in a Mouse Model of Type 2 Gaucher Disease," PLoS One 7(8) e43310, 9 pages. doi:10.1371/journal.pone.0043310.
Cavaco, S. et al. (2013). "Trail Making Test: Regression-Based Norms For The Portuguese Population," Archives Of Clinical Neuropsychology 28(2):189-198.
Chang et al. (Jan. 31, 2000). "MRI in acute neuropathic Gaucher's disease", Neuroradiology 42(1):48-50.
Cocozza, S. et al. (2018). "Neuroimaging in Fabry disease current knowledge and future directions," Insights into Imaging 9:1077-1088.
Davies, E. H. et al. (May 28, 2011). "Four-Year Follow-Up Of Chronic Neuronopathic Gaucher Disease In Europeans Using A Modified Severity Scoring Tool," Journal Of Inherited Metabolic Disease: Official Journal Of The Society For The Study Of Inborn Errors of Metabolism 34(5):1053-1059.
De Wildt et al. (1999) "Cytochrome P450 3A Ontogeny and Drug Disposition," Clin Pharmacokinet 37(6):485-505.
Dresser, G. et al. (2000) "Pharmacokinetic-Pharmacodynamic Consequences and Clinical Relevance of Cytochrome P450 3A4 Inhibition," Clinical Pharmacokinetics 38(1):41-57.

(56) References Cited

OTHER PUBLICATIONS

Dube, P. et al. (2009, e-pub. Nov. 12, 2009). "Carbonyldiimidazole-Mediated Lossen Rearrangement," Organic Letters 11(24):5622-5625.
Evidence-Based Medicine Consult, "Common Medications Classified as Weak, Moderate and Strong Inhibitors of CYP3A4", available online at: <https://www.ebmconsult.com/articles/medications-inhibitors-cyp3a4-enzyme>, Oct. 2015, 5 pages.
Farfel-Becker, T. et al. (2014). "Neuronal Accumulation Of Glucosylceramide In A Mouse Model Of Neuronopathic Gaucher Disease Leads To Neurodegeneration," Human Molecular Genetics 23(4): 843-854.
Fee, J. P. H. et al. (1987). "Cimetidine And Ranitidine Increase Midazolam Bioavailability," Clinical Pharmacology & Therapeutics 41(1):80-84.
Fernandez et al. (1988). "Synthesis of Ethylenediamines-a, a-disubstituted," Anales de la Real Academia de Farmacia 54:502-510 (English Summary).
Flockhart Table, "Drug Interactions: Cytochrome P450 Drug Interaction Table", Indiana University School of Medicine, available online at <https://drug-interactions.medicine.iu.edu>, 2007, 2 pages.
Geffken D. (1982). "3-(1-Hydroxyalkyl)-1,4,2-dioxazol-5-one und 3-Hydroxyoxazolidin-2,4-dione aus 2-Hydroxycarbohydroxamsauren und 1,1'-Carbonyldiimidazol)," Liebigs Annalen der Chemie, pp. 211-218. (English Abstract).
Generalenko, N.Y. et al. (2010). "Effects of Small and Ultra-Small Doses of Biologically Active Substances," Scientific and Educational Problems of Civil Protection—2010, pp. 6-7, (English Translation), 6 pages.
Germain, D. P. et al. (2018). "Phenotypic Characteristics of the P. Asn215Ser (P. N215S) GLA Mutation in Male And Female Patients with Fabry Disease: A Multicenter Fabry Registry Study," Molecular Genetics & Genomic Medicine 6(4):492-503.
Giasson, B. I. et al. (May 16, 2002). "Neuronal a-Synucleinopathy With Severe Movement Disorder In Mice Expressing A53T Human a-Synuclein," Neuron 34(4):521-533.
Giladi, N. et al. (2023). "Safety and Efficacy of Venglustat in GBA1-Associated Parkinson's Disease: An International, Multicentre, Double-Blind, Randomised, Placebo-Controlled, Phase 2 Trial," The Lancet Neurology 22(8):661-671.
Goetz, C.G. et al. (2004, e-pub. Jun. 16, 2004). "Movement Disorder Society Task Force Report on the Hoehn and Yahr Staging Scale: Status and Recommendations," Movement Disorders 19(9):1020-1028.
Hakkola, J. et al. (2020). "Inhibition and Induction of CYP Enzymes in Humans: An Update," Archives of Toxicology 94(11):3671-3722. doi:10.1007/s00204-020-02936-7.
Hirschhorn. R. (1995). "Glycogen Storage Disease Type II: Acid a-Glucosidase (Acid Maltase) Deficiency," Chapter 77 in The Metabolic and Molecular Bases of Inherited Disease, 7th ed., C.R. Scriver et al., Editors. McGraw-Hill, N.Y. pp. 2443-2464.
Ibiglustat, MedKoo CAT: 319547, CAS: 1401090-53-6, 2017, 3 pages.
International Preliminary Report on Patentability mailed Sep. 15, 2015, issued Jun. 16, 2021, for PCT Patent Application No. PCT/US2014/027081, filed Mar. 14, 2014, 6 pages.
International Preliminary Report on Patentability mailed Sep. 15, 2015, issued Sep. 15, 2015, for Application No. PCT/US2014/025384, filed Mar. 13, 2014, 13 pages.
International Search Report and Written Opinion mailed Aug. 18, 2014, for PCT Patent Application No. PCT/US2014/025384, filed Mar. 13, 2014, 20 pages.
International Search Report and Written Opinion mailed Jul. 2, 2012, for PCT Patent Application No. PCT/US2012/029417, filed Mar. 16, 2012, 11 pages.
International Search Report and Written Opinion mailed May 20, 2014, for PCT Patent Application No. PCT/US2014/027081, filed Mar. 14, 2014, 9 pages.
IUPHAR/BPS guide to pharmacology (Year: 2023), 2 pages.
Ji, A. J. et al. (2015). "A Novel Approach For Quantitation Of Glucosylceramide In Human Dried Blood Spot Using LC-MS/MS," Bioanalysis 7(12):1483-1496.
Kharkevich, D.A. (2006)."Pharmacology," Moscow, p. 62, (English Translation), 5 pages.
Krasnyuk, I.I. et al. (2006). "Pharmaceutical Technology: Technology of Dosage Forms: a Textbook for Students," Higher Proc. Institutions, 2nd ed., revised—Moscow: Publishing Center "Akademiya," p. 6, (English Translation), 5 pages.
Lam, Y.W.F. et al. (2003). "Pharmacokinetic And Pharmacodynamic Interactions Of Oral Midazolam With Ketoconazole, Fluoxetine, Fluvoxamine, And Nefazodone," The Journal of Clinical Pharmacology 43(11):1274-1282.
Lavalle, L. et al. (Apr. 5, 2018). "Phenotype And Biochemical Heterogeneity In Late Onset Fabry Disease Defined By N215S Mutationm," PLoS One 13(4):e0193550, 20 pages.
Macpherson, S. E. et al. (2017). "Processing Speed And The Relationship Between Trail Making Test-B Performance, Cortical Thinning And White Matter Microstructure In Older Adults," Cortex 95:92-103.
Malec-Litwinowicz, M. et al. (2014, e-pub. Jul. 29, 2014). "Cognitive Impairment In Carriers Of Glucocerebrosidase Gene Mutation In Parkinson Disease Patients" Neurologia I Neurochirurgia Polska 48(4):258-261.
Mashkovsky, M.D. (2002). "Medicinal Products," 14th Edition, vol. 1, Moscow, pp. 8-9, (English Translation), 8 pages.
Middleton, W.J. (Oct. 1, 1983). "1,3,4-Dioxazol-2-ones: a potentially hazardous class of compounds," The Journal Of Organic Chemistry 48(21):3845-3847.
Mielke, M. M. et al. (Sep. 2013). "Plasma Ceramide And Glucosylceramide Metabolism Is Altered In Sporadic Parkinson's Disease And Associated With Cognitive Impairment: A Pilot Study," PloS one 8(9):e73094, 6 pages.
Mikhlina, E. E. et al. (1960). "New Paths of Synthesis of 3-quinuclidineacetic Acid," Zhurnal Obshchei Khirnii 30:2970-2977, (English Translation), 16 pages.
Moder, K.G. (2000). "New Medications for Use in Patients with Rheumatoid Arthritis," Annals of Allenzv, Asthma &Immunology 4(3):280-284.
Molenaar-Kuijsten, L. et al. (Aug. 2021). "A Review of CYP3A Drug-Drug Interaction Studies: Practical Guidelines for Patients Using Targeted Oral Anticancer Drugs", Frontiers in Pharmacology 12: 20 pages.
Murphy, K. E. et al. (2014, e-pub. Jan. 28, 2014). "Reduced Glucocerebrosidase Is Associated With Increased a-Synuclein In Sporadic Parkinson's Disease," Brain 137(3):834-848.
Nair, V. et al. (2019). "Lysosomal Storage Disorders Affecting The Heart: A Review," Cardiovascular Pathology 39:12-24.
Ohshima, T. et al. (May 1999). "Aging Accentuates And Bone Marrow Transplantation Ameliorates Metabolic Defects In Fabry Disease Mice," Proceedings Of The National Academy Of Sciences 96(11):6423-6427.
Olkkola, K. T. et al. (1996). "The Effect Of The Systemic Antimycotics, Itraconazole And Fluconazole, On The Pharmacokinetics And Pharmacodynamics Of Intravenous And Oral Midazolam," Anesthesia & Analgesia 82(3):511-516.
Oudit, G. Y. et al. (Jan. 21, 2025). "A Systematic Literature Review To Evaluate The Cardiac And Cerebrovascular Outcomes Of Patients With Fabry Disease Treated With Agalsidase Beta," Frontiers in Cardiovascular Medicine 11:1415547, 21 pages.
Parenti, G. et al. (2021, e-pub. Jan. 18, 2021). "The Rapidly Evolving View Of Lysosomal Storage Diseases," EMBO Molecular Medicine 13(2):E12836, 21 Pages.
Pathan, S. A. et al. (2009). "CNS Drug Delivery Systems: Novel Approaches," Recent Patents On Drug Delivery & Formulation 3(1):71-89.
Patnaik, S. et al. (Jun. 28, 2012). "Discovery, Structure—Activity Relationship, And Biological Evaluation Of Noninhibitory Small Molecule Chaperones Of Glucocerebrosidase," Journal Of Medicinal Chemistry 55(12):5734-5748, 42 pages.

(56) References Cited

OTHER PUBLICATIONS

Pearce, H. L. et al. (2008). "Failure Modes in Anticancer Drug Discovery and Development," Chapter 18 in Cancer Drug Design and Discovery, Stephen Neidle, ed. Elsevier/Academic Press, pp. 424-435.
Peterschmitt, J.M. et al. (2019). "Safety, Pharmacokinetics, And Pharmacodynamics Of Oral Venglustat In 6 Parkinson Disease Patients With A GBA Mutation From Japan And The Rest Of The World: Results From Part 1 Of The MOVES-PD Study," Molecular Genetics and Metabolism 129:S128, Abstract No. 325.
Peterschmitt, M. J. et al. (2021). "Pharmacokinetics, Pharmacodynamics, Safety, And Tolerability Of Oral Venglustat In Healthy Volunteers," Clinical Pharmacology In Drug Development 10(1):86-98.
Peterschmitt, M. J. et al. (2022). "Safety, Pharmacokinetics, And Pharmacodynamics Of Oral Venglustat In Patients With Parkinson's Disease And A GBA Mutation: Results From Part 1 Of The Randomized, Double-Blinded, Placebo-Controlled MOVES-PD Trial," Journal Of Parkinson's Disease 12(2):557-570.
Pieroni, M. et al. (Feb. 23, 2021). "Cardiac Involvement In Fabry Disease: JACC Review Topic Of The Week," Journal Of The American College of Cardiology 77(7):922-936.
Przedborski, S. (Jan. 2003). "Neurodegeneration: What Is It And Where Are We?," The Journal of Clinical Investigation 111(1):3-10.
Ramanathan, R. et al. (Mar. 12, 2012). "The Emergence Of High-Resolution MS As The Premier Analytical Tool In The Pharmaceutical Bioanalysis Arena," Bioanalysis 4(5):467-469.
Sardi, S. P. et al. (Feb. 2024). "Venglustat In GBA1-Related Parkinson's Disease," The Lancet Neurology 23(2):137.
Schmitz-Hubsch, T. et al. (2006). "Scale For The Assessment And Rating Of Ataxia: Development Of A New Clinical Scale," Neurology 66(11):1717-1720.
Schuchman, E. H. et al. (2021). "New Paradigms For The Treatment Of Lysosomal Storage Diseases: Targeting The Endocannabinoid System As A Therapeutic Strategy," Orphanet Journal Of Rare Diseases 16(1):151, 6 pages.
Schwartz, J. B. et al. (1988). "Effect Of Cimetidine Or Ranitidine Administration On Nifedipine Pharmacokinetics And Pharmacodynamics," Clinical Pharmacology & Therapeutics 43(6):673-680.
Sharma, J. et al. (Feb. 2023). "PBPK Modeling to assess Drug-Drug Interaction Potential of Venglustat With CYP3A Inhibitors", Clinical Pharmacology & Therapeutics, Abstract PII-098, 113(S1):S74, 1 page.
Shayman, J. A. et al. (2014, e-pub. Feb. 16, 2014). "The Development And Use Of Small Molecule Inhibitors Of Glycosphingolipid Metabolism For Lysosomal Storage Diseases," Journal Of Lipid Research 55(7):1215-1225.
Shayman, J.A. (Aug. 1, 2010). "Eliglustat Tartrate: Glucoslyceramide Synthase Inhibitor Treatment of Type 1 Gaucher Disease," Drugs Future 35(8):613-620.
Shimohata, H. et al. (2016). "A Renal Variant Of Fabry Disease Diagnosed By The Presence Of Urinary Mulberry Cells," Internal Medicine 55(23):3475-3478.
Sidransky, E. et al. (Nov. 2012). "The Link Between the GBA Gene and Parkinsonism," The Lancet Neurology 11(11):986-998.
Silverman, R.B. et al. (1992). "Prodrugs and Drug Delivery Systems," The Organic Chemistry of Drug Design and Drug Action, pp. 352-401, Academic Press, San Diego, California.
Smith, S. M. et al. (2009). "Correspondence Of The Brain's Functional Architecture During Activation And Rest," Proceedings Of The National Academy Of Sciences 106(31):13040-13045.
Sun, A. (2018). "Lysosomal Storage Disease Overview," Ann Transl Med 6(24):1-14.
Sun, C. et al. (Apr. 17, 2021). "Treatment of Parkinson's Disease with Cognitive Impairment: Current Approaches and Future Directions," Behav Sci (Basel) 11(4):54, 21 pages.
Taketomi, T. et al. (1996). "Rapid Method Of Preparation Of Lysoglycosphingolipids And Their Confirmation By Delayed Extraction Matrix-Assisted Laser Desorption Ionization Time-Of-Flight Mass Spectrometry," The Journal Of Biochemistry 120(3):573-579.
Tallaksen, C.M.E. et al. (2009). "Miglustat Therapy in Juvenile Sandhoff Disease," J Inherit Metab Dis 32(Suppl 1):S289-S293.
Thompson, P. M. et al. (Feb. 2007). "Tracking Alzheimer's Disease," Annals Of The New York Academy Of Sciences 1097(1):183-214.
Tombaugh, T. N. (2004). "Trail Making Test A and B: Normative Data Stratified by Age And Education," Archives of clinical neuropsychology 19(2):203-214.
U.S. Appl. No. 18/777,773, filed Jul. 19, 2024, for Elyse Bourque et al. (Copy not submitted herewith pursuant to the waiver of 37 C.F.R. 1.98(a)(2)(iii) issued by the Office on Sep. 21, 2004).
U.S. Appl. No. 19/132,336, filed May 22, 2025, for Crawford Nigel Patrick Somerville et al. (Copy not submitted herewith pursuant to the waiver of 37 C.F.R. 1.98(a)(2)(iii) issued by the Office on Sep. 21, 2004).
Wanner, C. et al. (2023, e-pub. Apr. 29, 2023). "Global Reach Of Over 20 Years Of Experience In The Patient-Centered Fabry Registry: Advancement Of Fabry Disease Expertise And Dissemination Of Real-World Evidence To The Fabry Community," Molecular Genetics and Metabolism 139(3):107603, 11 pages.
Weidemann, F. et al. (2009). "Long-Term Effects of Enzyme Replacement Therapy on Fabry Cardiomyopathy: Evidence for a Better Outcome With Early Treatment," Circulation 119(4):524-529.
Weidemann, F. et al. (2013). "Long-Term Outcome of Enzyme-Replacement Therapy in Advanced Fabry Disease: Evidence for Disease Progression Towards Serious Complications," Journal Of Internal Medicine 274(4):331-341.
Weidemann, F. et al. (2019, e-pub. Nov. 12, 2018). "Early Detection of Organ Involvement in Fabry Disease by Biomarker Assessment in Conjunction with LGE Cardiac MRI: Results from the SOPHIA Study," Molecular Genetics And Metabolism 126(2):169-182.
Wilner, K. et al. (2002). "The Effects Of Cimetidine And Antacid On The Pharmacokinetic Profile Of Sildenafil Citrate In Healthy Male Volunteers," British Journal Of Clinical Pharmacology 53:31S-36S.
Xu, X. T. et al. (2021). "A Four-Oil Intravenous Lipid Emulsion Improves Markers Of Liver Function, Triglyceride Levels And Shortens Length Of Hospital Stay In Adults: A Systematic Review And Meta-Analysis," Nutrition Research 92:1-11.
Zhang, M. et al. (Oct. 8, 2018) "Altered Brain Functional Network in Children with Type 1 Gaucher Disease: A Longitudinal Graph Theory-based Study," Neuroradiology 61(1):63-70.
Zheng, K. et al. (2016, e-pub. Aug. 7, 2016). "Enhancement Of Human Plasma Glucosylceramide Assay Sensitivity Using Delipidized Plasma," Molecular Genetics and Metabolism Reports 8:77-79.
Ghisaidoobe, A. et al. (Dec. 2, 2010). "Identification Of Potent And Selective Glucosylceramide Synthase Inhibitors From A Library Of N-Alkylated Iminosugars," ACS Medicinal Chemistry Letters 2(2):119-123.
Kholodov, L.E. et al. (1983). "Pharmaco Clinical Kinetics: A Guide," Management, Chapter 3, 47 pages, (English Translation).
Mashkovsky, M.D. (2012). "Academician of the Russian Academy of Medical Sciences, Doctor of Medical Sciences, Professor, Hero of Socialist Labor" Medicine, Sixteenth Edition, 7 pages (English Translation).
Sergeeva, P.V. (1975). "Short Course in Molecular Pharmacology," Ministry of Health of the Russian Soviet Federal Soviet Republic and the N.N. Pirogov Moscow Medical Institute, 6 pages (English Translation).
Stirnemann, J. et al. (Feb. 17, 2017). "A Review Of Gaucher Disease Pathophysiology, Clinical Presentation And Treatments," International Journal of Molecular Sciences 18(2):441, 30 pages.
World Health Organization (2025). "Hydroxypropylcellulose, low-substituted (Hydroxypropylcellulosum substitutum humile)," The International Pharmacopoeia [online]. 12th edition. Retrieved from Internet <URL: https://digicollections.net/phint/2025/index.html#d/b.6.1.191>, 2 pages.

* cited by examiner

METHODS FOR TREATING SYMPTOMS AND DISORDERS ASSOCIATED WITH LYSOSOMAL STORAGE DISEASES

CROSS-REFERENCE TO RELATED APPLICATIONS

This application is a U.S. National Stage Application under 35 U.S.C. § 371 of international application No. PCT/US2020/016440, which was filed on Feb. 3, 2020, which claims priority to and the benefit of U.S. Provisional Applications No. 62/800,996, filed on Feb. 4, 2019, No. 62/851,433, filed on May 22, 2019, No. 62/894,167, filed on Aug. 30, 2019, No. 62/937,618, filed on Nov. 19, 2019, and No. 62/962,647, filed on Jan. 17, 2020, the contents of each of which are hereby incorporated by reference in their entireties.

FIELD

This invention relates to methods for treating or preventing particular symptoms and disorders which are associated with lysosomal storage diseases using quinuclidine compounds of formula (I), optionally in combination with enzyme replacement therapy. Also included is pain, such as abdominal pain, and dermatological disorders, such as angiokeratoma, in a patient having a disease such as Fabry disease.

BACKGROUND

Lysosomal Storage Diseases

Lysosomal storage diseases (LSDs) are a group of about 50 rare inherited metabolic diseases caused by defects in lysosomal function. Generally, patients with an LSD accumulate harmful levels of a substrate (i.e., material stored) in lysosomes due to a deficiency or defect in an enzyme responsible for metabolizing the substrate, or due to a deficiency in an enzymatic activator required for proper enzymatic function. Most LSDs are caused by a single enzymatic defect or deficiency, usually for an enzyme involved in the metabolism of lipids or glycoproteins. Some of the more common LSDs include Gaucher disease, Fabry disease and Niemann-Pick disease (type C). Gaucher, Fabry and Niemann-Pick are examples of sphingolipidoses. Each of these diseases are associated with a constellation of symptoms which are directly or indirectly caused by the underlying genetic defects. As a result, it is often difficult to predict which symptoms or disorders associated with these can be effectively treated with different treatment methods. Symptoms which are common across several LSDs include alterations in saccadic eye movements, cognitive dysfunction, and gait disorders, such as ataxia. These symptoms are particularly common in Gaucher disease (e.g., type 3) and in Neiman-Pick disease (type C).

Fabry Disease and Skin Disorders Fabry disease is caused by a defect in the enzyme alpha-galactosidase, resulting in accumulation of globotriaosylceramide (GL-3, also known as Gb3). GL-3 accumulates in blood plasma, tissue and some organs. The disease is caused by an X-linked recessive mutation, such that males can have severe symptoms, while woman can range from being asymptomatic to moderately or severely affected. A common symptom of Fabry is full body pain or localized pain. Peripheral neuropathy, marked by Kidney complications are also common, including chronic kidney disease and kidney failure. Accumulation of sphingolipid in the heart muscle can cause cardiac hypertrophy or restrictive cardiomyopathy, as well as heart rhythm abnormalities such as tachycardia and bradycardias (including complete heart block). Skin involvement includes the formation of angiokeratomas (small, painless papules), and ocular involvement can include clouding of the corneas (vortex keratopathy) and conjunctival and retinal vascular abnormalities and cataracts.

The accumulation of GL-3 in skin and soft tissues causes the earliest symptoms of Fabry disease, including skin lesions (e.g., angiokeratomas), acroparesthesia, and hypohidrosis. See Lidove, O. et al., *Dermatological and Soft-Tissue Manifestations of Fabry Disease: Characteristics and Response to Enzyme Replacement Therapy*, Chap. 24 in FABRY DISEASE: PERSPECTIVES FROM 5 YEARS OF FOS (Mehta, A. et al. eds., Oxford PharmaGenesis 2006), available online via NCBI Bookshelf, National Library of Medicine. These symptoms often begin in childhood, many years prior to the development of severe organ damage that is characteristics of the later stages of disease. The skin includes several layers: the epidermis, dermis and hypodermis, each of which have many cell types. Fabry disease affects mainly the endothelial vessels. Endothelial cells in the superficial dermis, just below the non-vascular epidermis, are the main target of the disease. Vasa nervorum endothelial cells in the perineurium are also affected. In addition, GL-3 may accumulate in lysosomes of vascular pericytes, eccrine gland cells and dermal fibroblasts.

Angiokeratomas are benign vascular skin lesions characterized by proliferation of dilated blood vessels in the upper dermis. They occur when accumulation of GL-3 in dermal endothelial cells leads to bulging vessels and incompetence of the vessel wall, followed by secondary ectasia. These are the main cutaneous lesions found in patients with Fabry disease and may begin appearing in children between the ages of 5 and 15 years (mean age, 13.5 years. They are found in 83% of males and 80% of females with Fabry disease. Angiokeratomas spread with age to become visible on the lips, hands and toes. They may be isolated or clustered and appear as small red-to-black papules, with a smooth epidermal surface. As the disease progresses, the lesions grow, reaching a diameter of 10 mm, and become dark red to black, with a verrucous surface. Electron microscopy studies show electron-dense lysosomal inclusions in vascular endothelial cells, vascular pericytes, eccrine gland cells, dermal fibroblasts and the perineurium.

In addition to angiokeratomas, Fabry is also associated with specific polyneuropathy and sweat gland infiltration, often lead to sweating abnormalities in Fabry disease. The classic symptoms are hypohidrosis (reduced sweating) and anhidrosis (absence of sweating). These symptoms may have a significant effect on quality of life, causing fever, and heat and exercise intolerance. Hypohidrosis predisposes to acroparesthesia by making sufferers intolerant of heat and exercise. Reduced tear production by the lacrimal glands and reduced saliva production may be associated with hypohidrosis in patients with Fabry disease.

Hyperhidrosis is much less common in patients with Fabry disease than hypohidrosis and appears to be more common in females than males. It is likely that the hyperhidrosis is a manifestation of the peripheral neuropathy that occurs in Fabry disease. When cutaneous and mucous glands are affected, it may be necessary for the patient to restrict the time they spend in a warm environment or undergoing physical activity.

In patients with Fabry disease, lymphoedema appears to be related to the accumulation of glycolipids in the lymph vessels. In the absence of therapy, lymphoedema in Fabry disease can be complicated by erysipelas, with a risk of systemic infection. Severe lymphatic microangiopathy, leading to lymphoedema, has been described in Fabry disease patients. However, a study showed that severe structural and functional changes in the initial lymphatics of the skin occur in both male and female patients with Fabry disease, regardless of whether lymphoedema is manifest.

Acroparesthesia is also one of the earliest symptoms of Fabry disease. It is thought to result from ischemia of the peripheral nerves secondary to abnormalities in endothelial perineurium cells and is characterized by tingling, chronic burning or nagging pain in the hands and feet. Acute episodes of incapacitating pain, lasting from a few minutes to several days, may develop. These can occur spontaneously but may also be induced by heat, illness, stress or exercise. Fatigue, moderate fever and joint pain may be associated with these acute pain crises.

Fabry Disease and Pain

Pain is a debilitating symptom of Fabry with respect to the patient's ability to engage in the normal activities of daily life. A common symptom of Fabry is full body pain, pain localized to the extremities, or gastrointestinal pain (e.g., abdominal pain), which is thought to be due to damage to peripheral nerve endings and/or due to lipid accumulation in capillary vasculature causing painful blood flow obstruction.

Enzyme replacement therapy (ERT) is one of the only currently approved treatments for Fabry disease in the United States, with the semisynthetic enzyme agalsidase beta (alpha-galactosidase). Another enzyme, agalsidase alpha, is approved in Europe but not in the United States. In Europe, the small molecule alpha-galactosidase inhibitor migalastat (1-deoxygalactonojirimycin) is also approved for a treatment of a subset of Fabry patients. In some patients, the defect in alpha-galactosidase is caused by protein misfolding, rather than by an error in the amino acid sequence. For some of such patients, migalastat has been found to bind to the misfolded protein and cause it to reorient in the proper conformation—but only kinds of misfolding errors are amenable to this correction.

ERT thus remains the mainstay of Fabry disease treatment. ERT has not been highly effective in alleviating the pain associated with Fabry disease and additional treatment with analgesics, anticonvulsants, and nonsteroidal anti-inflammatory agents is commonly necessary. Therefore, a significant unmet need for a treatment for Fabry disease which also effectively manages the pain of Fabry disease remains.

The quinuclidine compounds described herein have activity as inhibitors of the enzyme glucosylceramide synthase (GCS). These compounds have been disclosed as generally being useful in the treatment lysosomal storage diseases such as Fabry disease, Gaucher disease and Niemann-Pick disease. See, e.g., WO 2012/129084 and U.S. 2016/0361301.

There is a real need in the art to develop therapeutics effective in alleviating or managing the pain and dermatological disorders associated with Fabry disease.

SUMMARY OF THE INVENTION

The present invention relates to a quinuclidine compound (Compound 1) according to formula (I), (I)

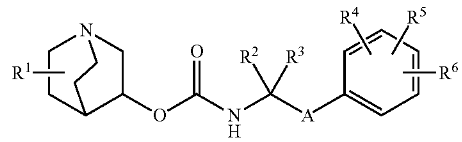

or a pharmaceutically acceptable salt or prodrug thereof, wherein:

$R^1$ is selected from hydrogen, halogen (e.g., fluorine), cyano, nitro, hydroxy, thio, amino, $C_{1-6}$-alkyl (e.g., methyl or ethyl), $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more (e.g., 1, 2 or 3) groups selected from halogen, cyano, nitro, hydroxy, thio or amino;

$R^2$ and $R^3$ are independently selected from $C_{1-3}$-alkyl, optionally substituted by one or more (e.g. 1, 2 or 3) halogens, or $R^2$ and $R^3$ together form a cyclopropyl or cyclobutyl group, optionally substituted by one or more (e.g. 1 or 2) halogens;

$R^4$, $R^5$ and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more (e.g. 1, 2 or 3) groups selected from halogen, hydroxy, cyano, and $C_{1-6}$-alkyloxy; and A is a 5- or 6-membered aryl or heteroaryl group, optionally substituted with 1, 2 or 3 groups independently selected from a halogen, hydroxy, thio, amino, nitro, $C_{1-6}$alkoxy or $C_{1-6}$alkyl.

In a first aspect, the present application provides a method for treating or preventing pain, including neuropathic pain, gastrointestinal pain (e.g., abdominal pain), and peripheral neuropathy, in a subject in need thereof, the method comprising administering to the subject an effective amount of a quinuclidine compound as described herein, e.g., a compound according to Formula I.

In other aspects, the present application further provides use of the quinuclidine compounds described herein, for the treatment or prevention of pain, including neuropathic pain, gastrointestinal pain (e.g., abdominal pain), peripheral neuropathy, and skin disorders (e.g., angiokeratoma, acroparesthesia, hypohidrosis, anhidrosis, hyperhidrosis, lymphedema, and acroparesthesia). In some embodiments, of any of these aspects, the subject in need thereof is a subject having Fabry disease, Gaucher disease, e.g., type 3, or Niemann-Pick disease Type C.

Additional features and advantages of compounds, compositions and methods disclosed herein will be apparent from the following detailed description.

DETAILED DESCRIPTION

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Definitions

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art.

All numerical designations, e.g., pH, temperature, time, concentration, molecular weight, including ranges, are approximations which are varied (+) or (−) by increments of 0.1 or 1.0, where appropriate. It is to be understood, although not always explicitly stated, that all numerical designations are preceded by the term "about". It also is to be understood, although not always explicitly stated, that the reagents described herein are merely exemplary and that equivalents of such are known in the art.

As used herein, the term "optionally substituted" is meant to be equivalent to the phrase "non-substituted or substituted by."

As used herein, the phrase "in a method of treating or preventing" (such as in the phrase "in a method of treating or preventing pain") is meant to be equivalent to the phrase "in the treatment or prevention of" (such as in the phrase "in the treatment or prevention of pain").

As used in the specification and claims, the singular form "a", "an" and "the" include plural references unless the context clearly dictates otherwise. For example, the term "a cell" includes a plurality of cells, including mixtures thereof. Unless specifically stated or obvious from context, as used herein, the term "or" is understood to be inclusive. The term "including" is used herein to mean, and is used interchangeably with, the phrase "including but not limited to".

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. Use of the term "comprising" herein is intended to encompass "consisting essentially of" and "consisting of".

A "subject," "individual" or "patient" is used interchangeably herein, and refers to a vertebrate, such as a mammal. Mammals include, but are not limited to, murines, rats, rabbit, simians, bovines, ovine, porcine, canines, felines, farm animals, sport animals, pets, equines, primates, and humans. In one embodiment, the mammals include horses, dogs, and cats. In some embodiments, the mammal is a human, e.g., a human suffering from a particular disease or disorder, such as Gaucher disease (e.g., GD-3) or Niemann-Pick disease Type C.

"Administering" is defined herein as a means of providing an agent or a composition containing the agent to a subject in a manner that results in the agent being inside the subject's body. Such an administration can be by any route including, without limitation, oral, transdermal (e.g. vagina, rectum, oral mucosa), by injection (e.g. subcutaneous, intravenous, parenterally, intraperitoneally, into the CNS), or by inhalation (e.g. oral or nasal). Pharmaceutical preparations are, of course, given by forms suitable for each administration route.

"Treating" or "treatment" of a disease generally includes: (1) inhibiting the disease, i.e. arresting or reducing the development of the disease or its clinical symptoms; and/or (2) relieving the disease, i.e. causing regression of the disease or its clinical symptoms.

"Preventing" or "prevention" of a disease generally includes causing the clinical symptoms of the disease not to develop in a patient that may be predisposed to the disease but does not yet experience or display symptoms of the disease.

The term "suffering" as it relates to the term "treatment" refers to a patient or individual who has been diagnosed with the disease. The term "suffering" as it relates to the term "prevention" refers to a patient or individual who is predisposed to the disease. A patient may also be referred to being "at risk of suffering" from a disease because of a history of disease in their family lineage or because of the presence of genetic mutations associated with the disease. A patient at risk of a disease has not yet developed all or some of the characteristic pathologies of the disease.

An "effective amount" or "therapeutically effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, and the route of administration. It is understood, however, that specific dose levels of the therapeutic agents of the present invention for any particular subject depends upon a variety of factors including, for example, the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to treat (e.g. improve) one or more symptoms associated with a disease or disorder described herein (e.g., in any of Method 2 et seq., or Method 3 et seq.) ex vivo, in vitro or in vivo.

As used herein, the term "pharmaceutically acceptable excipient" encompasses any of the standard pharmaceutical excipients, including carriers such as a phosphate buffered saline solution, water, and emulsions, such as an oil/water or water/oil emulsion, and various types of wetting agents. Pharmaceutical compositions also can include stabilizers and preservatives. For examples of carriers, stabilizers and adjuvants, see Remington's Pharmaceutical Sciences (20th ed., Mack Publishing Co. 2000).

As used herein, the term "prodrug" means a pharmacological derivative of a parent drug molecule that requires biotransformation, either spontaneous or enzymatic, within the organism to release the active drug. For example, prodrugs are variations or derivatives of the quinuclidine compounds described herein that have groups cleavable under certain metabolic conditions, which when cleaved, become the quinuclidine compounds described herein, e.g. a compound of Formula I. Such prodrugs then are pharmaceutically active in vivo when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism.

Prodrugs commonly known in the art include well-known acid derivatives, such as, for example, esters prepared by reaction of acid compounds with a suitable alcohol, amides prepared by reaction of acid compounds with an amine, and basic groups reacted to form an acylated base derivative. Other prodrug derivatives may be combined with other features disclosed herein to enhance bioavailability. As such, those of skill in the art will appreciate that certain of the presently disclosed compounds having, for example, free amino or hydroxy groups can be converted into prodrugs. Prodrugs include compounds having an amino acid residue, or a polypeptide chain of two or more (e.g. two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds having a carbonate, carbamate, amide or alkyl ester moiety covalently bonded to any of the above substituents disclosed herein.

As used herein, the term "pharmaceutically acceptable salt" means a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "$C_{1-6}$-alkyl" means a saturated linear or branched free radical consisting essentially of 1 to 6 carbon atoms and a corresponding number of hydrogen atoms. Exemplary $C_{1-6}$-alkyl groups include methyl, ethyl, n-propyl, isopropyl, n-butyl, and isobutyl. Other $C_{1-6}$-alkyl groups will be readily apparent to those of skill in the art given the benefit of the present disclosure. The terms "$C_{1-3}$-alkyl", "$C_{1-4}$-alkyl", etc., have equivalent meanings, i.e., saturated linear or branched free radical consisting essentially of 1 to 3 (or 4) carbon atoms and a corresponding number of hydrogen atoms.

As used herein, the term "$C_{2-6}$-alkenyl" means an unsaturated linear or branched free radical consisting essentially of 2 to 6 carbon atoms and a corresponding number of hydrogen atoms, which free radical comprises at least one carbon-carbon double bond. Exemplary $C_{2-6}$-alkenyl groups include ethenyl, prop-1-enyl, prop-2-enyl, isopropenyl, but-1-enyl, 2-methyl-prop-1-enyl, and 2-methyl-prop-2-enyl. Other $C_{2-6}$-alkenyl groups will be readily apparent to those of skill in the art given the benefit of the present disclosure.

As used herein, the term "$C_{2-6}$-alkynyl" means an unsaturated linear or branched free radical consisting essentially of 2 to 6 carbon atoms and a corresponding number of hydrogen atoms, which free radical comprises at least one carbon-carbon triple bond. Exemplary $C_{2-6}$-alkynyl groups include ethynyl, prop-1-ynyl, prop-2-ynyl, but-1-ynyl, and 3-methyl-but-1-ynyl. Other $C_{2-6}$-alkynyl groups will be readily apparent to those of skill in the art given the benefit of the present disclosure.

As used herein, the term "$C_{1-6}$-alkyloxy" means a saturated linear or branched free radical consisting essentially of 1 to 6 carbon atoms (and a corresponding number of hydrogen atoms) and an oxygen atom. A $C_{1-6}$-alkyloxy group is attached via the oxygen atom. Exemplary $C_{1-6}$-alkyloxy groups include methyloxy, ethyloxy, n-propyloxy, isopropyloxy, n-butyloxy, and isobutyloxy. Other $C_{1-6}$-alkyloxy groups will be readily apparent to those of skill in the art given the benefit of the present disclosure. The terms "$C_{1-3}$-alkyloxy", "$C_{1-4}$-alkyloxy", and the like, have an equivalent meaning, i.e. a saturated linear or branched free radical consisting essentially of 1 to 3 (or 4) carbon atoms (and a corresponding number of hydrogen atoms) and an oxygen atom, wherein the group is attached via the oxygen atom.

As used herein, the term "$C_{2-6}$-alkenyloxy" means an unsaturated linear or branched free radical consisting essentially of 2 to 6 carbon atoms (and a corresponding number of hydrogen atoms) and an oxygen atom, which free radical comprises at least one carbon-carbon double bond. A $C_{2-6}$-alkenyloxy group is attached via the oxygen atom. An exemplary $C_{2-6}$-alkenyloxy group is ethenyloxy; others will be readily apparent to those of skill in the art given the benefit of the present disclosure.

As used herein, the term "$C_{2-6}$-alkynyloxy" means an unsaturated linear or branched free radical consisting essentially of 2 to 6 carbon atoms (and a corresponding number of hydrogen atoms) and an oxygen atom, which free radical comprises at least one carbon-carbon triple bond. A $C_{2-6}$-alkenyloxy group is attached via the oxygen atom. An exemplary $C_{2-6}$-alkenyloxy group is ethynyloxy; others will be readily apparent to those of skill in the art given the benefit of the present disclosure.

As used herein, the term "heteroaryl" means an aromatic free radical having 5 or 6 atoms (i.e. ring atoms) that form a ring, wherein 1 to 5 of the ring atoms are carbon and the remaining 1 to 5 ring atom(s) (i.e. hetero ring atom(s)) is selected independently from the group consisting of nitrogen, sulfur, and oxygen. Exemplary 5-membered heteroaryl groups include furyl, thienyl, thiazolyl (e.g. thiazol-2-yl), pyrazolyl, isothiazolyl, oxazolyl, isoxazolyl, pyrrolyl, triazolyl, imidazolyl, oxadiazolyl and thiadiazolyl. Exemplary 6-membered heteroaryl groups include pyridyl, pyrimidyl, pyrazinyl, pyridazinyl, 1,2,4-triazinyl, benzoxazolyl, benzothiazolyl, benzisothiazolyl, benzisoxazolyl, and benzimidazolyl. Other heteroaryl groups will be readily apparent to those of skill in the art given the benefit of the present disclosure. In general, the heteroaryl group typically is attached to the main structure via a carbon atom. However, those of skill in the art will realize that certain other atoms, e.g. hetero ring atoms, can be attached to the main structure.

As used herein, the term "aryl" means an aromatic free radical having 5 or 6 atoms (i.e. ring atoms) that form a ring, wherein all of the ring atoms are carbon. An exemplary aryl group is a phenyl group.

As used herein, the term "aliphatic" means a non-aromatic compound containing carbon and hydrogen atoms, e.g. containing 1 to 9 carbon atoms. Aliphatic compounds may be straight-chained or branched, may contain one or more ring structures, and may contain one or more carbon-carbon double bonds (provided that the compound does not contain an unsaturated ring structure having aromatic character). Examples of aliphatic compounds include ethane, propylene, cyclobutane, and cyclohexadiene.

As used herein, the terms "halo" and "halogen" mean fluorine, chlorine, bromine, or iodine. These terms are used interchangeably and may refer to a halogen free radical group or to a halogen atom as such. Those of skill in the art will readily be able to ascertain the identification of which in view of the context in which this term is used in the present disclosure.

As used herein, the term "cyano" means a free radical having a carbon atom linked to a nitrogen atom via a triple bond. The cyano radical is attached via its carbon atom.

As used herein, the term "nitro" means an —$NO_2$ radical which is attached via its nitrogen atom.

As used herein, the terms "hydroxy" and "hydroxyl" mean an —OH radical which is attached via its oxygen atom. The term "thio" means an —SH radical which is attached via its sulfur atom.

As used herein, the term "amino" means a free radical having a nitrogen atom and 1 or 2 hydrogen atoms. As such, the term "amino" generally refers to primary and secondary amines. In that regard, as used herein, a tertiary amine is represented by the general formula RR'N—, wherein R and R' are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

As used herein, the term and "oxo" means an oxygen radical which is attached via a double bond. Where an atom bonded to this oxygen is a carbon atom, the bond is a carbon-oxygen double bond which may be denoted as —(C═O)— and which may be referred to as a ketone.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The following abbreviations are used herein:

br Broad signal
CDI Carbonyldiimidazole
CNS Central Nervous System
d Doublet
DAPI 4',6-diamidino-2-phenylindole
dd Doublet of doublets
DME Dimethoxyethane
DMEM Dulbecco Modified Eagle Medium
DMSO-d6 Dimethyl sulfoxide-d6
DMF Dimethylformamide
DNA Deoxyribonucleic acid
DTBZ Carbon-11 dihydrotetrabenazine
EDTA Ethylenediaminetetraacetic acid
ELISA Enzyme-linked Immunosorbent Assay
$Et_2O$ Diethyl ether
EtMgBr Ethylmagnesium bromide
EtOAc Ethyl acetate
GL1 Glucosylceramide (GlcCer)
GM1 Monosialotetrahexosylganglioside
GM3 Monosialodihexosylganglioside
GSL Glycosphingolipid
H&E Hematoxylin and eosin stain
HPLC High pressure/performance liquid chromatography
HSA Human serum albumin
IPA Isopropyl alcohol
J Coupling constant
LCMS Liquid chromatography mass spectrometry
m Multiplet
ppm Parts per million
rHA Recombinant human albumin
s Singlet
TBME Tert-Butyl Methyl Ether
THF Tetrahydrofuran
Tris Tris(hydroxymethyl)aminomethane
TWEEN20 Polysorbate 20
TWEEN80 Polysorbate 80
WT Wild type
UPLCMS Ultra performance liquid chromatography mass spectrometry Compounds The present disclosure relates to quinuclidine compounds for use in therapeutic methods relating to the treatment or prevention of the diseases and disorders discussed herein. In all of its various aspects, the invention relates to a quinuclidine compound (Compound 1) according to formula (I), (I)

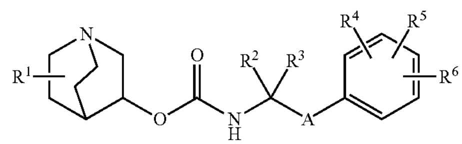

or a pharmaceutically acceptable salt or prodrug thereof, wherein:

$R^1$ is selected from hydrogen, halogen (e.g., fluorine), cyano, nitro, hydroxy, thio, amino, $C_{1-6}$-alkyl (e.g., methyl or ethyl), $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more (e.g., 1, 2 or 3) groups selected from halogen, cyano, nitro, hydroxy, thio or amino;

$R^2$ and $R^3$ are independently selected from $C_{1-3}$-alkyl, optionally substituted by one or more (e.g. 1, 2 or 3)

halogens, or $R^2$ and $R^3$ together form a cyclopropyl or cyclobutyl group, optionally substituted by one or more (e.g. 1 or 2) halogens;

$R^4$, $R^5$ and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more (e.g. 1, 2 or 3) groups selected from halogen, hydroxy, cyano, and $C_{1-6}$-alkyloxy; and A is a 5- or 6-membered aryl or heteroaryl group (e.g., phenyl or thiazolyl), optionally substituted with 1, 2 or 3 groups independently selected from halogen, hydroxy, thio, amino, nitro, $C_{1-6}$alkoxy and $C_{1-6}$alkyl.

In further embodiments of the any aspects of the present disclosure, the present disclosure further relates to Compounds as follows:

1.1 Compound 1, wherein $R^1$ is selected from hydrogen, halogen, cyano, nitro, hydroxy, thio, amino, $C_{1-6}$-alkyl, $C_{1-6}$-alkyloxy, wherein said alkyl or alkyloxy is optionally substituted with one or more (e.g., 1, 2 or 3) groups selected from halogen, cyano, nitro, hydroxy, thio or amino;

1.2 Compound 1, wherein $R^1$ is selected from hydrogen, halogen, $C_{1-6}$-alkyl, $C_{1-6}$-alkyloxy, wherein said alkyl or alkyloxy is optionally substituted with one or more (e.g., 1, 2 or 3) groups selected from halogen, cyano, nitro, hydroxy, thio or amino;

1.3 Compound 1, wherein $R^1$ is selected from hydrogen, halogen, $C_{1-4}$-alkyl, $C_{1-4}$-alkyloxy, wherein said alkyl or alkyloxy is optionally substituted with one or more (e.g., 1, 2 or 3) groups selected from halogen, cyano, nitro, hydroxy, thio or amino;

1.4 Compound 1, wherein $R^1$ is selected from hydrogen, halogen, $C_{1-4}$-alkyl, $C_{1-4}$-alkyloxy, wherein said alkyl or alkyloxy is optionally substituted with one or more (e.g., 1, 2 or 3, or 1 or 2) groups selected from cyano, nitro, hydroxy, thio or amino;

1.5 Compound 1, wherein $R^1$ is selected from hydrogen, halogen, and $C_{1-4}$-alkyl, wherein said alkyl is optionally substituted with one or more (e.g., 1 or 2) groups selected from halogen, hydroxy, thio or amino;

1.6 Compound 1, wherein $R^1$ is selected from hydrogen, fluorine, methyl and ethyl, wherein said methyl or ethyl is optionally substituted with 1 or 2 groups selected from halogen, hydroxy, thio or amino;

1.7 Compound 1, wherein $R^1$ is selected from hydrogen and methyl, wherein said methyl is optionally substituted with 1 or 2 halogens;

1.8 Compound 1, wherein $R^1$ is hydrogen;

1.9 Compound 1, or any of 1.1-1.8, wherein $R^1$ is not attached to the nitrogen atom of the quinuclidine moiety;

1.10 Compound 1, or any of 1.1-1.9, wherein $R^2$ and $R^3$ are each independently $C_{1-3}$-alkyl, optionally substituted by one or more (e.g. 1, 2 or 3) halogens;

1.11 Compound 1.11, wherein $R^2$ and $R^3$ are each independently methyl or ethyl, optionally substituted by 1 or 2 halogens;

1.12 Compound 1.11, wherein $R^2$ and $R^3$ are each independently selected from methyl and ethyl, optionally substituted by one or more fluorines, e.g., 1, 2 or 4 fluorines;

1.13 Compound 1.11, wherein $R^2$ and $R^3$ are each independently methyl substituted with 0, 1, 2 or 3 fluorines;

1.14 Compound 1.11, wherein $R^2$ and $R^3$ are each methyl or trifluoromethyl;

1.15 Compound 1.11, $R^2$ and $R^3$ are each methyl;

1.16 Compound 1, or any of 1.1-1.9, wherein $R^2$ and $R^3$ together form a cyclopropyl or cyclobutyl group, optionally substituted by one or more (e.g. 1 or 2) halogens;

1.17 Compound 1.16, wherein $R^2$ and $R^3$ together form a cyclopropyl group;

1.18 Compound 1 or any of 1.1-1.9, wherein $R^2$ and $R^3$ are each methyl or $R^2$ and $R^3$ together form a cyclopropyl group;

1.19 Compound 1, or any of 1.1-1.9, wherein $R^4$, $R^5$ and $R^6$ are each independently selected from hydrogen, halogen, $C_{1-6}$-alkyl, and $C_{1-6}$-alkyloxy, wherein said alkyl or alkyloxy is optionally substituted by one or more (e.g. 1, 2 or 3) groups selected from halogen, hydroxy, cyano, and $C_{1-6}$-alkyloxy;

1.20 Compound 1, or any of 1.1-1.9, wherein $R^4$, $R^5$ and $R^6$ are each independently selected from hydrogen, halogen, $C_{1-3}$-alkyl, and $C_{1-3}$-alkyloxy, wherein said alkyl or alkyloxy is optionally substituted by one or more (e.g. 1, 2 or 3) groups selected from halogen, hydroxy, cyano, and $C_{1-3}$-alkyloxy;

1.21 Compound 1.19, wherein $R^4$, $R^5$ and $R^6$ are each independently selected from hydrogen, halogen, $C_{1-3}$-alkyl, and $C_{1-3}$-alkyloxy, wherein said alkyl or alkyloxy is optionally substituted by one or more (e.g. 1, 2 or 3) groups selected from halogen, cyano, and $C_{1-3}$-alkyloxy;

1.22 Compound 1.19, wherein $R^4$, $R^5$ and $R^6$ are each independently selected from hydrogen, halogen, $C_{1-3}$-alkyl, and $C_{1-3}$-alkyloxy, wherein said alkyl or alkyloxy is optionally substituted by one or more (e.g. 1, 2 or 3) groups selected from halogen and $C_{1-3}$-alkyloxy;

1.23 Compound 1.19, wherein $R^4$, $R^5$ and $R^6$ are each independently selected from halogen, $C_{1-3}$-alkyl, and $C_{1-3}$-alkyloxy, wherein said alkyl or alkyloxy is optionally substituted by one or more (e.g. 1, 2 or 3) groups selected from halogen and $C_{1-3}$-alkyloxy 1.24 Compound 1, or any of 1.19-1.23, $R^4$ is selected from hydrogen, halogen, $C_{1-3}$-alkyl, and $C_{1-3}$-alkyloxy, wherein said alkyl or alkyloxy is optionally substituted by one or more (e.g. 1, 2 or 3) groups selected from halogen and $C_{1-3}$-alkyloxy;

1.25 Compound 1.24, $R^4$ is selected from halogen (e.g., fluorine), $C_{1-3}$-alkyl (e.g., methyl), and $C_{1-3}$-alkyloxy (e.g., methoxy or ethoxy), wherein said alkyl or alkyloxy is optionally substituted by one or more (e.g. 1, 2 or 3) groups selected from halogen and $C_{1-3}$-alkyloxy (e.g., methoxy or ethoxy);

1.26 Compound 1.26, $R^4$ is selected from halogen (e.g., fluorine) and $C_{1-3}$-alkyloxy (e.g., methoxy or ethoxy), wherein said alkyloxy is optionally substituted by one or more (e.g. 1, 2 or 3) groups selected from halogen and $C_{1-3}$-alkyloxy (e.g., methoxy or ethoxy);

1.27 Compound 1.26, $R^4$ is fluorine or $C_{1-3}$-alkyloxy (e.g., ethoxy), optionally substituted by one or more (e.g. 1, 2 or 3) groups selected from halogen and $C_{1-3}$-alkyloxy (e.g., methoxy);

1.28 Compound 1.26, wherein $R^4$ is fluorine or ethoxy optionally substituted by one or more (e.g. 1, 2 or 3) $C_{1-3}$-alkyloxy (e.g., methoxy);

1.29 Compound 1, or any of 1.19-1.28, wherein $R^6$ is hydrogen;

1.30 Compound 1, or any of 1.19-1.28, wherein $R^5$ and $R^6$ are each hydrogen;

1.31 Compound 1, or any of 1.19-1.28, $R^5$ and $R^6$ are each hydrogen, and $R^4$ is fluorine or $C_{1-3}$-alkyloxy (e.g., ethoxy), optionally substituted by one or more (e.g. 1, 2 or 3) groups selected from halogen and $C_{1-3}$-alkyloxy (e.g., methoxy);

1.32 Compound 1.31, wherein $R^5$ and $R^6$ are each hydrogen, and $R^4$ is fluorine or ethoxy optionally substituted by one or more (e.g. 1, 2 or 3) $C_{1-3}$-alkyloxy (e.g., methoxy);

1.33 Compound 1.32, wherein $R^5$ and $R^6$ are each hydrogen, and $R^4$ is fluorine or ethoxy substituted with methoxy (e.g., 2-methoxyethoxy);

1.34 Compound 1.32, wherein $R^4$ is fluorine or 2-methoxyethoxy;

1.35 Compound 1, or any of 1.1-1.34, wherein at least one of $R^4$, $R^5$ and $R^6$ is not hydrogen;

1.36 Compound 1, or any of 1.1-1.35, wherein $R^6$ is hydrogen, and $R^4$ and $R^5$ are positioned at the 2, 4 or 6 positions of the phenyl ring to which they are attached (i.e., ortho or para to the A substituent);

1.37 Compound 1, or any of 1.1-1.35, wherein $R^6$ is hydrogen, and $R^4$ and $R^5$ are positioned independently at the 2 and 3 (i.e., adjacent ortho and meta), 3 and 4 (i.e. adjacent meta and para), or 3 and 5 positions (i.e., meta) of the phenyl ring to which they are attached (with respect to the A substituent);

1.38 Compound 1, or any of 1.1-1.35, wherein $R^6$ is hydrogen, and $R^4$ and $R^5$ are positioned at the 3 and 5 positions (i.e., meta) of the phenyl ring to which they are attached (with respect to the A substituent);

1.39 Compound 1, or any of 1.1-1.35, wherein $R^5$ and $R^6$ are hydrogen, and $R^4$ is positioned at the 2, 3 or 4 position of the phenyl ring to which it is attached (e.g., ortho, meta or para or to the A substituent);

1.40 Compound 1, or any of 1.1-1.35, wherein $R^5$ and $R^6$ are hydrogen, and $R^4$ is positioned at the 2 or 4 position of the phenyl ring to which it is attached (e.g., ortho or para to the A substituent);

1.41 Compound 1, or any of 1.1-1.35, wherein $R^5$ and $R^6$ are hydrogen, and $R^4$ is positioned at the 4 position of the phenyl ring to which it is attached (e.g., para to the A substituent);

1.42 Compound 1, or any of 1.1-1.35, wherein none of $R^4$, $R^5$ and $R^6$ are hydrogen, and each of $R^4$, $R^5$ and $R^6$ are independently positioned at the 2, 4 or 6 positions of the phenyl ring to which they are attached (i.e., ortho or para to the A substituent);

1.43 Compound 1, or any of 1.1-1.42, wherein $R^4$ is positioned at the 4-position of the phenyl ring to which it is attached (i.e., para to the A substituent);

1.44 Compound 1, or any of 1.1-1.43, wherein A is a 6-membered aryl group, a 5-membered heteroaryl group (e.g., containing 1, 2 or 3 heteroatoms in the heteroaryl ring selected from N, O and S), or a 6-membered heteroaryl group (e.g., containing 1, 2 or 3 nitrogen atoms in the heteroaryl ring);

1.45 Compound 1.44, wherein A is a 6-membered aryl group or a 5-membered heteroaryl group (e.g., containing 1, 2 or 3 heteroatoms in the heteroaryl ring selected from N, O and S), optionally wherein the 5-membered heteroaryl group contains 1 or 2 heteroatoms selected from N and S (e.g., one N and/or one S);

1.46 Compound 1.44 or 1.45, wherein A is selected from the group consisting of phenyl, furyl, thienyl, thiazolyl, pyrazolyl, isothiazolyl, oxazolyl, isoxazolyl, pyrrolyl, triazolyl, imidazolyl, oxadiazolyl and thiadiazolyl;

1.47 Compound 1.46, wherein A is selected from the group consisting of phenyl, thienyl, thiazolyl, pyrrolyl, and imidazolyl;

1.48 Compound 1.46, wherein A is selected from the group consisting of phenyl and thiazolyl, e.g., 2-thiazol-4-yl or 4-thiazol-2-yl;

1.49 Compound 1, or any of 1.1-1.48, wherein A is unsubstituted 1.50 Compound 1, or any of 1.1-1.48, wherein A is substituted with one or more (e.g., 1, 2 or 3) groups independently selected from a halogen, hydroxy, thio, amino, nitro, $C_{1-6}$alkoxy and $C_{1-6}$alkyl (e.g., methyl);

1.51 Compound 1.50, wherein A is thiazolyl substituted with one halogen (e.g., fluorine), or $C_{1-6}$alkyl (e.g., methyl);

1.52 Compound 1.50, wherein A is phenyl substituted with 1, 2 or 3 groups independently selected from halogen (e.g., fluorine) and $C_{1-6}$alkyl (e.g., methyl);

1.53 Compound 1.52, wherein A is phenyl substituted with 1 or 2 fluorines or methyl groups;

1.54 Compound 1, or any of 1.1-1.53 wherein the two groups attached to the A substituent (i.e., the phenyl ring (—($C_6H_2R^4R^5R^6$)) and the —C($R^2R^3$)— group) are positioned in a 1,2-, 1,3- or 1,4-relationship to each other (i.e., ortho, meta, or para);

1.55 Compound 1.54, wherein the two groups attached to the A substituent are positioned in a 1,3-relationship to each other (i.e., meta);

1.56 Compound 1.54, wherein the two groups attached to the A substituent are positioned in a 1,4-relationship to each other (i.e., para);

1.57 Any of Compounds 1.54 to 1.56, wherein the A substituent is a 5-membered heteroaryl group and at least one of the two groups attached to the A substituent (i.e., the phenyl ring (—($C_6H_2R^4R^5R^6$)) or the —C($R^2R^3$)— group) is attached to a carbon atom of the heteroaryl ring, optionally wherein both of such groups are attached to carbon atoms of the heteroaryl ring;

1.58 Compound 1, or any of 1.1-1.57, wherein the Compound of Formula I can be represented by any one or more of the following substructures:

(II)

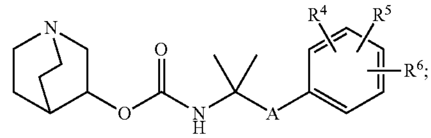

(III)

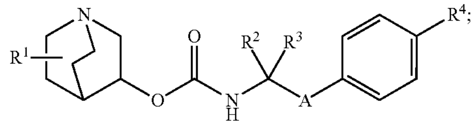

(IV)

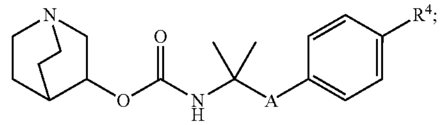

(V)

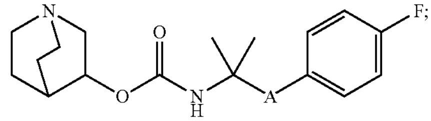

-continued (VI)

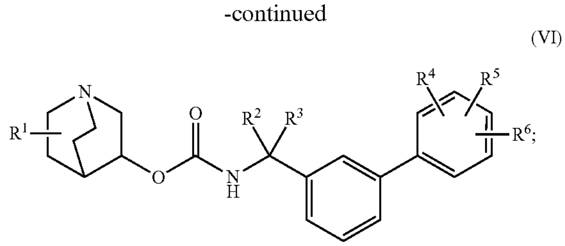

(VII)

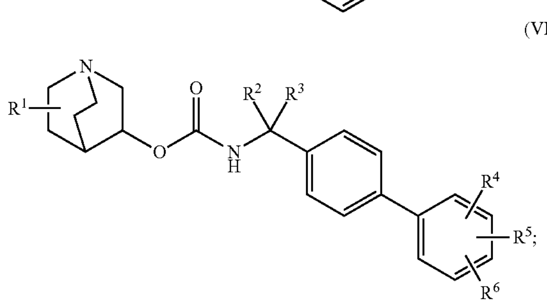

(VIII)

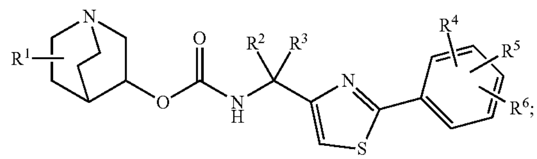

(IX)

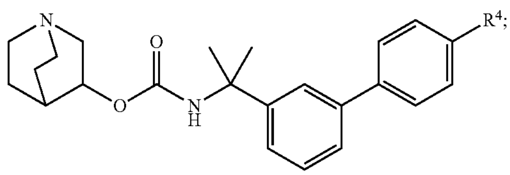

(X)

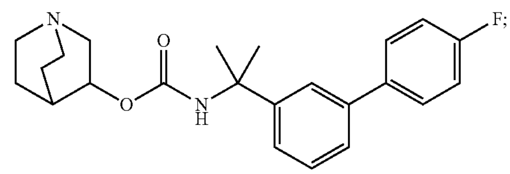

(XI)

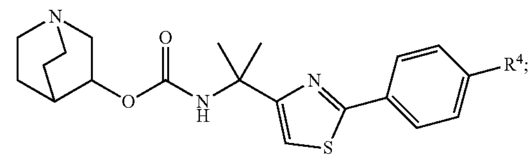

(XII)

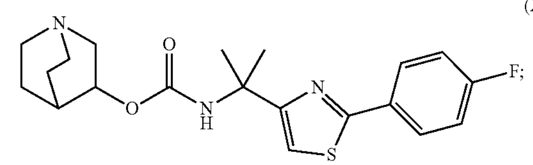

1.59 Compound 1, or any of 1.1-1.58, wherein the compound of Formula I, or any of Formulas II to XII, has the (S) configuration;

1.60 Compound 1, or any of 1.1-1.58, wherein the compound of Formula I, or any of Formulas II to XII, has the (R) configuration;

1.61 Compound 1, or any of 1.1-1.60, wherein the compound of Formula I, or any of Formulas II to XII, has an enantiomeric excess (e.g., of the (S) configuration) of at least 90%, e.g., at least 92%, 94%, 95%, 96%, 97%, 98%, 99%, 99.5% or 99.9%;

1.62 Compound 1, or any of 1.1-1.58, wherein the compound of Formula I, or any of Formulas II to XII, is racemic (i.e., approximately a 50:50 ratio of enantiomers), or is a mixture of enantiomers of some other ratio (e.g., less than 50:50 or greater than 50:50);

1.63 Compound 1, or any of 1.1-1.62, wherein the Compound of Formula I is selected from the group consisting of:

| Compound No. | Compound |
|---|---|
| 1 | Quinuclidin-3-yl (2-(4'-fluoro-[1,1'-biphenyl]-3-yl)propan-2-yl)carbamate |
| 2 | (S)-quinuclidin-3-yl (2-(2-(4-fluorophenyl)thiazol-4-yl)propan-2-yl)carbamate |
| 3 | (S)-quinuclidin-3-yl (2-(4'-(2-methoxyethoxy)-[1,1'-biphenyl]-4-yl)propan-2-yl)carbamate |
| 4 | 1-azabicyclo[2.2.2]oct-3-yl [2-(biphenyl-3-yl)propan-2-yl]carbamate |
| 5 | (S)-quinuclidin-3-yl 2-(biphenyl-4-yl)propan-2-ylcarbamate |
| 6 | Quinuclidin-3-yl 1-(biphenyl-4-yl)cyclopropylcarbamate |
| 7 | (S)-quinuclidin-3-yl 1-(4'-fluorobiphenyl-4-yl)cyclopropylcarbamate |
| 8 | (S)-1-azabicyclo[2.2.2]oct-3-yl [1-(2',4'-difluorobiphenyl-4-yl)cyclopropyl]carbamate |
| 9 | 1-azabicyclo[2.2.2]oct-3-yl [1-(4'-methoxybiphenyl-4-yl)cyclopropyl]carbamate |
| 10 | Quinuclidin-3-yl 2-(5-(4-fluorophenyl)thiophen-3-yl)propan-2-ylcarbamate |
| 11 | (S)-quinuclidin-3-yl 2-(3-(4-fluorophenyl)isothiazol-5-yl)propan-2-ylcarbamate |
| 12 | (S)-quinuclidin-3-yl 2-(4-(4-fluorophenyl)thiazol-2-yl)propan-2-ylcarbamate |
| 13 | Quinuclidin-3-yl (2-(4'-(2-methoxyethoxy)-[1,1'-biphenyl]-4-yl)propan-2-yl)carbamate |
| 14 | (S)-quinuclidin-3-yl (2-(3'-(2-methoxyethoxy)-[1,1'-biphenyl]-4-yl)propan-2-yl)carbamate |
| 15 | Quinuclidin-3-yl (2-(4'-(2-methoxyethoxy)-[1,1'-biphenyl]-3-yl)propan-2-yl)carbamate |
| 16 | Quinuclidin-3-yl (2-(4'-(3-methoxypropoxy)-[1,1'-biphenyl]-4-yl)propan-2-yl)carbamate |
| 17 | Quinuclidin-3-yl (2-(4'-(hydroxymethyl)-[1,1'-biphenyl]-4-yl)propan-2-yl)carbamate |
| 18 | Quinuclidin-3-yl (2-(4'-(2-hydroxyethyl)-[1,1'-biphenyl]-4-yl)propan-2-yl)carbamate |
| 19 | Quinuclidin-3-yl (2-(2-(4-(3-methoxypropoxy)phenyl)thiazol-4-yl)propan-2-yl)carbamate |
| 20 | Quinuclidin-3-yl (2-(2-(4-(2-methoxyethoxy)phenyl)thiazol-4-yl)propan-2-yl)carbamate |
| 21 | Quinuclidin-3-yl 2-(5-(4-(2-methoxyethoxy)phenyl)pyridin-2-yl)propan-2-ylcarbamate |
| 22 | Quinuclidin-3-yl (2-(4'-(-cyanopropoxy)-[1,1'-biphenyl]-4-yl)propan-2-yl)carbamate |
| 23 | Quinuclidin-3-yl (2-(4'-(cyanomethoxy)-[1,1'-biphenyl]-4-yl)propan-2-yl)carbamate |

1.64 Compound 1, or any of 1.1-1.63, wherein the compound is selected from quinuclidin-3-yl (2-(4'-fluoro-[11,1'-biphenyl]-3-yl)propan-2-yl)carbamate, (S)-quinuclidin-3-yl (2-(2-(4-fluorophenyl)thiazol-4-yl)propan-2-yl)carbamate, and (S)-quinuclidin-3-yl (2-(4'-(2-methoxyethoxy)-[1,1'-biphenyl]-4-yl)propan-2-yl)carbamate;

1.65 Compound 1, or any of 1.1-1.63, wherein the compound is quinuclidin-3-yl (2-(4'-fluoro-[1,1'-biphenyl]-3-yl)propan-2-yl)carbamate;

1.66 Compound 1 or any of 1.1-1.63, wherein the compound is quinuclidin-3-yl (2-(2-(4-fluorophenyl)thiazol-4-yl)propan-2-yl)carbamate, e.g., (S)-quinuclidin-3-yl (2-(2-(4-fluorophenyl)thiazol-4-yl)propan-2-yl) carbamate;

1.67 Compound 1, or any of 1.1-1.66, wherein the Compound of Formula I, or any of II to XII, is in free base form;

1.68 Compound 1, or any of 1.1-1.66, wherein the Compound of Formula I, or any of II to XII, is in pharmaceutically acceptable salt form;

1.69 Compound 1.68, wherein said salt form is an acid addition salt form;

1.70 Compound 1.69, wherein said acid addition salt form is a salt selected from the hydrochloride, hydrobromide, hydroiodide, nitrate, sulfate, bisulfate, phosphate, acid phosphate, acetate, lactate, citrate, acid citrate, tartrate, bitartrate, succinate, hydroxysuccincate, malate, maleate, fumarate, gluconate, saccharate, benzoate, methanesulfonate, and pamoate;

1.71 Compound 1.70, wherein the acid addition salt form is selected from hydrochloride, hydroxysuccinate (e.g., 2-hydroxysuccinate), and malate;

1.72 Compound 1.68, wherein said salt form is a base addition salt form;

1.73 Compound 1, or any of 1.1-1.72, wherein the compound is (S)-quinuclidin-3-yl (2-(2-(4-fluorophenyl) thiazol-4-yl)propan-2-yl)carbamate in malate salt form;

1.74 Compound 1, or any of 1.1-1.73, wherein the Compound of Formula I, or any of II to XII, is in the form of a prodrug, as described herein;

1.75 Compound 1, or any of 1.1-1.74, wherein the Compound of Formula I, or any of II to XII, is in the form of a hydrate, solvate and/or polymorph.

Salts

Presently disclosed compounds, e.g., any of Compounds 1 or 1.1-1.75, that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g. by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained. Presently disclosed compounds that are positively charged, e.g. containing a quaternary ammonium, may also form salts with the anionic component of various inorganic and/or organic acids.

Acids which can be used to prepare pharmaceutically acceptable salts of quinuclidine compounds are those which can form non-toxic acid addition salts, e.g. salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, malate, maleate, fumarate, gluconate, saccharate, benzoate, methanesulfonate and pamoate [i.e. 1,1'-methylene-bis-(2-hydroxy-3-naphthoate)] salts.

Presently disclosed compounds that are acidic in nature, e.g. compounds containing a thiol moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g. by treating the corresponding acidic compounds with an aqueous solution containing the desired pharmacologically acceptable cations, and then evaporating the resulting solution to dryness, e.g. under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents may be employed in order to ensure completeness of reaction and maximum product yields of the desired solid salt.

Bases which can be used to prepare the pharmaceutically acceptable base addition salts of quinuclidine compounds are those which can form non-toxic base addition salts, e.g. salts containing pharmacologically acceptable cations, such as, alkali metal cations (e.g. potassium and sodium), alkaline earth metal cations (e.g. calcium and magnesium), ammonium or other water-soluble amine addition salts such as N-methylglucamine (meglumine), lower alkanolammonium, and other such bases of organic amines.

In one embodiment, the pharmaceutically acceptable salt is a succinate salt. In another embodiment, the pharmaceutically acceptable salt is a 2-hydroxysuccinate salt, e.g. an (S)-2-hydroxysuccinate salt. In another embodiment, the pharmaceutically acceptable salt is a hydrochloride salt (i.e. a salt with HCl). In another embodiment, the pharmaceutically acceptable salt is a malate salt.

Prodrugs

The present disclosure further embraces prodrugs of the compounds 1 and 1.1-1.75. The pharmaceutically acceptable prodrugs disclosed herein are derivatives of quinuclidine compounds which can be converted in vivo into the quinuclidine compounds described herein. The prodrugs, which may themselves have some activity, become pharmaceutically active in vivo when they undergo, for example, solvolysis under physiological conditions or enzymatic degradation. Methods for preparing prodrugs of compounds as described herein would be apparent to one of skill in the art based on the present disclosure.

In one embodiment, the carbamate moiety of the quinuclidine compound is modified. For example, the carbamate moiety of the quinuclidine compound may be modified by the addition of water and/or one or two aliphatic alcohols. In this case, the carbon-oxygen double bond of the carbamate moiety adopts what could be considered a hemiacetal or acetal functionality. In one embodiment, the carbamate moiety of the quinuclidine compound may be modified by the addition of an aliphatic diol such as 1,2-ethanediol.

In one embodiment, one or more of the hydroxy, thio or amino groups on the quinuclidine compound are modified. For example, one or more of the hydroxy, thio and/or amino groups on the quinuclidine compound may be modified to form acid derivatives, e.g. esters, thioesters (or thiolesters) and/or amides. The acid derivatives can be formed, for example, by reacting a quinuclidine compound which comprises one or more hydroxy, thio or amino groups with an acetylating agent. Examples of acetylating agents include anhydrides such as acetic anhydride, acid chlorides such as benzyl chloride, and dicarbonates such as di-tert-butyl dicarbonate.

Stereochemistry

The present disclosure further embraces stereoisomers and mixture of stereoisomers of compounds 1 and 1.1-1.75.

Stereoisomers (e.g. cis and trans isomers) and all optical isomers of a presently disclosed compound (e.g. R- and S-enantiomers), as well as racemic, diastereomeric and other mixtures of such isomers are within the scope of the present disclosure.

In one embodiment, the quinuclidin-3-yl group of a quinuclidine compound as defined herein has the R-configuration. Accordingly, the quinuclidine compound may be selected from the group consisting of compounds of formulae (Ia) to (XIIa):

(Ia)

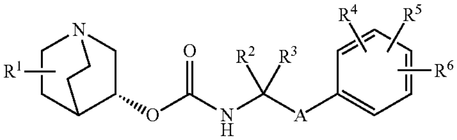

(IIa)

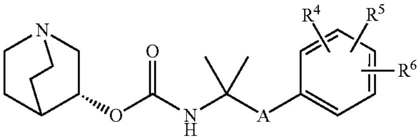

(IIIa)

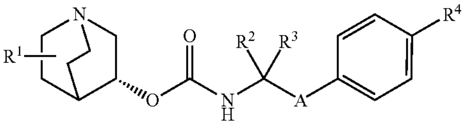

(IVa)

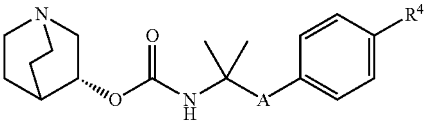

(Va)

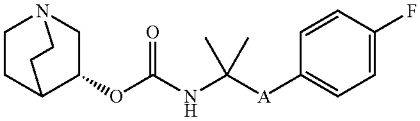

(VIa)

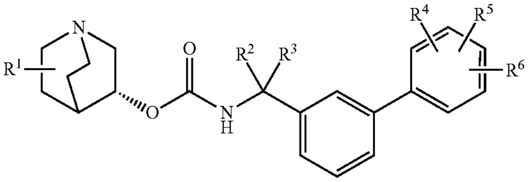

(VIIa)

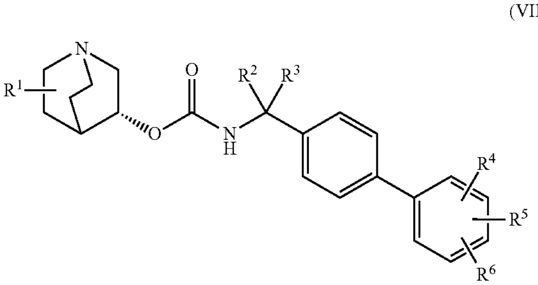

-continued (VIIIa)

(IXa)

(Xa)

(XIa)

(XIIa)

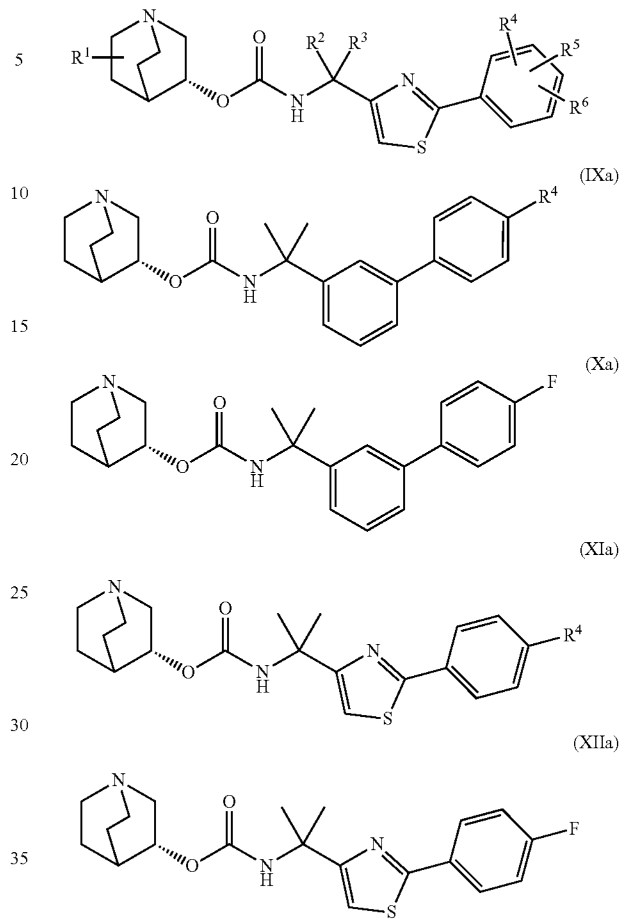

and the pharmaceutically acceptable salts and prodrugs thereof.

In another embodiment, the quinuclidin-3-yl group of the quinuclidine compound as defined herein has the S-configuration. Accordingly, the quinuclidine compound may be selected from the group consisting of compounds of formulae (Ib) to (XIIb):

(Ib)

(IIb)

(IIIb)

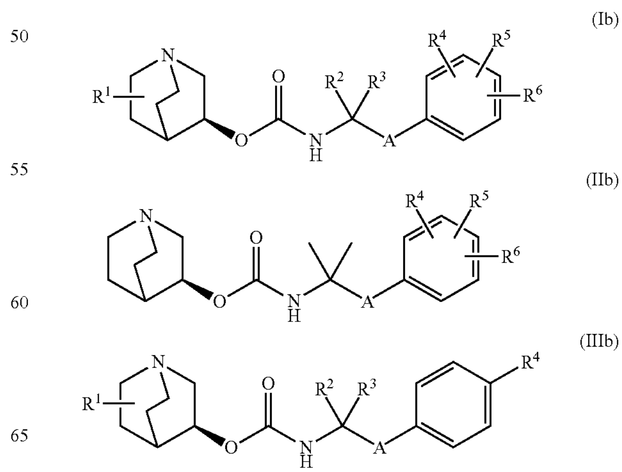

-continued (IVb)

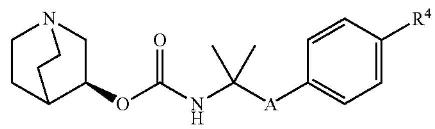

(Vb)

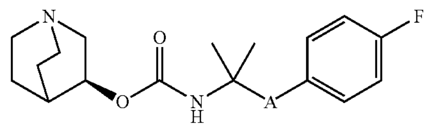

(VIb)

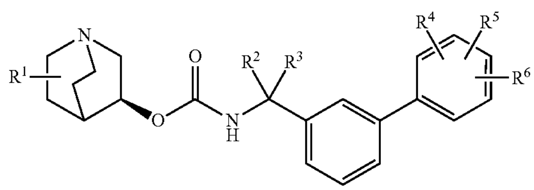

(VIIb)

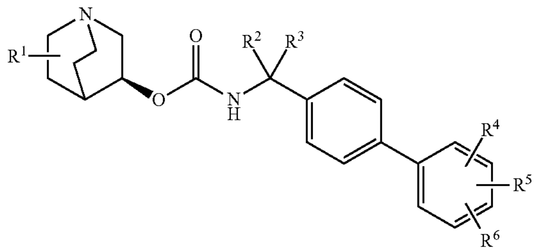

(VIIIb)

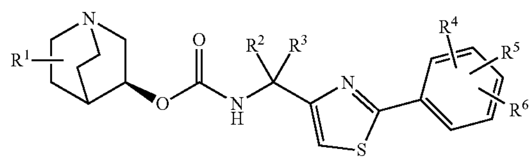

(IXb)

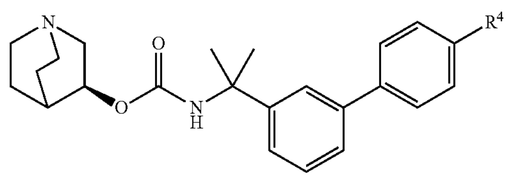

(Xb)

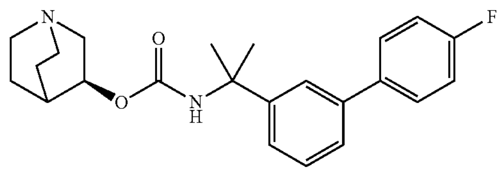

(XIb)

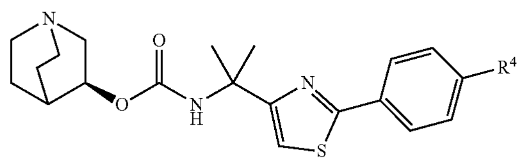

-continued (XIIb)

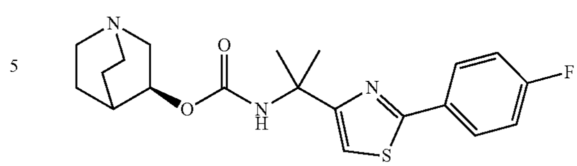

and the pharmaceutically acceptable salts and prodrugs thereof.

In one embodiment the quinuclidine compound is a compound of formula (Xb) or a pharmaceutically acceptable salt or prodrug thereof. In another embodiment the quinuclidine compound is a compound of formula (XIIb) or a pharmaceutically acceptable salt or prodrug thereof.

In one embodiment, the quinuclidin-3-yl group of the quinuclidine compound as defined herein exists in a mixture of isomers having the R- and S-configurations. For example, the quinuclidine compound may be a mixture of compounds selected from the group consisting of compounds of formulae (Ia) and (Ib), (IIa) and (IIb), (IIIa) and (IIIb), (IVa) and (IVb), (Va) and (Vb), (VIa) and (VIb), (VIIa) and (VIIb), (VIIIa) and (VIIIb), (IXa) and (IXb), (Xa) and (Xb), (XIa) and (XIb), and (XIIa) and (XIIb), and the pharmaceutically acceptable salts and prodrugs thereof. In one embodiment the quinuclidine compound is present as a racemic mixture, e.g. the R- and S-isomers of the quinuclidin-3-yl group are present in about equal amounts. In another embodiment the quinuclidine compound is present as a mixture of isomers having the R- and S-configurations, wherein the R- and S-isomers are present in different amounts. In one embodiment the S-isomer is present in an enantiomeric excess of at least about 5%, 10%, 25%, 40%, 70%, 80%, 90%, 95%, 97%, 98% or 99%, e.g. about 100%. In another embodiment, the R-isomer is present in an enantiomeric excess of at least about 5%, 10%, 25%, 40%, 70%, 80%, 90%, 95%, 97%, 98% or 99%, e.g. about 100%.

Methods for preparing enantioenriched and/or enantiopure quinuclidine compounds would be apparent to the person of skill in the art based on the present disclosure.

The compounds presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

Other Forms

The present disclosure further embraces hydrates, solvates and polymorphs of Compound 1 and 1.1-1.75. Pharmaceutically acceptable hydrates, solvates, and polymorphs, of the quinuclidine compounds described herein are within the scope of the present disclosure. Quinuclidine compounds as described herein may be in an amorphous form and/or in one or more crystalline forms.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$ $^{32}P$, $^{35}S$, $^{18}F$, and $^{36}Cl$, respectively.

Medical Indications

The quinuclidine compounds, and pharmaceutical compositions containing them, described herein are useful in therapy, in particular in the therapeutic treatment of pain, including neuropathic pain, gastrointestinal pain (e.g., abdominal pain), and peripheral neuropathy, and dermatological disorders, such as angiokeratoma, in a patient having a disease such as Fabry disease. Subjects to be treated according to the methods described herein include vertebrates, In a first aspect, the present invention provides a method (Method 2) for treating or preventing pain, including neuropathic pain, gastrointestinal pain (e.g., abdominal pain), and peripheral neuropathy, in a subject in need thereof, the method comprising administering to the subject an effective amount of a quinuclidine compound as described herein, e.g., a compound according to Formula I or any of II-XII, Ia-XIIa or Ib-XIIb, or any of Compounds 1 or 1.1 to 1.75. Also provided is a quinuclidine compound as described herein, e.g., a compound according to Formula I or any of II-XII, Ia-XIIa or Ib-XIIb, or any of Compounds 1 or 1.1 to 1.75, for use in a method of treating or preventing pain, including neuropathic pain, gastrointestinal pain (e.g., abdominal pain), and peripheral neuropathy, in a subject in need thereof, e.g., for use in Method 2 or any of 2.1-2.51. Further provided is the use of a quinuclidine compound as described herein, e.g., a compound according to Formula I or any of II-XII, Ia-XIIa or Ib-XIIb, or any of Compounds 1 or 1.1 to 1.75, in the manufacture of a medicament for use in a method of treating or preventing pain, including neuropathic pain, gastrointestinal pain (e.g., abdominal pain), and peripheral neuropathy, in a subject in need thereof, e.g., in the manufacture of a medicament for use in Method 2 or any of 2.1-2.51.

In particular further embodiments of Method 2, the present disclosure provides:

2.1.Method 2, wherein the method comprises administering to the subject an effective amount of a compound according to Formula I or any of II-XII, Ia-XIIa or Ib-XIIb, or any of Compounds 1 or any of 1.1 to 1.75;

2.2.Method 2, wherein the method comprises administering to the subject an effective amount of Compound 1 or any one or more of Compounds 1.1 to 1.75;

2.3.Method 2 or any of 2.1-2.2, wherein the method comprises administering to the subject an effective amount of a pharmaceutical composition comprising the compound according to Formula I or any of II-XII, Ia-XIIa or Ib-XIIb, or any of Compounds 1 or any of 1.1 to 1.75;

2.4.Method 2 or any of 2.1-2.2, wherein the method comprises administering to the subject an effective amount of a pharmaceutical composition comprising the Compound 1 or any one or more of Compounds 1.1 to 1.75;

2.5.Method 2.3 or 2.4, wherein the pharmaceutical composition further comprises at least one pharmaceutically acceptable excipient, as described herein;

2.6.Method 2 or any of 2.1-2.5, wherein the method comprising administering a pharmaceutical dosage form comprising an effective amount of the compound or an effective amount of the pharmaceutical composition;

2.7.Method 2.6, wherein the dosage form is an oral dosage form (e.g., a pill, capsule, caplet, tablet, dragee, powder, granule, film, lozenge, or liquid);

2.8.Method 2.7, wherein the dosage form is a chewable tablet;

2.9.Method 2.6, wherein the dosage form is a parenteral dosage form (e.g., wherein the pharmaceutical composition is formulated for injection);

2.10. Method 2.9, wherein the injection is intravenous, intramuscular, intrathecal or subcutaneous injection, optionally a sterile injection;

2.11. Method 2.6, wherein the dosage form is a topical or rectal dosage form;

2.12. Method 2.6, wherein the dosage form is an intranasal dosage form (e.g., an aerosol);

2.13. Method 2 or any of 2.1 to 2.12, wherein the method further comprises concurrently administering a second active agent, e.g., a second compound capable of treating or preventing pain in a patient in need thereof, as described herein;

2.14. Method 2.13, wherein the second active agent is administrated in the same pharmaceutical composition or dosage form as the quinuclidine compound;

2.15. Method 2.13 or 2.14, wherein the second active agent is a galactosidase inhibitor (e.g., an alpha-galactosidase inhibitor, such as migalastat);

2.16. Method 2, or any of 2.1-2.15, wherein the subject is a mammalian animal;

2.17. Method 2.16, wherein the subject is a primate animal;

2.18. Method 2.17, wherein the subject is a human;

2.19. Method 2 or any of 2.1-2.18, wherein the pain is a peripheral pain, such as peripheral neuropathy;

2.20. Method 2 or any of 2.1-2.18, wherein the pain is gastrointestinal pain (e.g., abdominal pain);

2.21. Method 2, or any of 2.1-2.18, wherein the pain is full body pain;

2.22. Method 2, or any of 2.1-2.21, wherein the pain is resistant to or not fully alleviated by treatment with analgesics;

2.23. Method 2, or any of 2.1-2.21, wherein the pain is resistant to or not fully alleviated by treatment with non-steroidal anti-inflammatory agents;

2.24. Method 2, or any of 2.1-2.23, wherein the subject has Fabry disease;

2.25. Method 2.24, wherein the Fabry disease is not amenable to treatment with migalastat;

2.26. Method 2, or any of 2.1-2.25, wherein the subject has severely deficient or absent alpha-galactosidase activity (e.g., <1% of normal, e.g., as measured in circulating leukocytes);

2.27. Method 2, or any of 2.1-2.25, wherein the subject is diagnosed with a mutation in the gene GLA (e.g., a hemizygous male, a homozygous female or a heterozygous female), optionally wherein the mutation is a nonsense codon in the GLA gene;

2.28. Method 2, or any of 2.1-2.27, wherein the subject has marked accumulation of GL-3 in tissues (e.g., in skin capillary endothelial cells or in plasma);

2.29. Method 2, or any of 2.1-2.28, wherein the subject undergoes concurrent treatment with enzyme replacement therapy (ERT), e.g., using agalsidase alpha or agalsidase beta;

2.30. Method 2, or any of 2.1-2.28, wherein the subject undergoes concurrent treatment with an alpha-galactosidase inhibitor (e.g., migalastat);

2.31. Method 2, or any of 2.1-2.30, wherein the subject has a glucosylceramide (GL1) concentration in plasma of at least 2 μg/mL, e.g., at least 3 μg/mL, or at least 4 μg/mL in plasma;

2.32. Method 2, or any of 2.1-2.31, wherein the subject has a glucosylsphingosine (lyso-GL1) concentration in plasma of at least 65 ng/mL, e.g., at least 70 ng/mL, or at least 80 ng/mL, in plasma;

2.33. Method 2, or any of 2.1-2.32, wherein the subject has a GL3 concentration in plasma of at least 4 μg/mL, e.g., at least 6 μg/mL, or at least 8 μg/mL in plasma;

2.34. Method 2, or any of 2.1-2.33, wherein the subject is administered a daily dose of about 1 mg to about 150 mg of the compound according to Formula I (or any of II-XII, Ia-XIIa or Ib-XIIb, or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

2.35. Method 2, or any of 2.1-2.34, wherein the subject is a human adult patient, e.g., of an age from 18 to 80 years old, e.g., from 18 to 60 years old, or from 18 to 40 years old, or from 18 to 30 years old, or from 18 to 25 years old;

2.36. Method 2, or any of 2.1-2.34, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

2.37. Method 2, or any of 2.1-2.36, wherein the method results in reduction in GL-1 concentration in plasma of at least 30% after 2 weeks or 4 weeks or 8 weeks of treatment, e.g., at least 40%, at least 50%, or at least 60%;

2.38. Method 2, or any of 2.1-2.37, wherein the method results in reduction in GL-3 concentration in plasma of at least 20% after 2 weeks or 4 weeks or 8 weeks of treatment, e.g., at least 30%, at least 40%, or at least 50%;

2.39. Method 2, or any of 2.1-2.38, wherein the method results in reduction in GL-3 concentration in plasma of at least 40% after 26 weeks or 52 weeks or 104 weeks, e.g., at least 50%, at least 60% or at least 70%;

2.40. Method 2, or any of 2.1-2.39, wherein the method results in reduction in lyso-GL-3 concentration in plasma of at least 25% after 18 weeks or 26 weeks or 52 weeks, e.g., at least 35%, at least 45% or at least 50%;

2.41. Method 2, or any of 2.1-2.39, wherein the method results in reduction in GM3 concentration in plasma of at least 25% after 2 weeks or 4 weeks or 8 weeks, e.g., at least 30%, at least 40% or at least 50%;

2.42. Method 2, or any of 2.1-2.39, wherein the method results in a reduction in severity of pain (e.g., in bodily pain and/or gastrointestinal pain (e.g., abdominal pain)) within 26 weeks or 52 weeks or 156 weeks;

2.43. Method 2, or any of 2.1-2.39, wherein the method results in reduction in GL-3 levels in skin (e.g., skin capillary endothelial cells) within 26 weeks or 52 weeks or 156 weeks, e.g., as shown by the extent of GL-3 inclusions;

2.44. Method 2, or any of 2.1-2.43, wherein the compound according to Formula I (or any of II-XII, Ia-XIIa or Ib-XIIb, or any of Compounds 1 or 1.1 to 1.75), or pharmaceutically acceptable salt or prodrug thereof, is administered by systemic administration, e.g., via a parenteral route or a non-parenteral route;

2.45. Method 2.44, wherein the route of administration is oral (enteral);

2.46. Method 2.44, wherein the route of administration is parenteral, e.g., by injection, such as, by intravenous injection;

2.47. Method 2, or any of 2.1-2.46, wherein the compound according to Formula I (or any of II-XII, Ia-XIIa or Ib-XIIb, or any of Compounds 1 or 1.1 to 1.75), or pharmaceutically acceptable salt or prodrug thereof, is administered by local administration, e.g., by topical administration;

2.48. Method 2, or any of 2.1-2.49, wherein the compound is (S)-quinuclidin-3-yl (2-(2-(4-fluorophenyl) thiazol-4-yl)propan-2-yl)carbamate or quinuclidin-3-yl (2-(4'-fluoro-[1,1'-biphenyl]-3-yl)propan-2-yl)carbamate;

2.49. Method 2.48, wherein the dosage of the compound is 15 mg/day orally administered;

2.50. Method 2.49, wherein the dosage of the compound is 15 mg/day in a single oral dose;

2.51. Method 2, or any of 2.1-2.50, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

In a second aspect, the present invention provides a method (Method 3) for treating or preventing dermatological disorders caused by GL-3 accumulation, including angiokeratoma, hypohidrosis, anhidrosis, hyperhidrosis, lymphedema, and/or acroparesthesia, in a subject in need thereof, the method comprising administering to the subject an effective amount of a quinuclidine compound as described herein, e.g., a compound according to Formula I or any of II-XII, Ia-XIIa or Ib-XIIb, or any of Compounds 1 or 1.1 to 1.75. Also provided is a quinuclidine compound as described herein, e.g., a compound according to Formula I or any of II-XII, Ia-XIIa or Ib-XIIb, or any of Compounds 1 or 1.1 to 1.75, for use in a method of treating or preventing dermatological disorders caused by GL-3 accumulation, including angiokeratoma, hypohidrosis, anhidrosis, hyperhidrosis, lymphedema, and/or acroparesthesia, in a subject in need thereof, e.g., for use in Method 3 or any of 3.1-3.53.

Further provided is the use of a quinuclidine compound as described herein, e.g., a compound according to Formula I or any of II-XII, Ia-XIIa or Ib-XIIb, or any of Compounds 1 or 1.1 to 1.75, in the manufacture of a medicament for use in a method of treating or preventing dermatological disorders caused by GL-3 accumulation, including angiokeratoma, hypohidrosis, anhidrosis, hyperhidrosis, lymphedema, and/or acroparesthesia, in a subject in need thereof, e.g., in the manufacture of a medicament for use in Method 3 or any of 3.1-3.53.

In particular further embodiments of Method 3, the present disclosure provides:

3.1. Method 3, wherein the method comprises administering to the subject an effective amount of a compound according to Formula I or any of II-XII, Ia-XIIa or Ib-XIIb, or any of Compounds 1 or any of 1.1 to 1.75;

3.2. Method 3, wherein the method comprises administering to the subject an effective amount of Compound 1 or any one or more of Compounds 1.1 to 1.75;

3.3. Method 3 or any of 3.1-3.2, wherein the method comprises administering to the subject an effective amount of a pharmaceutical composition comprising the compound according to Formula I or any of II-XII, Ia-XIIa or Ib-XIIb, or any of Compounds 1 or any of 1.1 to 1.75;

3.4. Method 3 or any of 3.1-3.2, wherein the method comprises administering to the subject an effective amount of a pharmaceutical composition comprising the Compound 1 or any one or more of Compounds 1.1 to 1.75;

3.5. Method 3.3 or 3.4, wherein the pharmaceutical composition further comprises at least one pharmaceutically acceptable excipient, as described herein;

3.6. Method 3 or any of 3.1-3.5, wherein the method comprising administering a pharmaceutical dosage form comprising an effective amount of the compound or an effective amount of the pharmaceutical composition;

3.7. Method 3.6, wherein the dosage form is an oral dosage form (e.g., a pill, capsule, caplet, tablet, dragee, powder, granule, film, lozenge, or liquid);

3.8. Method 3.7, wherein the dosage form is a chewable tablet;

3.9. Method 3.6, wherein the dosage form is a parenteral dosage form (e.g., wherein the pharmaceutical composition is formulated for injection);

3.10. Method 3.9, wherein the injection is intravenous, intramuscular, intrathecal or subcutaneous injection, optionally a sterile injection;

3.11. Method 3.6, wherein the dosage form is a topical or rectal dosage form;

3.12. Method 3.6, wherein the dosage form is an intranasal dosage form (e.g., an aerosol);

3.13. Method 3 or any of 3.1 to 3.12, wherein the method further comprises concurrently administering a second active agent, e.g., a second compound capable of treating or preventing pain in a patient in need thereof, as described herein;

3.14. Method 3.13, wherein the second active agent is administrated in the same pharmaceutical composition or dosage form as the quinuclidine compound;

3.15. Method 3.13 or 3.14, wherein the second active agent is a galactosidase inhibitor (e.g., an alpha-galactosidase inhibitor, such as migalastat);

3.16. Method 3, or any of 3.1-3.15, wherein the subject is a mammalian animal;

3.17. Method 3.16, wherein the subject is a primate animal;

3.18. Method 3.17, wherein the subject is a human;

3.19. Method 3 or any of 3.1-3.18, wherein the dermatological disorder is angiokeratoma;

3.20. Method 3 or any of 3.1-3.18, wherein the dermatological disorder is hypohidrosis and/or anhidrosis;

3.21. Method 3, or any of 3.1-3.18, wherein the dermatological disorder is lymphedema;

3.22. Method 3, or any of 3.1-3.21, wherein the dermatological disorder is acroparesthesia;

3.23. Method 3.22, wherein the pain of the acroparesthesia is resistant to or not fully alleviated by treatment with analgesics or with non-steroidal anti-inflammatory agents;

3.24. Method 3, or any of 3.1-3.23, wherein the subject has Fabry disease;

3.25. Method 3.24, wherein the Fabry disease is not amenable to treatment with migalastat;

3.26. Method 3, or any of 3.1-3.25, wherein the subject has severely deficient or absent alpha-galactosidase activity (e.g., <1% of normal, e.g., as measured in circulating leukocytes);

3.27. Method 3, or any of 3.1-3.25, wherein the subject is diagnosed with a mutation in the gene GLA (e.g., a hemizygous male, a homozygous female or a heterozygous female), optionally wherein the mutation is a nonsense codon in the GLA gene;

3.28. Method 3, or any of 3.1-3.27, wherein the subject has marked accumulation of GL-3 in the skin and/or in the plasma;

3.29. Method 3.28, wherein the subject has marked accumulation of GL-3 in one or more of endothelial cells of superficial skin vessels, endothelial cells of deep skin vessels, smooth muscle cells of deep skin vessels, and perineurium cells;

3.30. Method 3, or any of 3.1-3.29, wherein the subject undergoes concurrent treatment with enzyme replacement therapy (ERT), e.g., using agalsidase alpha or agalsidase beta;

3.31. Method 3, or any of 3.1-3.29, wherein the subject undergoes concurrent treatment with an alpha-galactosidase inhibitor (e.g., migalastat);

3.32. Method 3, or any of 3.1-3.31, wherein the subject has a glucosylceramide (GL1) concentration in plasma of at least 2 μg/mL, e.g., at least 3 μg/mL, or at least 4 μg/mL in plasma;

3.33. Method 3, or any of 3.1-3.32, wherein the subject has a glucosylsphingosine (lyso-GL1) concentration in plasma of at least 65 ng/mL, e.g., at least 70 ng/mL, or at least 80 ng/mL, in plasma;

3.34. Method 3, or any of 3.1-3.32, wherein the subject has a GL3 concentration in plasma of at least 4 μg/mL, e.g., at least 6 μg/mL, or at least 8 μg/mL in plasma;

3.35. Method 3, or any of 3.1-3.34, wherein the subject is administered a daily dose of about 1 mg to about 150 mg of the compound according to Formula I (or any of II-XII, Ia-XIIa or Ib-XIIb, or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

3.36. Method 3, or any of 3.1-3.35, wherein the subject is a human adult patient, e.g., of an age from 18 to 80 years old, e.g., from 18 to 60 years old, or from 18 to 40 years old, or from 18 to 30 years old, or from 18 to 25 years old;

3.37. Method 3, or any of 3.1-3.35, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

3.38. Method 3, or any of 3.1-3.36, wherein the method results in reduction in GL-1 concentration in plasma of at least 30% after 2 weeks or 4 weeks or 8 weeks of treatment, e.g., at least 40%, at least 50%, or at least 60%;

3.39. Method 3, or any of 3.1-3.38, wherein the method results in reduction in GL-3 concentration in plasma of at least 20% after 2 weeks or 4 weeks or 8 weeks of treatment, e.g., at least 30%, at least 40%, or at least 50%;

3.40. Method 3, or any of 3.1-3.39, wherein the method results in reduction in GL-3 concentration in plasma of at least 40% after 26 weeks or 52 weeks or 104 weeks, e.g., at least 50%, at least 60% or at least 70%;

3.41. Method 3, or any of 3.1-3.40, wherein the method results in reduction in lyso-GL-3 concentration in plasma of at least 25% after 18 weeks or 26 weeks or 52 weeks, e.g., at least 35%, at least 45% or at least 50%;

3.42. Method 3, or any of 3.1-3.40, wherein the method results in reduction in GM3 concentration in plasma of at least 25% after 2 weeks or 4 weeks or 8 weeks, e.g., at least 30%, at least 40% or at least 50%;

3.43. Method 3, or any of 3.1-3.40, wherein the method results in a reduction in levels in skin (e.g., skin capillary endothelial cells) within 26 weeks or 52 weeks or 156 weeks, e.g., as shown by the extent of GL-3 inclusions;

3.44. Method 3.43, wherein the reduction in skin GL-3 levels (e.g., GL-3 inclusions) is found in one or more of endothelial cells of superficial skin vessels, endothelial cells of deep skin vessels, smooth muscle cells of deep skin vessels, and perineurium cells, within 26 weeks or 52 weeks or 156 weeks;

3.45. Method 3, or any of 3.1-3.44, wherein the subject has a GL-3 skin score (measured on a scale 0 to 4, as described in the Examples) of 2 or more prior to treatment, and the method results in a drop of at least one point on the scale, e.g., a drop of one point or two points; and/or wherein the subject has GL-3 inclusions in skin cells (e.g. endothelial cells) showing a cytoplasmic volume fraction of GL-3 inclusion of at least 0.25 (e.g., at least 0.27 or 0.3) prior to treatment, and the method results in a drop in the cytoplasmic volume fraction of GL-3 inclusions to less than 0.25 (e.g., less than 0.23 or less than 0.20, or less than 0.19). 3.46. Method 3, or any of 3.1-3.45, wherein the compound according to Formula I (or any of II-XII, Ia-XIIa or Ib-XIIb, or any of Compounds 1 or 1.1 to 1.75), or pharmaceutically acceptable salt or prodrug thereof, is administered by systemic administration, e.g., via a parenteral route or a non-parenteral route;

3.47. Method 3.46, wherein the route of administration is oral (enteral);

3.48. Method 3.46, wherein the route of administration is parenteral, e.g., by injection, such as, by intravenous injection;

3.49. Method 3, or any of 3.1-3.48, wherein the compound according to Formula I (or any of II-XII, Ia-XIIa or Ib-XIIb, or any of Compounds 1 or 1.1 to 1.75), or pharmaceutically acceptable salt or prodrug thereof, is administered by local administration, e.g., by topical administration;

3.50. Method 3, or any of 3.1-3.49, wherein the compound is (S)-quinuclidin-3-yl (2-(2-(4-fluorophenyl) thiazol-4-yl)propan-2-yl)carbamate or quinuclidin-3-yl (2-(4'-fluoro-[1,1'-biphenyl]-3-yl)propan-2-yl)carbamate;

3.51. Method 3.50, wherein the dosage of the compound is 15 mg/day orally administered;

3.52. Method 3.51, wherein the dosage of the compound is 15 mg/day in a single oral dose;

3.53. Method 3, or any of 3.1-3.52, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

In some embodiments of the present disclosure, a subject or subject is diagnosed with having a particular disease or disorder and is also diagnosed to have a particular genetic mutation, for example, one that is known to be a cause of the disease or disorder in question, although it often cannot be proven that a particular patient's disease or disorder is caused by the particular mutation that a person has been diagnosed with having. As used in this manner, the term "diagnosed to have a particular genetic mutation" means that a subject or patient has been tested, e.g., by DNA or RNA sequencing, protein profiling, or other suitable means, and found to have the mutation in question. However, as discussed further below, many genetic diseases and disorders can have multiple genetic causes (e.g., mutations), and patients may have multiple mutations each of which may, under some circumstances, be sufficient to cause the disease or disorder, without it being subject to proof that a particular mutation causes a particular disease or disorder in a particular patient.

As discussed above, one of the hallmarks of glycogen storage diseases is the abnormal accumulation of various glycolipids or glycosphingolipids in cells of the body. This accumulation is both a cause of the observable symptoms and signs of the disease, as well as a diagnostic marker evidencing the presence and/or progression of the disease. As used herein the phrase "marked accumulation" in reference to the measurement of GL-3, GL-1 and other biomarkers in plasma, skin or other soft tissues, means an accumulation of more than 25% over the maximum normal concentration of said compound. In some embodiments, "marked accumulation" means more than 50% over the maximum normal concentration of said compound.

The methods according to Method 2 et seq. and Method 3 et seq. may be beneficial for subjects who have been diagnosed with a lysosomal storage disease, particularly Fabry disease, but who are not yet experiencing the pain symptoms associated with the disease state, or who have only presented with the earliest dermatological symptoms of the disease. The methods according to Method 2 et seq. and Method 3 et seq. may also be beneficial for subjects who are at risk of developing a lysosomal storage disease, such as Fabry disease, due to, for example, a mutation in the subject or the subject's family lineage known to cause such disease. Therefore, in some embodiments of the methods described herein, the subject has been diagnosed as being at risk of developing said disease or disorder, and the method prevents or delays the onset and/or development of the pain symptoms of the disease or disorder in the subject. In some embodiments, the subject has been diagnosed as being at risk of developing said disease or disorder by virtue of having a mutation in a gene as described herein.

Pharmaceutical Compositions

The present disclosure also provides pharmaceutical compositions comprising at least one quinuclidine compound as described herein and at least one pharmaceutically acceptable excipient, e.g. for use according to the methods disclosed herein. The pharmaceutically acceptable excipient can be any such excipient known in the art including those described in, for example, Remington's Pharmaceutical Sciences, Mack Publishing Co. (A. R. Gennaro edit. 1985). Pharmaceutical compositions of the compounds presently disclosed may be prepared by conventional means known in the art including, for example, mixing at least one presently disclosed compound with a pharmaceutically acceptable excipient.

Thus, in one aspect the present disclosure provides a pharmaceutical dosage form comprising a quinuclidine compound as described herein and a pharmaceutically acceptable excipient, wherein the dosage form is formulated to provide, when administered (e.g. when administered orally), an amount of said compound sufficient to treat a disease or disorder as described herein (e.g., in any of Method 2 et seq., or Method 3 et seq.).

A pharmaceutical composition or dosage form of the invention can include an agent and another carrier, e.g. compound or composition, inert or active, such as a detectable agent, label, adjuvant, diluent, binder, stabilizer, buffers, salts, lipophilic solvents, preservative, adjuvant or the like. Carriers also include pharmaceutical excipients and additives, for example, proteins, peptides, amino acids, lipids, and carbohydrates (e.g. sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1 to 99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Carriers which may be used include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g. cyclodextrins, such as 2-hydroxypropyl-β-cyclodextrin), polyethylene glycols, flavoring agents, antimicrobial agents, sweeteners, antioxidants, antistatic agents, surfactants (e.g. polysorbates such as "TWEEN 20" and "TWEEN 80"), lipids (e.g. phospholipids, fatty acids), steroids (e.g. cholesterol), and chelating agents (e.g. EDTA).

The present disclosure also provides pharmaceutical compositions, and kits comprising said compositions, which contain at least one quinuclidine compound as described herein and at least one further pharmaceutically-active agent. These pharmaceutical compositions and kits may be adapted to allow simultaneous, subsequent and/or separate administration of the quinuclidine compound and the further active agent. For example, the quinuclidine compound and the further active agent may be formulated in separate dosage forms, e.g. in separate tablets, capsules, lyophilizates or liquids, or they may be formulated in the same dosage form, e.g. in the same tablet, capsule, lyophilizate or liquid. Where the quinuclidine compound and the further active agent are formulated in the same dosage form, the quinuclidine compound and the further active agent may be present substantially in admixture, e.g. within the core of a tablet, or they may be present substantially in discrete regions of the dosage form, e.g. in separate layers of the same tablet. In one embodiment, the pharmaceutical dosage form comprises a further agent which is capable of treating or preventing a supranuclear gaze palsy, e.g., in a patient having, diagnosed with or predisposed to a lysosomal storage disease, such as Gaucher Type 3 or Niemann-Pick Type C, or pain, e.g., in a patient having, diagnosed with or predisposed to a lysosomal storage disease, such as Fabry disease, as described herein.

In a further aspect the present disclosure provides a pharmaceutical composition comprising: (i) a quinuclidine compound as described herein; (ii) a further active agent; and (iii) a pharmaceutically acceptable excipient. In another embodiment, the further active agent is an agent which is capable of treating or preventing pain, or a dermatological disorder (e.g., angiokeratoma), e.g., in a patient having, diagnosed with or predisposed to a lysosomal storage disease, such as Fabry disease, as described herein, for example, when administered orally to a subject.

The presently disclosed quinuclidine compounds and pharmaceutical compositions can be used in an animal or human. Thus, a presently disclosed compound can be formulated as a pharmaceutical composition for oral, buccal, parenteral (e.g. intravenous, intramuscular or subcutaneous), topical, rectal or intranasal administration or in a form suitable for administration by inhalation or insufflation. In particular embodiments, the quinuclidine compound or pharmaceutical composition is formulated for systemic administration, e.g. via a non-parenteral route. In one embodiment, the quinuclidine compound or pharmaceutical composition is formulated for oral administration, e.g. in solid form. Such modes of administration and the methods for preparing appropriate pharmaceutical compositions are described, for example, in Gibaldi's Drug Delivery Systems in Pharmaceutical Care (1st ed., American Society of Health-System Pharmacists 2007).

The pharmaceutical compositions can be formulated so as to provide slow, extended, or controlled release of the active ingredient therein using, for example, hydroxypropyl methyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner, e.g. by using an enteric coating. Examples of embedding compositions include polymeric substances and waxes. The active ingredient can also be in micro-encapsulated form, if appropriate, with one or more pharmaceutically acceptable carriers, excipients, or diluents well known in the art (see, e.g., Remington's). The compounds presently disclosed may be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

In solid dosage forms for oral administration (e.g. capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, microcrystalline cellulose, calcium phosphate and/or silicic acid; (2) binders, such as, for example, carboxymethylcellulose, alginates, gelatin, pregelatinized maize starch, polyvinyl pyrrolidone, hydroxypropyl methylcellulose, sucrose and/or acacia; (3) humectants, such as glycerol; (4) disintegrating agents, such as agar-agar, calcium carbonate, sodium starch glycolate, potato or tapioca starch, alginic acid, certain silicates, and sodium carbonate; (5) solution retarding agents, such as paraffin; (6)

absorption accelerators, such as quaternary ammonium compounds; (7) wetting agents, such as, for example, sodium lauryl sulphate, acetyl alcohol and glycerol monostearate; (8) absorbents, such as kaolin and bentonite clay; (9) lubricants, such as talc, silica, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like. A tablet can be made by compression or molding, optionally with one or more accessory ingredients. Compressed tablets can be prepared using binders (for example, gelatin or hydroxypropyl methyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent. The tablets and other solid dosage forms, such as dragees, capsules, pills, and granules, can optionally be scored or prepared with coatings and shells, such as enteric coatings and other coatings well known in the art.

In embodiments, the pharmaceutical compositions are administered orally in a liquid form. Liquid dosage forms for oral administration of an active ingredient include pharmaceutically acceptable emulsions, microemulsions, solutions, suspensions, syrups and elixirs. Liquid preparations for oral administration may be presented as a dry product for constitution with water or other suitable vehicle before use. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g. cottonseed, groundnut, corn, germ, olive, castor and sesame oils), glycerol, tetrahydrofuryl alcohol, polyethylene glycols and fatty acid esters of sorbitan, and mixtures thereof. In addition to inert diluents, the liquid pharmaceutical compositions can include adjuvants such as wetting agents, emulsifying and suspending agents, sweetening, flavoring, coloring, perfuming and preservative agents, and the like. Suspensions, in addition to the active ingredient(s) can contain suspending agents such as, but not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof. Suitable liquid preparations may be prepared by conventional means with a pharmaceutically acceptable additive(s) such as a suspending agent (e.g. sorbitol syrup, methyl cellulose or hydrogenated edible fats); emulsifying agent (e.g. lecithin or acacia); non-aqueous vehicle (e.g. almond oil, oily esters or ethyl alcohol); and/or preservative (e.g. methyl or propyl p-hydroxybenzoates or sorbic acid). The active ingredient(s) can also be administered as a bolus, electuary, or paste.

For buccal administration, the composition may take the form of tablets or lozenges formulated in a conventional manner.

In embodiments, the pharmaceutical compositions are administered by non-oral means such as by topical application, transdermal application, injection, and the like. In related embodiments, the pharmaceutical compositions are administered parenterally by injection, infusion, or implantation (e.g. intravenous, intramuscular, intra-arterial, subcutaneous, and the like).

Presently disclosed compounds may be formulated for parenteral administration by injection, including using conventional catheterization techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g. sterile pyrogen-free water, before use.

The pharmaceutical compositions may be administered directly to the central nervous system. Accordingly, in certain embodiments the compositions are administered directly to the central nervous system so as to avoid the blood brain barrier. In some embodiments, the composition can be administered via direct spinal cord injection. In embodiments, the composition is administered by intrathecal injection. In some embodiments, the composition is administered via intracerebroventricular injection. In embodiments, the composition is administered into a cerebral lateral ventricle. In embodiments, the composition is administered into both cerebral lateral ventricles. In additional embodiments, the composition is administered via intrahippocampal injection. The compositions may be administered in one injection or in multiple injections. In other embodiments, the composition is administered to more than one location (e.g. to two sites in the central nervous system).

The pharmaceutical compositions can be in the form of sterile injections. The pharmaceutical compositions can be sterilized by, for example, filtration through a bacteria-retaining filter, or by incorporating sterilizing agents in the form of sterile solid compositions which can be dissolved in sterile water, or some other sterile injectable medium immediately before use. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilizing agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants. In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices. Materials for use in the preparation of microspheres and/or microcapsules include, but are not limited to, biodegradable/bioerodible polymers such as polyglactin, poly-(isobutyl cyanoacrylate), poly(2-hydroxyethyl-L-glutamine) and poly(lactic acid). Biocompatible carriers which can be used when formulating a controlled release parenteral formulation include carbohydrates such as dextrans, proteins such as albumin, lipoproteins or antibodies. Materials for use in implants can be non-biodegradable, e.g. polydimethylsiloxane, or biodegradable such as, e.g., poly(caprolactone), poly(lactic acid), poly(glycolic acid) or poly(ortho esters).

For topical administration, a presently disclosed compound may be formulated as an ointment or cream. Presently disclosed compounds may also be formulated in rectal compositions such as suppositories or retention enemas, e.g. containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

Generally, the agents and compositions described herein are administered in an effective amount or quantity sufficient to treat or prevent a supranuclear gaze palsy in a subject in need thereof. Typically, the dose can be adjusted within this range based on, e.g., age, physical condition, body weight, sex, diet, time of administration, and other clinical factors. Determination of an effective amount is well within the capability of those skilled in the art.

Having been generally described herein, the follow non-limiting examples are provided to further illustrate this invention.

EXAMPLES

General Procedures for Chemical Synthesis

General Procedure A: Carbamate Formation with Triphosgene

To a suspension of amine hydrochloride (1 equivalent) and triethylamine (3-4 equivalents) in a THF (concentration ~0.2M) at room temperature was added triphosgene (0.35 equivalents). The reaction mixture was stirred for 10 min and small amount of ether (1-2 mL) was added. The triethylammonium salt was filtered off to afford a clear solution of isocyanate in THF/ether.

To a solution of alcohol (1.5 equivalents) in THF (concentration ~0.2M) at room temperature was added NaH [60%, oil] (1.5 equivalents). The reaction mixture was stirred for 15 min and the above solution (isocyanate in THF/ether) was added dropwise. In a standard workup, the reaction was quenched with brine. The solution was extracted with EtOAc and the organic layer was dried over $Na_2SO_4$, filtered and concentrated. The crude material was purified on combiflash ($SiO_2$ cartridge, $CHCl_3$ and 2N $NH_3$ in MeOH) to afford the corresponding carbamate.

General Procedure B: Alkylation with Organocerium

A suspension of $CeCl_3$ (4 equivalents) in THF (concentration ~0.2M) was stirred at room temperature for 1 h. The suspension was cooled to −78° C. and MeLi/Ether [1.6M] (4 equivalents) was added dropwise. The organocerium complex was allowed to form for a period of 1 h and a solution of nitrile (1 equivalent) in THF (concentration 2.0M) was added dropwise. The reaction mixture was warmed up to room temperature and stirred for 18 h. The solution was cooled to 0° C. and quenched with water (~1 mL) followed by addition of 50% aqueous solution of ammonium hydroxide (~3 mL) until precipitated formed and settled to the bottom of the flask. The mixture was filtered through a pad of celite and concentrated. The crude material was treated with a solution of HCl/dioxane [4.0M]. The intermediate arylpropan-2-amine hydrochloride was triturated in ether and used as is for the next step. Alternatively, the crude free base amine was purified on combiflash ($SiO_2$ cartridge, $CHCl_3$ and 2N $NH_3$ in MeOH) to afford the corresponding arylpropylamine.

General Procedure C: Suzuki Coupling

To a solution of aryl halide (1 equivalent) in a mixture of DME/water [4:1] (concentration 0.2M) was added boronic acid (2 equivalents), palladium catalyst (0.1-0.25 equivalent) and sodium carbonate (2 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

Alternatively: To a solution of aryl halide (1 equivalent) in a mixture of toluene/water [20:1](concentration ~0.2 M) was added boronic acid (1.3-2.5 equivalents), palladium catalyst (0.05-0.15 equivalent), tricyclohexylphosphine (0.15-0.45 equivalent) and potassium phosphate (5 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

General Procedure D: Cyclopropanation

To a mixture of aryl nitrile (1 equivalent) and Ti(Oi-Pr)$_4$ (1.7 equivalents) stirring at −70° C., was added dropwise EtMgBr [3.0 M in ether] (1.1 equivalents). The reaction mixture was allowed to warm to 25° C. and stirred for 1 h. To the above mixture was added $BF_3$-$Et_2O$ (3 equivalents) dropwise at 25° C. After the addition, the mixture was stirred for another 2 h, and then quenched with aqueous HCl [2M]. The resulting solution was then basified by adding aqueous NaOH [2M]. The organic material was extracted with ethyl ether. The organic layers were combined, dried over $Na_2SO_4$, filtered and concentrated. The crude material was purified by silica gel column chromatography (eluting with petroleum ether/EtOAc: 10/1 to 1/1) to give the corresponding 1-aryl-cyclopropanamine.

General Procedure E: Biaryl Coupling Using Suzuki Conditions

To a stirred solution of the aryl halide component (1 equivalent) in 5:1 (v/v) dioxane/water (~0.15 M) or 5:1 (v/v) N,N-dimethylformamide (~0.15 M), was added the arylboronate or arylboronic acid component (1-1.5 equivalents), sodium carbonate (2-3 equivalents) and [1,1'-bis(diphenylphosphino)ferrocene]dichloropalladium(II) (0.05 equivalents). The mixture was heated (90° C.) overnight and then filtered through a plug of Celite. The Celite was rinsed with ethyl acetate and the combined filtrate was washed with brine, dried ($Na_2SO_4$) and concentrated. The residue was purified by flash chromatography over silica.

General Procedure F: Carbamate Formation Using an Isocyanate Generated Via a Mixed Anhydride/Curtius Rearrangement Route To a stirred solution of the carboxylic acid component (1 equivalent) in tetrahydrofuran (~0.1 M) was added triethylamine (2 equivalents). The reaction was cooled (0° C.) and treated with isobutyl chloroformate (1.5 equivalents). After 1 hour at 0° C., a solution of sodium azide (2 equivalents) in water (~1 M) was added and the reaction was allowed to warm to room temperature. After overnight stirring, the reaction was diluted with water and extracted with ethyl acetate. The combined extracts were washed with aqueous sodium bicarbonate solution and brine, dried ($Na_2SO_4$) and concentrated. The crude acyl azide was further dried via coevaporation with toluene and then taken up in toluene (~0.1 M). The stirred solution was refluxed for 2-2.5 hours, cooled and treated with an alcohol component (1.25-2 equivalents). The reaction was heated at reflux overnight and then concentrated. The residue was taken up in either ethyl acetate or chloroform and washed with aqueous sodium carbonate, ($Na_2SO_4$) and concentrated. The crude product was purified by flash chromatography over silica using chloroform/methanol (less polar carbamates) or chloroform/methanol/ammonia (more polar carbamates) solvent gradients.

Example 1: Synthesis of Quinuclidine Compounds 1-azabicyclo[2.2.2]oct-3-yl [2-(4'-fluorobiphenyl-3-yl)propan-2-yl]carbamate (Compound Using General Procedure C, 1-azabicyclo[2.2.2]oct-3-yl [2-(3-bromophenyl)propan-2-yl]carbamate (600 mg, 1.63 mmol), 4-fluorophenyl boronic acid (457 mg, 3.27 mmol) and palladium (II) acetate gave the title compound as a white solid (373 mg; 60%). $^1$H NMR (400 MHz, $CDCl_3$) δ 7.56 (s, 1H), 7.52 (dd, J=5.4, 8.4 Hz, 2H), 7.42-7.38 (m, 3H), 7.12 (m, 2H), 5.18 (5, 1H), 4.62 (s, 1H), 2.66 (m, 6H), 1.72 (s, 6H), 2.01-0.83 (m, 5H) ppm. $^{13}$C NMR (100 MHz, $CDCl_3$) δ 125.0, 124.0, 123.8, 116.0, 116.0, 71.3, 55.9, 55.5, 47.6, 46.7, 29.6, 25.6, 24.8, 19.8 ppm. Purity: 98.0% UPLCMS (210 nm); retention time 0.95 min; (M+1) 382.9. Anal. Calcd. for $C_{23}H_{27}FN_2O_2$.0.37 ($CHCl_3$): C, 65.86; H, 6.47; N, 6.57. Found: C, 65.85; H, 6.69; N, 6.49.

(S)-quinuclidin-3-yl 2-(2-(4-fluorophenyl)thiazol-4-yl)propan-2-ylcarbamate (Compound 2)

To a stirred solution of 4-fluorothiobenzamide (8.94 g, 57.6 mmol) in ethanol (70 mL) was added ethyl 4-chloroacetoacetate (7.8 mL, 58 mmol). The reaction was heated at reflux for 4 hours, treated with an addition aliquot of ethyl 4-chloroacetoacetate (1.0 mL, 7.4 mmol) and refluxed for an additional 3.5 hours. The reaction was then concentrated and the residue was partitioned between ethyl acetate (200 mL) and aqueous $NaHCO_3$ (200 mL). The organic layer was combined with a back-extract of the aqueous layer (ethyl acetate, 1×75 mL), dried ($Na_2SO_4$) and concentrated. The resulting amber oil was purified by flash chromatography using a hexane/ethyl acetate gradient to afford ethyl 2-(2-(4-fluorophenyl)thiazol-4-yl)acetate as a low melting, nearly colourless solid (13.58 g, 89%).

To a stirred solution of ethyl 2-(2-(4-fluorophenyl)thiazol-4-yl)acetate (6.28 g, 23.7 mmol) in DMF (50 mL) was added sodium hydride [60% dispersion in mineral oil] (2.84 g, 71.0 mmol). The frothy mixture was stirred for 15 minutes before cooling in an ice bath and adding iodomethane (4.4 mL, 71 mmol). The reaction was stirred overnight, allowing the cooling bath to slowly warm to room temperature. The mixture was then concentrated and the residue partitioned between ethyl acetate (80 mL) and water (200 mL). The organic layer was washed with a second portion of water (1×200 mL), dried ($Na_2SO_4$) and concentrated. The resulting amber oil was purified by flash chromatography using a hexane/ethyl acetate gradient to afford ethyl 2-(2-(4-fluorophenyl)thiazol-4-yl)-2-methylpropanoate as a colourless oil (4.57 g, 66%).

To a stirred solution of ethyl 2-(2-(4-fluorophenyl)thiazol-4-yl)-2-methylpropanoate (4.56 g, 15.5 mmol) in 1:1:1 THF/ethanol/water (45 mL) was added lithium hydroxide monohydrate (2.93 g, 69.8 mmol). The reaction was stirred overnight, concentrated and redissolved in water (175 mL). The solution was washed with ether (1×100 mL), acidified by the addition of 1.0 N HCl (80 mL) and extracted with ethyl acetate (2×70 mL). The combined extracts were dried ($Na_2SO_4$) and concentrated to afford 2-(2-(4-fluorophenyl)thiazol-4-yl)-2-methylpropanoic acid as a white solid (4.04 g, 98%). This material was used in the next step without purification.

To a stirred and cooled (0° c.) solution of 2-(2-(4-fluorophenyl)thiazol-4-yl)-2-methylpropanoic acid (4.02 g, 15.2 mmol) in THF (100 mL) was added trimethylamine (4.2 mL, 30 mmol) followed by isobutyl chloroformate (3.0 mL, 23 mmol). The reaction was stirred cold for another 1 hour before adding a solution of sodium azide (1.98 g, 30.5 mmol) in water (20 mL). The reaction was stirred overnight, allowing the cooling bath to slowly warm to room temperature. The mixture was then diluted with water (100 mL) and extracted with ethyl acetate (2×60 mL). The combined extracts were washed with aqueous $NaHCO_3$ (1×150 mL) and brine (1×100 mL), dried ($Na_2SO_4$) and concentrated. After coevaporating with toluene (2×50 mL), the resulting white solid was taken up in toluene (100 mL) and refluxed for 4 hours. (S)-3-quinuclidinol (3.87 g, 30.4 mmol) was then added and reflux was continued overnight. The reaction was concentrated and the residue partitioned between ethyl acetate (100 mL) and aqueous $NaHCO_3$ (150 mL). The organic layer was washed with water (1×150 mL), dried ($Na_2SO_4$) and concentrated. The resulting off-white solid was purified by flash chromatography using a chloroform/methanol/ammonia gradient to afford the title compound as a white solid (4.34 g, 73%). $^1$H NMR (400 MHz, $CDCl_3$) δ 7.96-7.88 (m, 2H), 7.16-7.04 (m, 3H), 5.55 (br s, 1H), 4.69-4.62 (m, 1H), 3.24-3.11 (m, 1H), 3.00-2.50 (m, 5H), 2.01-1.26 (m, 11H) ppm. $^{13}$C NMR (400 MHz, $CDCl_3$) δ 166.4, 165.1, 163.8 (d, J=250.3 Hz), 162.9, 155.0, 130.1 (d, J=3.3 Hz), 128.4 (d, J=8.5 Hz), 115.9 (d, J=22.3 Hz), 112.5, 71.2, 55.7, 54.2, 47.5, 46.5, 28.0, 25.5, 24.7, 19.6 ppm. Purity: 100% UPLCMS (210 nm & 254 nm); retention time 0.83 min; (M+1) 390.

(S)-quinuclidin-3-yl (2-(4'-(2-methoxyethoxy)-[1,1'-biphenyl]-4-yl)propan-2-yl)carbamate (Compound 3)

Using General Procedure E and the reaction inputs ethyl 2-(4-bromophenyl)-2-methylpropanoate and 4-(2-methoxyethoxy)phenylboronic acid, ethyl 2-(4'-(2-methoxyethoxy)-[1,1'-biphenyl]-4-yl)-2-methylpropanoate was prepared as an off-white solid. To a stirred solution of this compound (3.01 g, 8.78 mmol) in 1:1:1 (v/v/v) tetrahydrofuran/ethanol/water (45 mL) was added lithium hydroxide monohydrate (1.47 g, 61.4 mmol). The mixture was heated at reflux overnight and then concentrated. The residue was dissolved in water, treated with 1N hydrochloric acid (65 mL) and extracted with ethyl acetate. The combined organic layers were washed with brine, dried ($Na_2SO_4$) and concentrated to afford 2-(4'-(2-methoxyethoxy)-[1,1'-biphenyl]-4-yl)-2-methylpropanoic acid as a white solid (2.75 g, 100%). This intermediate and (S)-quinuclidin-3-ol were reacted according to General Procedure F to generate the title compound as a colourless, glassy solid. $^1$H NMR (400 MHz, DMSO-$d_6$) δ 7.62-7.29 (m, 7H), 7.01 (d, J=8.9 Hz, 2H), 4.47-4.37 (m, 1H), 4.17-4.08 (m, 2H), 3.72-3.62 (m, 2H), 3.32 (s, 3H), 3.09-2.25 (m, 6H), 2.05-1.18 (m, 11H) ppm. $^{13}$C NMR (100 MHz, DMSO-$d_6$) δ 157.9, 154.5, 146.7, 137.4, 132.5, 127.5, 125.7, 125.2, 114.8, 70.4, 70.0, 66.9, 58.2, 55.4, 54.2, 46.9, 45.9, 29.4, 25.3, 24.2, 19.2 ppm. Purity: 100%, 100% (210 & 254 nm) UPLCMS; retention time: 0.87 min; (M+H$^+$) 439.5.

1-azabicyclo[2.2.2]oct-3-yl [2-(biphenyl-3-yl)propan-2-yl]carbamate (Compound 4)

Using General Procedure C, 1-azabicyclo[2.2.2]oct-3-yl [2-(3-bromophenyl)propan-2-yl]carbamate (600 mg, 1.63 mmol), phenylboronic acid (398 mg, 3.27 mmol) and palladium (II) acetate gave the title compound as a white solid (379 mg, 64%). $^1$H NMR (400 MHz, $CDCl_3$) δ 7.61 (s, 1H), 7.56 (d, J=7.4 Hz, 2H), 7.50-7.38 (m, 4H), 7.34 (m, 2H), 5.16 (s, 1H), 4.63 (s, 1H), 3.39-2.09 (m, 6H), 1.72 (s, 6H), 2.02-0.73 (m, 5H) ppm. $^{13}$C NMR (100 MHz, $CDCl_3$) δ 154.8, 147.8, 141.6, 129.0, 129.0, 128.6, 127.5, 125.8, 125.0, 124.0, 71.6, 71.3, 55.9, 55.5, 47.6, 46.8, 31.5, 30.2, 30.0, 29.5, 25.6, 24.8, 19.8 ppm. Purity: 99% UPLCMS (210 nm); retention time 0.84 min; (M+1) 365.0. Anal. Calcd. for $C_{23}H_{28}N_2O_2$.0.29 ($CHCl_3$): C, 70.02; H, 7.14; N, 7.01. Found: C, 70.02; H, 7.37; N, 6.84.

(S)-quinuclidin-3-yl 2-(biphenyl-4-yl)propan-2-ylcarbamate (Compound 5)

Using General Procedure B, bromobenzonitrile (2.00 g, 11.0 mmol) was converted to the corresponding 2-(4-bromophenyl)propan-2-amine (1.20 g, 51%) as a brown oil.

Using General Procedure A, 2-(4-bromophenyl)propan-2-amine (1.0 g, 4.7 mmol) and (S)-quinuclidin-3-ol gave (S)-quinuclidin-3-yl 2-(4-bromophenyl)propan-2-ylcarbamate (1.0 g, 58%) as a brown oil.

Using General Procedure C, the above bromide (200 mg, 0.540 mmol), phenylboronic acid (133 mg, 1.10 mmol) and $[PdCl_2$ (pddf)]$CH_2Cl_2$ gave the title compound as a white solid (70 mg, 35%). $^1$H NMR (500 MHz, $CDCl_3$) δ 7.60-7.53 (m, 4H), 7.47 (d, J=8.5 Hz, 2H), 7.42 (t, J=7.5 Hz, 2H), 7.33 (t, J=7.5 Hz, 1H), 5.26 (br s, 1H), 4.64 (m, 1H), 3.33-3.15 (m, 1H), 3.10-2.45 (m, 5H), 2.40-1.80 (m, 2H), 1.78-1.58 (m, 7H), 1.55-1.33 (m, 2H) ppm. $^{13}$C NMR (125 MHz, $CDCl_3$) δ 154.5, 146.1, 140.8, 139.5, 128.7, 127.2, 127.1, 127.1, 125.2, 70.9, 55.5, 55.1, 47.4, 46.4, 31.1, 29.5, 25.3, 24.5, 19.5 ppm. Purity: 100% LCMS (214 nm & 254 nm); retention time 1.56 min; (M+1) 365.

Quinuclidin-3-yl 1-(biphenyl-4-yl)cyclopropylcarbamate (Compound 6)

Using General Procedure D, bromobenzonitrile (3.00 g, 16.5 mmol) was converted to the corresponding 1-(4-bromophenyl)cyclopropanamine (1.80 g, 51%) as a yellow solid.

Using General Procedure A, 1-(4-bromophenyl)cyclopropanamine (1.0 g, 4.7 mmol) and quinuclidin-3-ol gave quinuclidin-3-yl 1-(4-bromophenyl)cyclopropyl-carbamate (1.3 g, 75%) as a white semi-solid.

Using General Procedure C, the above carbamate (400 mg, 1.12 mmol), phenylboronic acid (267 mg, 2.22 mmol) and $[PdCl_2$ (pddf)]$CH_2Cl_2$ the title compound as a viscous oil (100 mg, 25%). $^1$H NMR (500 MHz, $CDCl_3$) δ 7.47 (d, J=7.5 Hz, 2H), 7.43 (d, J=8.0 Hz, 2H), 7.33 (t, J=7.5 Hz, 2H), 7.26-7.15 (m, 3H), 5.93 (br s, 0.6H), 5.89 (br s, 0.4H), 4.67 (m, 1H), 3.20-3.06 (m, 1H), 2.88-2.42 (m, 5H), 1.98-1.08 (m, 9H) ppm. $^{13}$C NMR (125 MHz, $CDCl_3$) δ 155.0, 141.0, 139.7, 138.2, 127.7, 126.1, 126.0, 124.8, 124.1, 70.0, 54.5, 46.3, 45.4, 34.1, 24.3, 23.2, 18.3, 17.0 ppm. Purity: 100% LCMC (214 nm & 254 nm); retention time 1.52 min; (M+1) 363.

(S)-quinuclidin-3-yl 1-(4'-fluorobiphenyl-4-yl)cyclopropylcarbamate (Compound 7)

Using General Procedure C, (S)-quinuclidin-3-yl 1-(4-bromophenyl)cyclopropyl carbamate, 4-F-phenylboronic acid and $[PdCl_2$ (pddf)]$CH_2Cl_2$ gave the title compound as a white solid (45%). $^1$H NMR (500 MHz, DMSO-$d_6$) δ 8.06-7.83 (d, 1H), 7.69-7.66 (m, 2H), 7.59-7.55 (m, 2H), 7.29-7.22 (m, 4H), 4.56-4.54 (m, 1H), 3.13-2.32 (m, 6H), 1.91-1.19 (m, 9H) ppm. $^3$C NMR (125 MHz, DMSO-$d_6$) δ 163.2, 161.2, 156.4, 143.7, 136.9, 128.9, 128.8, 126.8, 125.6, 116.2, 116.0, 70.7, 55.8, 47.4, 46.4, 34.8, 25.7, 24.6, 19.6, 18.7, 18.6 ppm. Purity: >97% LCMS (214 nm & 254 nm); retention time 1.96 min; (M+1) 381.2.

(S)-1-azabicyclo[2.2.2]oct-3-yl [1-(2',4'-difluorobiphenyl-4-yl)cyclopropyl]carbamate (Compound 8)

Using General Procedure C, (S)-quinuclidin-3-yl 1-(4-bromophenyl)cyclopropylcarbamate (0.446 g, 1.22 mmol), 2,4-difluorophenyl boronic acid (0.386 g, 2.44 mmol) and $Pd(OAc)_2$ (0.015 g, 0.067 mmol) gave the title compound as a tan solid (0.111 g, 23%). $^1$H NMR ($CDCl_3$) δ 7.43 (dd, J=8.4, 1.6 Hz, 2H), 7.40-7.33 (m, 1H), 7.31 (d, J=7.7 Hz, 2H), 6.99-6.81 (m, 2H), 5.54 (d, J=48.0 Hz, 1H), 4.82-4.65

(m, 1H), 3.30-3.07 (m, 1H), 2.98-2.44 (m, 5H), 1.97 (d, J=32.7 Hz, 1H), 1.83 (d, J=10.3 Hz, 1H), 1.64 (s, 1H), 1.52 (s, 1H), 1.39 (s, 1H), 1.31 (d, J=6.8 Hz, 4H) ppm. $^{13}$C NMR major rotomer ($CDCl_3$) δ 162.2 (dd, J=12.8, 249.1 Hz), 159.8 (dd, J=11.8, 251.0 Hz), 156.9, 156.0, 142.6, 133.1, 131.3 (m), 128.9, 125.6, 124.9, 111.5 (dd, J=3.9, 21.2 Hz) 104.4 (dd, J=25.2, 29.4 Hz), 72.1, 71.6, 55.7, 47.4, 46.5, 35.7, 35.3, 25.5, 24.6, 24.4, 19.5, 18.1 ppm. Purity: LCMS>99.3% (214 nm & 254 nm); retention time 0.90 min; (M+1) 399.0.

1-azabicyclo[2.2.2]oct-3-yl [1-(4'-methoxybiphenyl-4-yl)cyclopropyl]carbamate (Compound 9)

Using General Procedure C, quinuclidin-3-yl 1-(4-bromophenyl)cyclopropylcarbamate (0.485 g, 1.33 mmol), 4-methoxyphenyl boronic acid (0.404 g, 2.66 mmol) and $Pd(OAc)_2$ (0.016 g, 0.071 mmol) gave the title compound as a grey solid (0.337 mg, 65%). $^1$H NMR ($CDCl_3$) δ 7.48 (dd, J=8.6, 5.5 Hz, 4H), 7.29 (d, J=7.6 Hz, 2H), 6.96 (d, J=8.8 Hz, 2H), 5.58 (d, J=48.7 Hz, 1H), 4.83-4.63 (m, 1H), 3.84 (s, 3H), 3.20 (dd, J=24.0, 15.5 Hz, 1H), 2.97-2.42 (m, 5H), 1.97 (d, J=30.9 Hz, 1H), 1.81 (s, 1H), 1.75-1.33 (m, 3H), 1.28 (d, J=6.8 Hz, 4H) ppm. $^{13}$C NMR major rotomer ($CDCl_3$) δ 159.1, 156.0, 141.4, 139.0, 133.4, 128.0, 126.7, 125.9, 114.2, 71.5, 55.7, 55.3, 47.4, 46.5, 35.3, 25.5, 24.6, 19.6, 17.8 ppm. Purity: LCMS>97.1% (214 nm & 254 nm); retention time 0.88 min; (M+1) 393.4.

Quinuclidin-3-yl 2-(5-(4-fluorophenyl)thiophen-3-yl)propan-2-ylcarbamate (Compound 10)

To a stirred and cooled (0° C.) solution of ethyl 5-bromothiophene-3-carboxylate (13.30 g, 56.57 mmol) in THF (100 mL) was added a solution of methylmagnesium bromide in diethyl ether [3.0 M] (55.0 mL, 165 mmol), dropwise over 20 minutes. After 2 hours, the reaction solution was concentrated. The residue was taken up in aqueous $NH_4Cl$ (200 mL) and extracted with ethyl acetate (2×100 mL). The combined extracts were dried ($Na_2SO_4$) and concentrated. The resulting amber oil was purified by flash chromatography using a hexane/ethyl acetate gradient to afford 2-(5-bromothiophen-3-yl)propan-2-ol as a pale amber oil (8.05 g, 64%).

To a stirred solution of 2-(5-bromothiophen-3-yl)propan-2-ol (8.03 g, 36.3 mmol) in methylene chloride (80 mL) was added sodium azide (7.08 g, 109 mmol) followed by trifluoroacetic acid (8.0 mL; dropwise over 5-6 minutes). The thickening suspension was stirred for 1.5 hour before diluting with water (350 mL) and extracting with ethyl acetate (1×200 mL). The organic layer was washed with aqueous $NaHCO_3$ (1×250 mL), dried ($Na_2SO_4$) and concentrated to afford the crude azide product. To a stirred solution of this material in THF (160 mL) was added water (11 mL) followed by triphenylphosphine (23.8 g, 90.7 mmol). The reaction was stirred for 2 days before concentrating. The resulting residue was dissolved in ethyl acetate (250 mL) and extracted with 1 N aqueous HCl (4×75 mL). The combined extracts were basified with concentrated $NH_4OH$ and extracted with ethyl acetate (2×100 mL). These extracts were, in turn, dried ($Na_2SO_4$) and concentrated. The resulting amber oil was purified by flash chromatography using a methylene chloride/methanol/ammonia gradient to afford a mixture of 2-(5-bromothiophen-3-yl)propan-2-amine and triphenylphosphine oxide (~70/30 ratio) as a viscous amber oil (1.32 g, 17%).

To a stirred solution of 3-quinuclidinol (3.00 g, 23.6 mmol) in THF (100 mL) was added 4-nitrophenyl chloroformate (5.94 g, 29.5). After stirring for 4 hours, the precipitate was filtered off, rinsed with THF and air dried on the frit under house vacuum. The filter cake was dissolved in ethyl acetate (150 mL) and washed with aqueous $NaHCO_3$ (1×150 mL) and water (2×150 mL). The organic layer was dried ($Na_2SO_4$) and concentrated to afford crude 4-nitrophenyl quinuclidin-3-yl carbonate product, which was used in the next step without purification.

To a stirred solution of 2-(5-bromothiophen-3-yl)propan-2-amine (0.366 g, 1.66 mmol) in THF (10 mL) was added 4-nitrophenyl quinuclidin-3-yl carbonate (0.571 g, 1.95 mmol) and a few granules of 4-(dimethylamino)pyridine. The mixture was refluxed overnight, concentrated and partitioned between ethyl acetate (50 mL) and aqueous $NaHCO_3$ (50 mL). The organic layer was washed again with aqueous $NaHCO_3$ (1×50 mL), dried ($Na_2SO_4$) and concentrated. The resulting dirty yellow gum was purified by flash chromatography using a chloroform/methanol/ammonia gradient to afford quinuclidin-3-yl (1-(5-bromothiophen-3-yl)cyclopropyl)carbamate as an off-white solid (0.305 g, 49%).

Using General Procedure C, quinuclidin-3-yl (1-(5-bromothiophen-3-yl)cyclopropyl)carbamate (0.227 g, 0.742 mmol), 4-fluorophenyl boronic acid (0.208 g, 1.49 mmol), tricyclohexylphosphine (0.021 g, 0.075 mmol), potassium phosphate (0.866, 4.08 mmol) and palladium acetate (8.0 mg, 36 μmol) gave the title compound as a grey solid (0.142 g, 49%). $^1$H NMR (400 MHz, $CDCl_3$) δ 7.60-7.45 (m, 2H), 7.24-7.19 (m, 1H), 7.10-6.97 (m, 3H), 5.23 (br s, 1H), 4.72-4.61 (m, 1H), 3.30-3.04 (m, 1H), 3.03-2.25 (m, 5H), 2.09-1.02 (m, 11H) ppm. $^{13}$C NMR (400 MHz, $CDCl_3$) δ 162.3 (d, J=247.1 Hz), 154.5, 149.8, 143.6, 130.7, 127.4 (d, J=8.1 Hz), 121.8, 118.9, 115.8 (d, J=21.6 Hz), 70.8, 55.5, 53.4, 47.3, 46.4, 29.0, 25.4, 24.4, 19.4 ppm. Purity: 95.8% UPLCMS (210 nm & 254 nm); retention time 0.90 min; (M+1) 389.

(S)-quinuclidin-3-yl 2-(3-(4-fluorophenyl)isothiazol-5-yl)propan-2-ylcarbamate (Compound To stirred solution of 2-(3-(4-fluorophenyl)isothiazol-5-yl)propan-2-amine (1.21 g, 5.12 mmol) in toluene was added a solution of phosgene in toluene [~1.9 M] (10.8 mL, 20.5 mmol). The reaction was heated at reflux for two hours and then concentrated. The residue was co-evaporated with toluene (2×15 mL) to afford the crude isocyanate intermediate as golden oil. This material was taken up in toluene (10 mL) and treated with (S)-3-quinuclidinol (0.749 g, 5.89 mmol). The reaction was heated at reflux overnight and concentrated. The residue was purified by flash chromatography using a chloroform/methanol/ammonia gradient to afford the title compound as a white solid (0.971 g, 49%). $^1$H NMR (400 MHz, DMSO-$d_6$) δ 8.09-8.00 (m, 2H), 7.87 (br s, 1H), 7.75 (s, 1H), 7.35-7.25 (m, 2H), 4.54-4.45 (m, 1H), 3.14-2.92 (m, 1H), 2.87-2.17 (m, 5H), 1.98-0.98 (m, 11H) ppm. $^{13}$C NMR (400 MHz, DMSO-$d_6$) δ 180.1, 165.6, 162.6 (d, J=246.4 Hz), 154.7, 131.2 (d, J=3.0 Hz), 128.7 (d, J=8.4 Hz), 118.2, 115.7 (d, J=21.8 Hz), 70.6, 55.3, 52.8, 46.9, 45.9, 29.9, 25.2, 24.2, 19.2 ppm. Purity: 100% UPLCMS (210 nm & 254 nm); retention time 0.82 min; (M+1) 390.

(S)-quinuclidin-3-yl 2-(4-(4-fluorophenyl)thiazol-2-yl)propan-2-ylcarbamate (Compound To a stirred solution of ethyl 3-amino-3-thioxopropanoate (20.00 g, 135.9 mmol) in ethanol (120 mL) was added 2-bromo-4'-fluoroacetophenone (29.49 g, 135.9 mmol). The mixture was refluxed for 1 hour, concentrated and partitioned between ethyl acetate (300 mL) and aqueous $NaHCO_3$ (400 mL). The organic layer was combined with a back-extract of the aqueous layer (ethyl acetate, 1×100 mL), dried ($Na_2SO_4$) and concentrated. The resulting light brown solid was purified by flash chromatography using a hexane/ethyl acetate gradient to afford ethyl 2-(4-(4-fluorophenyl) thiazol-2-yl)acetate as an off-white solid (29.92 g, 83%).

To a stirred and cooled (−78° C.) solution of ethyl 2-(4-(4-fluorophenyl)thiazol-2-yl)acetate (10.00 g, 37.69 mmol) in THF (250 mL) was added a solution of potassium t-butoxide in THF [1.0 M] (136 mL, 136 mmol), dropwise over 15 minutes, followed by 18-crown-6 (1.6 mL, 7.5 mmol). After an additional 30 minutes at −78° C., iodomethane (8.5 mL) was added, dropwise over 5 minutes. The reaction was stirred cold for another 2 hours before pouring into water (450 mL) and extracting with ethyl acetate (2×150 mL). The combined extracts were washed with brine (1×200 mL), dried ($Na_2SO_4$) and concentrated. The resulting brown oil was purified by flash chromatography using a hexane/ethyl acetate gradient to afford ethyl 2-(4-(4-fluorophenyl) thiazol-2-yl)-2-methylpropanoate as a pale amber oil (8.64 g, 78%).

To a stirred solution of ethyl 2-(4-(4-fluorophenyl)thiazol-2-yl)-2-methylpropanoate (0.900 g, 3.07 mmol) in 1:1:1 THF/ethanol/water (15 mL) was added lithium hydroxide monohydrate (0.451 g, 10.7 mmol). After overnight stirring, the reaction was concentrated and redissolved in water (80 mL). The solution was washed with ether (1×50 mL), acidified with the addition of 1N HCl (15 mL) and extracted with ethyl acetate (2×50 mL). The combined extracts were dried ($Na_2SO_4$) and concentrated to afford 2-(4-(4-fluorophenyl)thiazol-2-yl)-2-methylpropanoic acid as a pale golden solid (0.808 g, 99%).

To stirred and cooled (0° C.) solution of 2-(4-(4-fluorophenyl)thiazol-2-yl)-2-methylpropanoic acid (0.784 g, 2.96 mmol) in THF (25 mL) was added triethylamine (0.82 mL, 5.9 mmol) followed by isobutyl chloroformate (0.58 mL, 4.4 mmol). The reaction was stirred cold for another 1 hour before adding a solution of sodium azide (0.385 g, 5.92 mmol) in water (7 mL). The reaction was stirred overnight, allowing the cooling bath to slowly warm to room temperature. The mixture was then diluted with water (100 mL) and extracted with ethyl acetate (2×60 mL). The combined extracts were washed with aqueous $NaHCO_3$ (1×150 mL) and brine (1×100 mL), dried ($Na_2SO_4$) and concentrated. After co-evaporating with toluene (2×30 mL), the resulting off-white solid was taken up in toluene (25 mL) and refluxed for 4 hours. (S)-3-quinuclidinol (0.753 g, 5.92 mmol) was then added and reflux was continued for 3 hours. The reaction was concentrated and the residue was purified by flash chromatography using a chloroform/methanol/ammonia gradient to afford the title compound as a white solid (0.793 g, 69%). $^1H$ NMR (400 MHz, $CDCl_3$) δ 7.90-7.81 (m, 2H), 7.32 (s, 1H), 7.14-7.05 (m, 2H), 5.76 (br s, 1H), 4.72-4.65 (m, 1H), 3.26-3.10 (m, 1H), 3.03-2.37 (m, 5H), 2.05-1.23 (m, 11H) ppm. $^{13}C$ NMR (400 MHz, $CDCl_3$) δ 177.6, 162.6 (d, J=248.4 Hz), 154.8, 153.6, 130.8 (d, J=3.2 Hz), 128.1 (d, J=8.1 Hz), 115.9 (d, J=21.7 Hz), 112.2, 71.6, 55.7, 47.4, 46.5, 29.1, 25.4, 24.7, 19.6 ppm. Purity: 100% UPLCMS (210 nm & 254 nm); retention time 0.82 min; (M+1) 390.

Quinuclidin-3-yl (2-(4'-(2-methoxyethoxy)-[1,1'-biphenyl]-4-yl)propan-2-yl)carbamate (Compound 13)

Using General Procedure F and the reaction inputs 2-(4'-(2-methoxyethoxy)-[1,1'-biphenyl]-4-yl)-2-methylpropanoic acid (prepared as described in Example 3) and quinuclidin-3-ol, the title compound was generated as a colourless, glassy solid (23%). NMR data matched that of Example 3. Purity: 100%, 99.1% (210 & 254 nm) UPLCMS; retention time: 0.87 min; (M+H$^+$) 439.0.

(S)-quinuclidin-3-yl (2-(3'-(2-methoxyethoxy)-[1,1'-biphenyl]-4-yl)propan-2-yl)carbamate (Compound 14)

Exchanging 4-(2-methoxyethoxy)phenylboronic acid for 3-(2-methoxyethoxy)phenylboronic acid, the reaction sequence outlined in Example 3 was used to prepare 2-(3'-(2-methoxyethoxy)-[1,1'-biphenyl]-4-yl)-2-methylpropanoic acid. This intermediate and quinuclidin-3-ol were reacted according to General Procedure F to generate the title compound as a glassy, colourless solid. $^1H$ NMR (400 MHz, DMSO-$d_6$) δ 7.63-7.31 (m, 6H), 7.24-7.10 (m, 2H), 6.92 (dd, J=8.2, 1.9 Hz, 1H), 4.51-4.34 (m, 1H), 4.21-4.08 (m, 2H), 3.72-3.64 (m, 2H), 3.32 (s, 3H), 3.09-2.26 (m, 5H), 2.04-1.22 (m, 9H) ppm. $^{13}C$ NMR (100 MHz, DMSO-$d_6$) δ 158.9, 154.6, 147.6, 141.5, 137.6, 129.9, 126.3, 125.2, 118.9, 113.2, 112.5, 70.4, 70.0, 66.9, 58.2, 55.4, 54.2, 46.9, 45.9, 29.4, 25.3, 24.2, 19.2 ppm. Purity: 100%, 100% (210 & 254 nm) UPLCMS; retention time: 0.91 min; 15 (M+H$^+$) 439.4.

Quinuclidin-3-yl (2-(4'-(2-methoxyethoxy)-[1,1'-biphenyl]-3-yl)propan-2-yl)carbamate (Compound 15)

Exchanging ethyl 2-(4-bromophenyl)-2-methylpropanoate for ethyl 2-(3-bromophenyl)-2-methylpropanoate, the reaction sequence outlined in Example 3 was used to prepare 2-(4'-(2-methoxyethoxy)-[1,1'-biphenyl]-3-yl)-2-methylpropanoic acid. This intermediate and quinuclidin-3-ol were reacted according to General Procedure F to generate the title compound as a yellow solid. $^1H$ NMR (400 MHz, DMSO-$d_6$) δ 7.62-7.20 (m, 7H), 7.03 (d, J=8.7 Hz, 2H), 4.48-4.35 (m, 2H), 4.18-4.08 (m, 2H), 3.72-3.62 (m, 2H), 3.32 (s, 3H), 3.10-2.19 (m, 6H), 2.10-1.10 (m, 11H) ppm. $^{13}C$ NMR (100 MHz, DMSO-$d_6$) δ 158.0, 154.6, 148.8, 139.5, 133.1, 128.5, 127.7, 123.8, 123.2, 122.7, 114.8, 70.4, 69.9, 67.0, 58.2, 55.3, 54.5, 47.0, 45.9, 29.4, 25.3, 24.2, 19.2 ppm. Purity: 97.4%, 94.6% (210 & 254 nm) UPLCMS; retention time: 0.88 min; (M+H$^+$) 439.3.

Quinuclidin-3-yl (2-(4'-(3-methoxypropoxy)-[1,1'-biphenyl]-4-yl)propan-2-yl)carbamate (Compound 16)

To a stirred solution of 4-iodophenol (10.05 g, 45.68 mmol) in acetonitrile (100 mL) was added potassium carbonate (6.95 g, 50.2 mmol) and 1-chloro-3-methoxypropane (6.4 mL, 57.1 mmol). The mixture was heated at reflux overnight and then concentrated. The residue was taken up in water and extracted with ethyl acetate. The combined extracts were washed with aqueous sodium bicarbonate solution, dried ($Na_2SO_4$) and concentrated. The crude material was purified by flash chromatography over silica using a hexane/ethyl acetate eluent to afford 1-iodo-4-(3-methoxypropoxy)benzene as a colourless oil (4.39 g, 33%). This intermediate and ethyl 2-methyl-2-(4-(4,4,5,5-tetramethyl-1,3,2-dioxaborolan-2-yl)phenyl)propanoate were reacted according to General Procedure E to generate ethyl 2-(4'-(3-methoxypropoxy)-[1,1'-biphenyl]-4-yl)-2-methylpropanoate. To a stirred solution of this compound (0.693 g, 1.94 mmol) in 1:1:1 (v/v/v) tetrahydrofuran/ethanol/water (10 mL) was added lithium hydroxide monohydrate (0.326 g, 7.77 mmol). The mixture was heated at reflux overnight and then concentrated. The residue was dissolved in water, treated with 1N hydrochloric acid (10 mL) and extracted with ethyl acetate. The combined organic layers were washed with brine, dried ($Na_2SO_4$) and concentrated to afford 2-(4'-(3-methoxypropoxy)-[1,1'-biphenyl]-4-yl)-2-methylpropanoic acid as a waxy, off-white solid (0.630 g, 99%). This intermediate and quinuclidin-3-ol were reacted according to General Procedure F to generate the title compound as a glassy, colourless solid (62%). $^1$H NMR (400 MHz, DMSO-$d_6$) δ 7.61-7.29 (m, 7H), 7.00 (d, J=8.8 Hz, 2H), 4.47-4.36 (m, 1H), 4.05 (t, J=6.4 Hz, 2H), 3.48 (t, J=6.3 Hz, 2H), 3.26 (s, 3H), 3.10-2.25 (m, 6H), 2.04-1.74 (m, 4H), 1.65-1.23 (m, 9H) ppm. $^{13}$C NMR (100 MHz, DMSO-d6) δ 158.0, 154.5, 146.7, 137.4, 132.4, 127.5, 125.7, 125.2, 114.8, 69.9, 68.5, 64.6, 57.9, 55.4, 54.2, 46.9, 46.0, 29.4, 29.0, 25.2, 24.1, 19.2 ppm. Purity: 97.7%, 98.2% (210 & 254 nm) UPLCMS; retention time: 0.96 min; (M+H$^+$) 453.5.

Quinuclidin-3-yl (2-(4'-(hydroxymethyl)-[1,1'-biphenyl]-4-yl)propan-2-yl)carbamate (Compound 17)

Using General Procedure E and the reaction inputs ethyl 2-(4-bromophenyl)-2-methylpropanoate and 4-formylphenylboronic acid, ethyl 2-(4'-formyl-[1,1'-biphenyl]-4-yl)-2-methylpropanoate was prepared as a pale amber solid. This intermediate and quinuclidin-3-ol were reacted according to General Procedure F to generate quinuclidin-3-yl (2-(4'-formyl-[1,1'-biphenyl]-4-yl)propan-2-yl)carbamate as foamy, yellow solid. To a stirred solution of this material (0.755 g, 1.92 mmol) in 2:1 (v/v) tetrahydrofuran/ethanol (15 mL) was added sodium borohydride (0.073 g, 1.93 mmol). After 45 minutes, the reaction was diluted with water and extracted with chloroform. The combined extracts were dried ($Na_2SO_4$) and concentrated onto silica. Flash chromatography over silica using a chloroform/methanol/ammonia eluent provided the title compound as a white solid (0.323 g, 43%). $^1$H NMR (400 MHz, DMSO-$d_6$) δ 7.66-7.29 (m, 9H), 5.18 (t, J=5.7 Hz, 1H), 4.53 (d, J=5.7 Hz, 2H), 4.46-4.37 (m, 1H), 3.11-2.19 (m, 6H), 2.11-1.10 (m, 11H) ppm. $^{13}$C NMR (100 MHz, DMSO-$d_6$) δ 154.7, 147.3, 141.5, 138.4, 137.7, 127.0, 126.2, 126.1, 125.3, 70.0, 62.6, 55.4, 54.2, 46.9, 45.9, 29.4, 25.3, 24.2, 19.2 ppm. Purity: 97.5%, 99.1% (210 & 254 nm) UPLCMS; retention time: 0.73 min; (M+H$^+$) 395.

Quinuclidin-3-yl (2-(4'-(2-hydroxyethyl)-[1,1'-biphenyl]-4-yl)propan-2-yl)carbamate (Compound 18)

Using General Procedure E and the reaction inputs 1-(2-(benzyloxy)ethyl)-4-bromobenzene and ethyl 2-methyl-2-(4-(4,4,5,5-tetramethyl-1,3,2-dioxaborolan-2-yl)phenyl) propanoate, ethyl 2-(4'-(2-(benzyloxy)ethyl)-[1,1'-biphenyl]-4-yl)-2-methylpropanoate was prepared as a colourless gum. To a stirred solution of this compound (1.34 g, 3.33 mmol) in 1:1:1 (v/v/v) tetrahydrofuran/ethanol/water (18 mL) was added lithium hydroxide monohydrate (0.698 g, 16.6 mmol). After heating at reflux overnight, the reaction was concentrated and partitioned between water and diethyl ether. The resulting emulsion was extracted repeatedly with 0.2 N aqueous sodium hydroxide solution (5×50 mL). The clear portion of the aqueous layer was removed each time. The combined aqueous layers were then treated with 1.0 N hydrochloric acid (80 mL) and the resulting suspension of white solid was extracted with ethyl acetate. The combined organic layers were dried ($Na_2SO_4$) and concentrated to afford 2-(4'-(2-(benzyloxy)ethyl)-[1,1'-biphenyl]-4-yl)-2-methylpropanoic acid as a white solid (1.20 g, 96%). This compound and quinuclidin-3-ol were reacted according to General Procedure F to generate quinuclidin-3-yl (2-(4'-(2-benzyloxyethyl)-[1,1'-biphenyl]-4-yl)propan-2-yl)carbamate. To a stirred solution of this material (0.435 g, 0.806 mmol) in methanol was added 1.0 N hydrochloric acid (1 mL) and 10% palladium on carbon (50% water; 0.087 g). The mixture was cycled between vacuum and a nitrogen purge several times, refilling with hydrogen after the last evacuation. After 1.25 hours the reaction was filtered through Celite and concentrated. The residue was taken up in aqueous sodium carbonate solution and extracted with 4:1 (v/v) chloroform/isopropanol. The combined extracts were dried ($Na_2SO_4$) and concentrated onto silica. Flash chromatography over silica using a chloroform/methanol/ammonia gradient provided the purified title compound as a colourless solid. $^1$H NMR (400 MHz, DMSO-$d_6$) δ 7.85-7.63 (m, 1H), 7.63-7.19 (m, 8H), 4.78-4.62 (m, 2H), 3.71-2.78 (m, 8H), 2.76 (t, J=6.8 Hz, 2H), 2.26-1.96 (m, 2H), 1.96-1.40 (m, 9H) ppm. $^{13}$C NMR (100 MHz, DMSO-$d_6$) δ 153.8, 146.8, 138.7, 137.9, 137.6, 129.4, 126.3, 126.1, 125.3, 66.2, 62.1, 54.4, 52.8, 45.4, 44.5, 38.6, 29.5, 29.2, 24.0, 19.9, 16.6 ppm. Purity: 100%, 100% (210 & 254 nm) UPLCMS; retention time: 0.75 min; (M+H$^+$) 409.

Quinuclidin-3-yl (2-(2-(4-(3-methoxypropoxy)phenyl)thiazol-4-yl)propan-2-yl)carbamate (Compound 19)

To a stirred suspension of 4-methoxythiobenzamide (9.99 g, 59.7 mmol) in ethanol (75 mL) was added ethyl 4-chloroacetoacetate (8.1 mL, 60 mmol). The mixture was heated at reflux for 4 hours before cooling, adding additional ethyl 4-chloroacetoacetate (0.81 mL, 6.0 mmol) and returning to reflux. After 4 more hours of heating the reaction was concentrated and partitioned between ethyl acetate and aqueous sodium bicarbonate solution. The organic layer was combined with additional ethyl acetate extracts, dried ($Na_2SO_4$) and concentrated. The crude product was purified by flash chromatography over silica using a hexane/ethyl acetate gradient to afford ethyl 2-(2-(4-methoxyphenyl)thiazol-4-yl)acetate as a pale amber oil (14.51 g, 87%). To a stirred solution of this compound (14.48 g, 52.2 mmol) in N,N-dimethylformamide (125 mL) was added sodium hydride (60% dispersion in mineral oil; 6.27 g, 157 mmol), portion wise over 15 minutes. The resulting red suspension was cooled (0° C.) and treated, dropwise over 10 minutes, with iodomethane (9.80 mL, 157 mmol). The cooling bath was removed and the reaction was allowed to stir 4 hours before concentrating and partitioning the residue between ethyl acetate and water. The organic layer was washed twice more with water, dried ($Na_2SO_4$) and concentrated. The residue was purified by flash chromatography over silica using a hexane/ethyl acetate gradient to afford ethyl 2-(2-(4-methoxyphenyl)thiazol-4-yl)-2-methylpropanoate as a pale amber oil (14.12 g, 89%). To a stirred solution of this intermediate (14.12 g, 46.24 mmol) in methylene chloride (250 mL) was added boron tribromide (11.0 mL, 116 mmol), dropwise over 5 minutes. After stirring overnight, the reaction was quenched by the slow addition of methanol (~20 mL) and then concentrated. The residue was taken up in methanol (250 mL) and concentrated sulfuric acid (7.0 mL). The stirred solution was heated at reflux for 2 hours, concentrated and partitioned between ethyl acetate and aqueous sodium bicarbonate solution. The organic layer was combined with a second ethyl acetate extract of the aqueous layer, dried ($Na_2SO_4$) and concentrated to afford methyl 2-(2-(4-hydroxyphenyl)thiazol-4-yl)-2-methylpropanoate as a white solid (12.56 g, 98%). To a stirred solution of 1-bromo-3-methoxypropane (1.66 g, 10.8 mmol) in acetone (30 mL) was added the phenol intermediate (2.00 g, 7.21 mmol) and potassium carbonate (1.25 g, 9.04 mmol). The mixture was heated overnight at reflux, filtered and concentrated. The residue was purified by flash chromatography over silica using a hexane/ethyl acetate gradient to afford methyl 2-(2-(4-(3-methoxypropoxy)phenyl)thiazol-4-yl)-2-methylpropanoate as a faint amber gum (2.47 g, 98%). To a stirred solution of this compound (2.45 g, 7.01 mmol) in 1:1:1 (v/v/v) tetrahydrofuran/ethanol/water (45 mL) was added lithium hydroxide monohydrate (1.47 g, 35.0 mmol). After overnight stirring, the reaction was concentrated and partitioned between water and diethyl ether. The aqueous layer was treated with 1.0 N hydrochloric acid (40 mL) and extracted with ethyl acetate. The combined extracts were dried ($Na_2SO_4$) and concentrated to afford 2-(2-(4-(3-methoxypropoxy)phenyl)thiazol-4-yl)-2-methylpropanoic acid as a white solid (2.19 g, 40 93%). This compound and quinuclidin-3-ol were reacted according to General Procedure F to generate the title compound as a soft, faint amber solid. $^1H$ NMR (400 MHz, DMSO-$d_6$) δ 7.82 (d, J=8.9 Hz, 2H), 7.36 (br s, 1H), 7.24 (br s, 1H), 7.03 (d, J=8.9 Hz, 2H), 4.49-4.41 (m, 1H), 4.07 (t, J=6.4 Hz, 2H), 3.48 (t, J=6.4 Hz, 2H), 3.26 (s, 3H), 3.09-2.26 (m, 6H), 2.02-1.91 (m, 2H), 1.91-1.03 (m, 11H) ppm. $^{13}C$ NMR (100 MHz, DMSO-d6) δ 165.8, 162.4, 160.0, 154.6, 127.5, 126.1, 114.9, 112.1, 70.1, 68.4, 64.8, 57.9, 55.4, 53.5, 46.9, 45.9, 28.9, 28.3, 25.2, 24.2, 19.2 ppm. Purity: 100%, 100% (210 & 254 nm) UPLCMS; retention time: 0.87 min; (M+$H^+$) 460.

Quinuclidin-3-yl (2-(2-(4-(2-methoxyethoxy)phenyl) thiazol-4-yl)propan-2-yl)carbamate (Compound 20)

To a stirred solution of 2-bromoethyl methyl ether (1.88 g, 13.5 mmol) in acetone was added methyl 2-(2-(4-hydroxyphenyl)thiazol-4-yl)-2-methylpropanoate (prepared as described in Example 19, 2.00 g, 7.21 mmol) and potassium carbonate (1.56 g, 11.3 mmol). After heating at reflux overnight, the mixture was treated with additional 2-bromo ethyl methyl ether (1.88 g, 13.5 mmol) and potassium carbonate (1.56 g, 11.3 mmol). The reaction was heated at reflux for a second night, filtered and concentrated. The residue was purified by flash chromatography over silica using a hexane/ethyl acetate gradient to afford methyl 2-(2-(4-(2-methoxyethoxy)phenyl)thiazol-4-yl)-2-methylpropanoate as a white solid (2.71 g, 90%). To a stirred solution of this compound (2.71 g, 8.08 mmol) in 1:1:1 (v/v/v) tetrahydrofuran/ethanol/water (50 mL) was added lithium hydroxide monohydrate (1.70 g, 40.5 mmol). After overnight stirring, the reaction was concentrated and partitioned between water and diethyl ether. The aqueous layer was treated with 1.0 N hydrochloric acid (41 mL) and extracted with ethyl acetate. The combined extracts were dried ($Na_2SO_4$) and concentrated to afford 2-(2-(4-(2-methoxyethoxy)phenyl)thiazol-4-yl)-2-methylpropanoic acid as a white solid (2.57 g, 99%). This compound and quinuclidin-3-ol were reacted according to General Procedure F to generate the title compound as a pale amber solid. $^1H$ NMR (400 MHz, DMSO-$d_6$) δ 7.82 (d, J=8.8 Hz, 2H), 7.36 (br s, 1H), 7.24 (br s, 1H), 7.04 (d, J=8.8 Hz, 2H), 4.49-4.41 (m, 1H), 4.19-4.12 (m, 2H), 3.71-3.65 (m, 2H), 3.32 (s, 3H), 3.11-2.87 (m, 1H), 2.86-2.19 (m, 5H), 1.92-1.16 (m, 11H) ppm. $^{13}C$ NMR (100 MHz, DMSO-$d_6$) δ 165.7, 162.9, 159.9, 154.6, 127.5, 126.2, 114.9, 112.2, 70.3, 70.1, 67.1, 58.2, 55.4, 53.5, 46.9, 45.9, 28.3, 25.2, 24.3, 19.2 ppm. Purity: 100%, 100% (210 & 254 nm) UPLCMS; retention time: 0.85 min; (M+$H^+$) 446.

Quinuclidin-3-yl 2-(5-(4-(2-methoxyethoxy)phenyl) pyridin-2-yl)propan-2-ylcarbamate (Compound 21)

Using General Procedure E and the reaction inputs 5-bromopicolinonitrile and 2-(4-(2-methoxyethoxy)phenyl)-4,4,5,5-tetramethyl-1,3,2-dioxaborolane, 5-(4-(2-methoxyethoxy)phenyl)picolinonitrile was prepared. Cerium trichloride (8.05 g, 21.6 mmol) was loaded into a flask and dried by heating (170° C.) under vacuum for 3 hours. The solid was taken up in tetrahydrofuran (20 mL) and stirred vigorously for 30 minutes. The suspension was cooled to −78° C. and treated, dropwise, with a 3.0 M solution of methyllithium in diethyl ether (7.2 mL, 21.6 mmol). Following addition, the reaction was stirred at −78° C. for 1 hour before adding a solution of the above aryl borate (1.83 g, 7.20 mmol) in tetrahydrofuran (20 mL). The mixture was maintained at −78° C. for 2 hours and then allowed to warm to room temperature. At this time, the reaction was quenched by the addition of aqueous ammonium hydroxide (10 mL) and filtered through a plug of Celite. The filtrate was extracted with ethyl acetate and the combined extracts were washed with brine, dried ($Na_2SO_4$) and concentrated. The residue was purified by flash chromatography over silica using ethyl acetate eluent to afford 2-(5-(4-(2-methoxyethoxy)phenyl)pyridin-2-yl)propan-2-amine as a yellow solid (0.800 g, 39%). To a stirred suspension of this intermediate (0.500 g, 1.75 mmol) in water (10 mL) and concentrated hydrochloric acid (0.44 mL) was added toluene (10 mL). The mixture was cooled (0° C.) and treated with, simultaneously over 1 hour, solutions of triphosgene (0.776 g, 2.62 mmol) in toluene (10 mL) and sodium bicarbonate (2.2 g, 26 mmol) in water (20 mL). Following the additions, the reaction was stirred for an additional 30 minutes before the upper toluene layer was removed and dried (N $a_2SO_4$). At the same time, a stirred solution of quinuclidin-3-ol (0.445 g, 3.64 mmol) in tetrahydrofuran (10 mL) was treated with sodium hydride (60% dispersion in mineral oil; 0.154 g, 3.85 mmol). This mixture was stirred for 5 minutes and then added to the solution of crude isocyanate in toluene. The reaction was stirred for 10 minutes, quenched with the addition of brine (5 mL) and extracted with ethyl acetate. The combined extracts were dried ($Na_2SO_4$) and concentrated. The residue was purified by flash chromatography over reversed phase silica to afford the title compound as a light yellow solid (0.100 g, 13%). $^1H$ NMR (500 MHz, $CDCl_3$) δ 8.70-8.70 (d, J=2.0 Hz, 1H), 7.83-7.81 (m, 1H), 7.49-7.47 (d, J=9.0 Hz, 2H), 7.45-7.43 (d, J=8.0 Hz, 1H), 7.03-7.01 (d, J=8.5 Hz, 2H), 6.63 (br s, 1H), 4.68-4.66 (m, 1H), 4.16 (t, J=5.0 Hz, 2H), 3.77 (t, J=5.0 Hz, 2H), 3.45 (s, 3H), 3.19-2.70 (m, 6H), 2.15-1.89 (m, 2H), 1.76 (s, 6H), 1.73-1.36 (m, 3H) ppm. $^{13}C$ NMR (125 MHz, $CDCl_3$) δ 162.7, 158.9, 154.9, 145.9, 134.8, 134.3, 130.1, 128.1, 119.2, 115.2, 71.0, 70.8, 67.4, 59.2, 55.9, 55.7, 47.4, 46.5, 46.4, 27.9, 25.4, 24.6, 19.5 ppm. Purity: >99% (214 & 254 nm) LCMS; retention time: 1.32 min; (M+$H^+$) 440.2.

Quinuclidin-3-yl (2-(4'-(3-cyanopropoxy)-[1,1'-biphenyl]-4-yl)propan-2-yl)carbamate (Compound 22)

To a stirred solution of 4-bromophenol (17.1 g, 98.8 mmol) in acetonitrile (150 mL) was added 1-bromobutylnitrile (12.3 mL, 124 mmol) and potassium carbonate (15.0 g, 109 mmol). The mixture was heated to reflux overnight, cooled and concentrated. The residue was taken up in water and extracted with ethyl acetate. The combined extracts were dried ($Na_2SO_4$) and concentrated and the crude material was purified by flash chromatography over silica using a hexane/ethyl acetate eluent to afford 4-(4-bromophenoxy) butanenitrile as a white solid (20.8 g, 88%). To a stirred solution of this product in N,N-dimethylformamide (100 mL), was added bis(pinacolato)diboron (4.60 g, 18.1 mmol), potassium acetate (7.41 g, 75.5 mmol) and [1,1'-bis(diphenylphosphino)ferrocene]-dichloropalladium(II) complex with dichloromethane (0.616 g, 1.04 mmol). The mixture was heated to reflux overnight and then concentrated. The residue was taken up in ethyl acetate and washed with water and brine. The organic layer was dried ($Na_2SO_4$) and concentrated and the crude product was purified by flash chromatography over silica using a hexane/ethyl acetate eluent to afford 4-(4-(4,4,5,5-tetramethyl-1,3,2-dioxaborolan-2-yl) phenoxy)butanenitrile as a white solid (3.43 g, 79%). This product and quinuclidin-3-yl (2-(4-bromophenyl)propan-2-yl)carbamate (prepared by reacting quinuclidin-3-ol and 2-(4-bromophenyl)propan-2-amine using General Procedure F) were reacted according to General Procedure E to generate the title compound as a white solid. $^1$H NMR (400 MHz, DMSO-$d_6$) δ 7.67-7.26 (m, 7H), 7.02 (d, J=8.8 Hz, 2H), 4.50-4.33 (m, 1H), 4.08 (t, J=6.0 Hz, 2H), 3.14-2.18 (m, 8H), 2.04 (quin, J=6.7 Hz, 2H), 1.94-1.70 (m, 11H) ppm. $^{13}$C NMR (100 MHz, DMSO-$d_6$) δ 157.7, 154.5, 146.8, 137.4, 132.7, 127.6, 125.7, 125.2, 120.2, 114.9, 70.0, 65.8, 55.4, 54.2, 46.9, 45.9, 29.4, 25.3, 24.7, 24.2, 19.2, 13.4 ppm. Purity: 100%, 98.9% (210 & 254 nm) UPLCMS; retention time: 0.88 min; (M+H$^+$) 448.6.

Quinuclidin-3-yl (2-(4'-(cyanomethoxy)-[1,1'-biphenyl]-4-yl)propan-2-yl)carbamate (Compound 23)

Using General Procedure E and the reaction inputs quinuclidin-3-yl (2-(4-bromophenyl)propan-2-yl)carbamate (prepared by reacting quinuclidin-3-ol and 2-(4-bromophenyl)propan-2-amine using General Procedure F) and 4-(cyanomethoxy)phenylboronic acid, the title compound was prepared as a pale amber solid. $^1$H NMR (400 MHz, DMSO-$d_6$) δ 7.65 (d, J=8.2 Hz, 2H), 7.60-7.31 (m, 5H), 7.15 (d, J=8.9 Hz, 2H), 5.21 (s, 2H), 4.53-4.30 (m, 1H), 3.18-2.19 (m, 6H), 2.05-1.18 (m, 11H) ppm. $^{13}$C NMR (100 MHz, DMSO-$d_6$) δ 155.8, 154.6, 147.2, 137.2, 134.4, 127.8, 126.0, 125.3, 116.7, 115.3, 70.0, 55.4, 54.2, 53.5, 46.9, 45.9, 29.4, 25.2, 24.2, 19.2 ppm. Purity: 100%, 100% (210 & 254 nm) UPLCMS; retention time: 0.85 min; (M+H$^+$) 420.3.

Example 2: Preparation of (S)-Quinuclidin-3-yl (2-(2-(4-fluorophenyl)thiazol-4-yl)propan-2-yl)carbamate free base Step 1: Dimethylation with methyl iodide

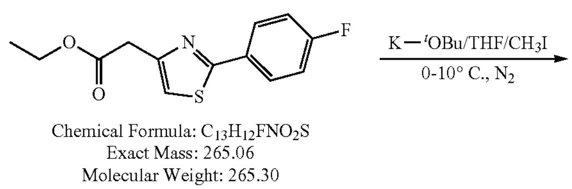

Chemical Formula: $C_{13}H_{12}FNO_2S$
Exact Mass: 265.06
Molecular Weight: 265.30

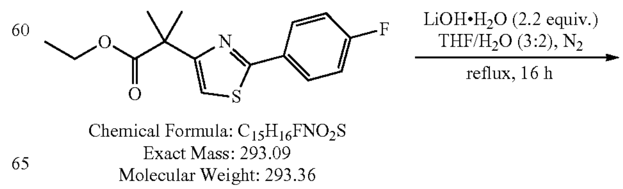

Chemical Formula: $C_{15}H_{16}FNO_2S$
Exact Mass: 293.09
Molecular Weight: 293.36

-continued

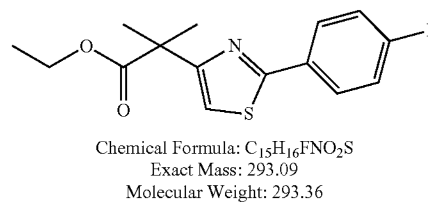

Chemical Formula: $C_{15}H_{16}FNO_2S$
Exact Mass: 293.09
Molecular Weight: 293.36

A 3N RB flask was equipped with a thermometer, an addition funnel and a nitrogen inlet. The flask was flushed with nitrogen and potassium tert-butoxide (MW 112.21, 75.4 mmol, 8.46 g, 4.0 equiv., white powder) was weighed out and added to the flask via a powder funnel followed by the addition of THF (60 mL). Most of the potassium tert-butoxide dissolved to give a cloudy solution. This mixture was cooled in an ice-water bath to 0-2° C. (internal temperature). In a separate flask, the starting ester (MW 265.3, 18.85 mmol, 5.0 g, 1.0 equiv.) was dissolved in THF (18 mL+2 mL as rinse) and transferred to the addition funnel. This solution was added dropwise to the cooled mixture over a period of 25-30 min, keeping the internal temperature below 5° C. during the addition. The reaction mixture was cooled back to 0-2° C. In a separate flask, a solution of methyl iodide (MW 141.94, 47.13 mmol, 6.7 g, 2.5 equiv.) in THF (6 mL) was prepared and transferred to the addition funnel. The flask containing the methyl iodide solution was then rinsed with THF (1.5 mL) which was then transferred to the addition funnel already containing the clear colorless solution of methyl iodide in THF. This solution was added carefully dropwise to the dark brown reaction mixture over a period of 30-40 min, keeping the internal temperature below 10° C. at all times during the addition. After the addition was complete, the slightly turbid mixture was stirred for an additional 1 h during which time the internal temperature dropped to 0-5° C. After stirring for an hour at 0-5° C., the reaction mixture was quenched with the slow dropwise addition of 5.0M aqueous HCl (8 mL) over a period of 5-7 min. The internal temperature was maintained below 20° C. during this addition. After the addition, water (14 mL) was added and the mixture was stirred for 2-3 min. The stirring was stopped and the two layers were allowed to separate. The two layers were then transferred to a 250 mL 1N RB flask and the THF was evaporated in vacuo as much as possible to obtain a biphasic layer of THF/product and water. The two layers were allowed to separate. A THF solution of the Step 1 product was used in the next reaction.

Step 2: Hydrolysis of the Ethyl Ester with LiOH Monohydrate

-continued

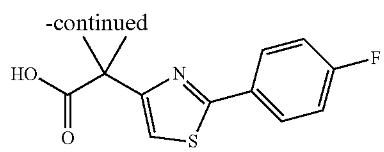

Chemical Formula: $C_{13}H_{12}FNO_2S$
Exact Mass: 265.06
Molecular Weight: 265.30

The crude ester in THF was added to the reaction flask. Separately, $LiOH \cdot H_2O$ (MW 41.96, 75.0 mmol, 3.15 grams, 2.2 equiv.) was weighed out in a 100 mL beaker to which a stir bar was added. Water (40 mL) was added and the mixture was stirred till all the solid dissolved to give a clear colorless solution. This aqueous solution was then added to the 250 mL RB flask containing the solution of the ester in tetrahydrofuran (THF). A condenser was attached to the neck of the flask and a nitrogen inlet was attached at the top of the condenser. The mixture was heated at reflux for 16 hours. After 16 hours, the heating was stopped and the mixture was cooled to room temperature. The THF was evaporated in vacuo to obtain a brown solution. An aliquot of the brown aqueous solution was analyzed by HPLC and LC/MS for complete hydrolysis of the ethyl ester. Water (15 mL) was added and this aqueous basic solution was extracted with TBME (2×40 mL) to remove the t-butyl ester. The aqueous basic layer was cooled in an ice-water bath to 0-10° C. and acidified with dropwise addition of concentrated HCl to pH~1 with stirring. To this gummy solid in the aqueous acidic solution was added TBME (60 mL) and the mixture was shaken and then stirred vigorously to dissolve all the acid into the TBME layer. The two layers were transferred to a separatory funnel and the TBME layer was separated out. The pale yellow aqueous acidic solution was re-extracted with TBME (40 mL) and the TBME layer was separated and combined with the previous TBME layer. The aqueous acidic layer was discarded. The combined TBME layers are dried over anhydrous $Na_2SO_4$, filtered and evaporated in vacuo to remove TBME and obtain the crude acid as an orange/dark yellow oil that solidified under high vacuum to a dirty yellow colored solid. The crude acid was weighed out and crystallized by heating it in heptane/TBME (3:1, 5 mL/g of crude) to give the acid as a yellow solid.

Step 3: Formation of Hydroxamic Acid with $NH_2OH \cdot HCl$

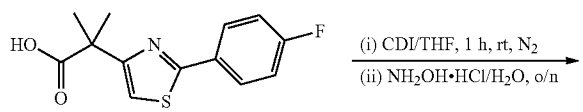

Chemical Formula: $C_{13}H_{12}FNO_2S$
Exact Mass: 265.06
Molecular Weight: 265.30

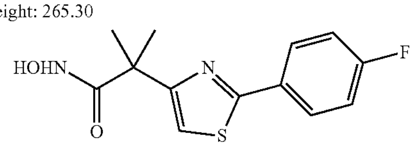

Chemical Formula: $C_{13}H_{13}FN_2O_2S$
Exact Mass: 280.07
Molecular Weight: 280.32

The carboxylic acid (MW 265.3, 18.85 mmol, 5.0 g, 1.0 equiv.) was weighed and transferred to a 25 mL 1N RB flask under nitrogen. THF (5.0 mL) was added and the acid readily dissolved to give a clear dark yellow to brown solution. The solution was cooled to 0-2° C. (bath temperature) in an ice-bath and N, N'-carbonyldiimidazole (CDI; MW 162.15, 20.74 mmol, 3.36 g, 1.1 equiv.) was added slowly in small portions over a period of 10-15 minutes. The ice-bath was removed and the solution was stirred at room temperature for 1 h. After 1 h of stirring, the solution was again cooled in an ice-water bath to 0-2° C. (bath temperature). Hydroxylamine hydrochloride ($NH_2OH \cdot HCl$; MW 69.49, 37.7 mmol, 2.62 g, 2.0 equiv.) was added slowly in small portions as a solid over a period of 3-5 minutes as this addition was exothermic. After the addition was complete, water (1.0 mL) was added to the heterogeneous mixture dropwise over a period of 2 minutes and the reaction mixture was stirred at 0-10° C. in the ice-water bath for 5 minutes. The cooling bath was removed and the reaction mixture was stirred under nitrogen at room temperature overnight for 20-22 h. The solution became clear as all of the $NH_2OH \cdot HCl$ dissolved. After 20-22 h, an aliquot of the reaction mixture was analyzed by High Pressure Liquid Chromatography (HPLC). The THF was then evaporated in vacuo and the residue was taken up in dichloromethane (120 mL) and water (60 mL). The mixture was transferred to a separatory funnel where it was shaken and the two layers allowed to separate. The water layer was discarded and the dichloromethane layer was washed with 1N hydrochloride (HCl; 60 mL). The acid layer was discarded. The dichloromethane layer was dried over anhydrous $Na_2SO_4$, filtered and the solvent evaporated in vacuo to obtain the crude hydroxamic acid as a pale yellow solid that was dried under high vacuum overnight.

Step 3 Continued: Conversion of Hydroxamic Acid to Cyclic Intermediate (not Isolated)

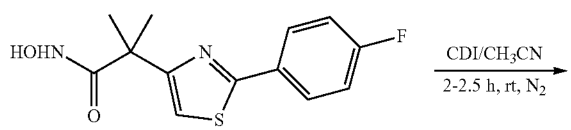

Chemical Formula: $C_{13}H_{13}FN_2O_2S$
Exact Mass: 280.07
Molecular Weight: 280.32

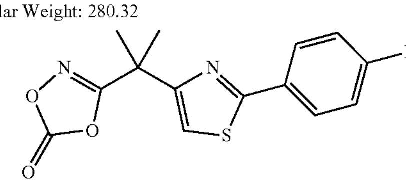

Chemical Formula: $C_{14}H_{11}FN_2O_3S$
Exact Mass: 306.05
Molecular Weight: 306.31

The crude hydroxamic acid (MW 280.32, 5.1 g) was transferred to a 250 mL 1N RB flask with a nitrogen inlet. A stir bar was added followed by the addition of acetonitrile (50 mL). The solid was insoluble in acetonitrile. The yellow heterogeneous mixture was stirred for 2-3 minutes under nitrogen and CDI (MW 162.15, 20.74 mmol, 3.36 g, 1.1 equiv.) was added in a single portion at room temperature. No exotherm was observed. The solid immediately dissolved and the clear yellow solution was stirred at room temperature for 2-2.5 h. After 2-2.5 h, an aliquot was analyzed by HPLC and LC/MS which showed conversion of the hydroxamic acid to the desired cyclic intermediate.

The acetonitrile was then evaporated in vacuo to give the crude cyclic intermediate as reddish thick oil. The oil was taken up in toluene (60 mL) and the reddish mixture was heated to reflux for 2 hours during which time, the cyclic intermediate released $CO_2$ and rearranged to the isocyanate (see below).

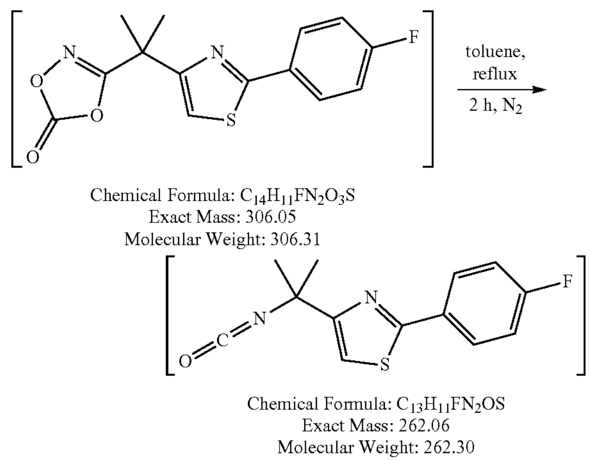

Chemical Formula: $C_{14}H_{11}FN_2O_3S$
Exact Mass: 306.05
Molecular Weight: 306.31

Chemical Formula: $C_{13}H_{11}FN_2OS$
Exact Mass: 262.06
Molecular Weight: 262.30

Step 3 Continued: Conversion of the Isocyanate to the Free Base

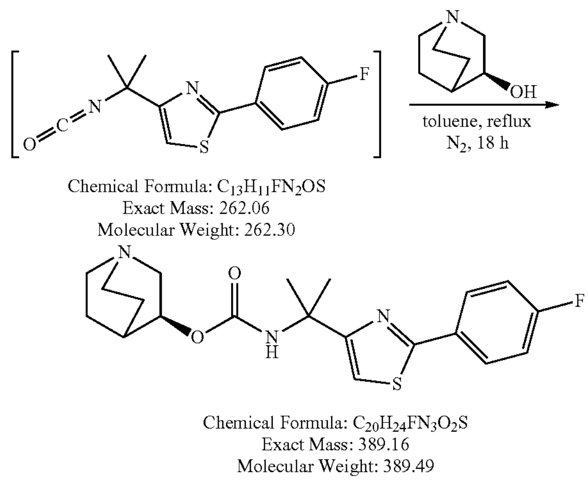

Chemical Formula: $C_{13}H_{11}FN_2OS$
Exact Mass: 262.06
Molecular Weight: 262.30

Chemical Formula: $C_{20}H_{24}FN_3O_2S$
Exact Mass: 389.16
Molecular Weight: 389.49

The reaction mixture was cooled to 50-60° C. and (S)-(+)-quinuclidinol (MW 127.18, 28.28 mmol, 3.6 g, 1.5 equiv.) was added to the mixture as a solid in a single portion. The mixture was re-heated to reflux for 18 h. After 18 h, an aliquot was analyzed by HPLC and LC/MS which showed complete conversion of the isocyanate to the desired product. The reaction mixture was transferred to a separatory funnel and toluene (25 mL) was added. The mixture was washed with water (2×40 mL) and the water layers were separated. The combined water layers were re-extracted with toluene (30 mL) and the water layer was discarded. The combined toluene layers were extracted with 1N HCl (2×60 mL) and the toluene layer (containing the O-acyl impurity) was discarded. The combined HCl layers were transferred to a 500 mL Erlenmeyer flask equipped with a stir bar. This stirring clear yellow/reddish orange solution was basified to pH 10-12 by the dropwise addition of 50% w/w aqueous NaOH. The desired free base precipitated out of solution as a dirty yellow gummy solid which could trap the stir bar. To this mixture was added isopropyl acetate (100 mL) and the mixture was stirred vigorously for 5 minutes when the gummy solid went into isopropyl acetate. The stirring was stopped and the two layers were allowed to separate. The yellow isopropyl acetate layer was separated and the basic aqueous layer was re-extracted with isopropyl acetate (30 mL). The basic aqueous layer was discarded and the combined isopropyl acetate layers were dried over anhydrous $Na_2SO_4$, filtered into a pre-weighed RB flask and the solvent evaporated in vacuo to obtain the crude free base as beige to tan solid that was dried under high vacuum overnight.

Step 3 Continued: Recrystallization of the Crude Free Base

The beige to tan colored crude free base was weighed and re-crystallized from heptane/isopropyl acetate (3:1, 9.0 mL of solvent/g of crude free base). The appropriate amount of heptane/isopropyl acetate was added to the crude free base along with a stir bar and the mixture was heated to reflux for 10 min (free base was initially partially soluble but dissolved to give a clear reddish orange solution when heated to reflux). The heat source was removed and the mixture was allowed to cool to room temperature with stirring when a white precipitate formed. After stirring at room temperature for 3-4 h, the precipitate was filtered off under hose vacuum using a Buchner funnel, washed with heptane (20 mL) and dried under hose vacuum on the Buchner funnel overnight. The precipitate was the transferred to a crystallizing dish and dried at 55° C. overnight in a vacuum oven. $^1H$ NMR (400 MHz, $CDCl_3$) δ 8.04-7.83 (m, 2H), 7.20-6.99 (m, 3H), 5.53 (s, 1H), 4.73-4.55 (m, 1H), 3.18 (dd, J=14.5, 8.4 Hz, 1H), 3.05-2.19 (m, 5H), 2.0-1.76 (m, 11H) ppm. $^{13}C$ NMR (100 MHz, $CDCl_3$) δ 166.38, 165.02, 162.54, 162.8-155.0 (d, C—F), 130.06, 128.43, 128.34, 116.01, 115.79, 112.46, 71.18, 55.70, 54.13, 47.42, 46.52, 27.94, 25.41, 24.67, 19.58 ppm.

Example 3: Preparation of Crystalline Forms of (S)-Quinuclidin-3-yl (2-(2-(4-fluorophenyl)thiazol-4-yl)propan-2-yl)carbamate Salts Crystalline salts of (S)-Quinuclidin-3-yl (2-(2-(4-fluorophenyl)thiazol-4-yl)propan-2-yl)carbamate may be formed from the free base prepared as described in Example 23.

For example, the free base of (S)-Quinuclidin-3-yl (2-(2-(4-fluorophenyl)thiazol-4-yl)propan-2-yl)carbamate (about 50 mmol) is dissolved IPA (140 ml) at room temperature and filtered. The filtrate is added into a 1 L r.b. flask which is equipped with an overhead stirrer and nitrogen in/outlet. L-malic acid (about 50 mmol) is dissolved in IPA (100+30 ml) at room temperature and filtered. The filtrate is added into the above 1 Liter flask. The resulting solution is stirred at room temperature (with or without seeding) under nitrogen for 4 to 24 hours. During this period of time crystals form. The product is collected by filtration and washed with a small amount of IPA (30 ml). The crystalline solid is dried in a vacuum oven at 55° C. for 72 hours to yield the desired malate salt.

Crystal forms of other salts, e.g. acid addition salts with succinic acid or HCl, may be prepared in an analogous manner.

Example 4: In-Vitro GCS Inhibition (Compound 2 and Analogs)

Inhibition of glucosylceramide synthase activity can be measured with one or more assays. A first assay is a microsomal assay that directly measures the conversion of ceramide to glucosylceramide by HPLC. Microsomes are a source of glucosylceramide synthase activity in the microsomal assay. A second assay is a cell based, phenotypic assay that monitors cell surface expression of the downstream lipid GM3 by antibody mediated immunofluorescence. Specific protocols are provided below.

Glucosylceramide Synthase Activity Microsomal Assay:

An enzyme assay using microsomes as a source of glucosylceramide synthase activity. Fluorescent ceramide substrate is delivered to membrane-bound enzyme as a complex with albumin. After reaction, ceramide and glucosylceramide are separated and quantitated by reverse-phase HPLC with fluorescence detection. Enzymatic activity is assessed using a fluorescent labeled substrate and microsomes as a source of glucosylceramide synthase. $C_6$-NBD-Ceramide is complexed with albumin for delivery to microsomes that are isolated according to the procedure described below. The final concentration of $C_6$-NBD-Ceramide in the stock solution is 0.5 mM; the final concentration of BSA is 0.5 mM. Separation and quantitation of substrate and product (glucosylceramide) are achieved by reverse-phase HPLC with fluorescence detection.

Preparation of Microsomes from A375 Human Melanoma Cells;

Microsomes are isolated from A375 human melanoma cells. Eight to ten million cells are harvested by trypsinization and washed with ice cold PBS. Cells are resuspended in ice-cold lysis buffer containing protease inhibitors. Cell lysate is sonicated on ice using a probe sonicator. After sonication, the cell lysate is separated from debris by centrifugation at 10,000 g for 10 minutes at 4° C. The supernatant is removed and cleared by additional centrifugation at 100,000 g for 1 hour at 4° C. The pellet is then resuspended in the lysis buffer, aliquoted and stored at −80° C. prior to use.

Glucosylceramide Synthase Assay

To determine glucosylceramide synthase inhibition, substrates at 2× of their Km (fluorescent ceramide and UDP-glucose, 3 μM and 4 μM respectively) and microsomes (1:50 dilution) are combined 1:1 and incubated at room temperature for 1 hour in the dark on a plate shaker. The reaction is stopped by the addition of 150 μL of 100 μM $C_8$-ceramide in 50% aq. isopropanol; 10 μL of the final mix is analyzed on HPLC (with fluorescence detector). The mobile phase is 1% formic acid added to 81% methanol/19% water with flow rate 0.5 mL/min. Fluorescence is detected with $\lambda_{ex}$=470 nm and $\lambda_{em}$=530 nm. Under these conditions, NBD-$C_6$-GluCer had a retention time of about 1.7 min and NBD-$C_6$-Cer elutes from the column after about 2.1 min. Both peaks are separated from each other and the baseline and were integrated automatically by the HPLC software. The percent conversion of substrate to product is used as the readout for inhibitor testing.

GM3 Fluorescent-Linked Immunosorbent Assay (FLISA):

This is a phenotypic assay that measures GM3 expression in B16 mouse melanoma or C32 human melanoma cells following treatment with test compounds. Cell surface GM3 expression is determined by antibody mediated fluorescence.

Compounds are diluted in media and plated in 384 well plates in DMSO. B16 and C32 cells are assayed at densities of 20,000 cells/ml and 62,500 cells/ml, respectively, per well. Each titration curve contains 10 points that are assayed in duplicate on each test run. The plates are incubated for 48 hours at 37° C., 5% CO2, and are then washed once with TBS. Anti-GM3 antibody is added to each well and the plates are then incubated for an additional one hour at room temperature. Plates are subsequently washed twice and incubated for an additional hour with the labeled secondary antibody. Following the final incubation, the plates are washed twice and the fluorescence at $\lambda_{ex}$=D640/20 nm and $\lambda_{em}$=657 nm is detected on a fluorescent reader.

Assay Results

Individual assay results of certain exemplified compounds in these assays are presented in the Table below. The results of the microsomal assays are expressed as "GCS $IC_{50}$", which represents the concentration of the compound causing 50% inhibition of glucosylceramide synthase activity. The results of the cell-based assays are expressed as "GM3 B16 $IC_{50}$" or "GM3 C32 $IC_{50}$" for the B16 assay and the C32 assay, respectively. These values represent the concentration of the compound causing 50% inhibition of GM3 expression on the cell surface.

| Compound No. | GCS $IC_{50}$ (mM) | GM3 B16 $IC_{50}$ (mM) | GM3 C32 $IC_{50}$ (mM) |
|---|---|---|---|
| 1 | 0.0019 | 0.0156 | 0.0021 |
| 2 | 0.0601 | 0.1068 | 0.0096 |
| 3 | 0.00414 | 0.0437 | 0.00131 |
| 4 | 0.0015 | 0.0116 | 0.0008 |
| 5 | 0.0012 | 0.0193 | 0.0003 |
| 6 | 0.0028 | 0.0181 | 0.0006 |
| 7 | 0.0014 | 0.0081 | 0.0004 |
| 8 | 0.0010 | 0.0075 | 0.0004 |
| 9 | 0.0014 | 0.0168 | 0.0004 |
| 10 | 0.0064 | 0.0213 | 0.0022 |
| 11 | 0.0149 | 0.0819 | 0.0018 |
| 12 | 0.0203 | 0.0878 | 0.0037 |
| 13 | 0.0035 | 0.0386 | 0.0007 |
| 14 | 0.0104 | 0.1096 | 0.0053 |
| 15 | 0.0267 | 0.0295 | 0.0049 |
| 16 | 0.0024 | 0.0666 | 0.0016 |
| 17 | 0.4544 | 0.8786 | 0.0216 |
| 18 | 0.1480 | 0.6555 | 0.0223 |
| 19 | 0.1701 | 0.1972 | 0.0426 |
| 20 | 0.3601 | 0.1065 | 0.0198 |
| 21 | 0.0506 | 0.2658 | 0.0111 |
| 22 | 0.0096 | 0.0865 | 0.0032 |
| 23 | 0.0026 | 0.0477 | 0.0008 |

These comparative results demonstrate that compounds according to the present disclosure have comparable in-vitro activity as inhibitors of GCS, and as a result, are expected to demonstrate similar in-vivo benefits.

Example 5: Clinical Study of Compound 2 in GD-3 Patients

A 156-week, multi-part, open-label, multinational study of the safety, tolerability, pharmacokinetics, pharmacodynamics, and exploratory efficacy of Compound 2 in combination with imiglucerase in adult patients with Gaucher disease Type 3 stabilized with imiglucerase was initiated.

Patients 18 years of age or older with a clinical diagnosis of GD3 and documented deficiency of acid beta-glucosidase activity having received treatment with ERT for at least 3 years and with imiglucerase (Cerezyme) at a stable monthly dose for at least 6 months prior to enrollment were included in the study. Patients must have reached the following GD therapeutic goals: hemoglobin level of ≥11.0 g/dL for females and ≥12.0 g/dL for males; platelet count ≥100 000/mm3; spleen volume <10 multiples of normal (MN), or total splenectomy (provided the splenectomy occurred >3 years prior to randomization); liver volume <1.5 MN; and no bone crisis and free of symptomatic bone disease such as bone pain attributable to osteonecrosis and/or pathological fractures within the last year. Patients must have GD3 featuring oculomotor apraxia (supranuclear gaze palsy) characterized by a horizontal saccade abnormality.

(A) 26-Week Interim Analysis

An interim analysis was performed when 5 patients had completed 26 weeks of concurrent treatment with (1) imiglucerase (Cerezyme from Sanofi Genzyme) under each patient's established regimen, and (2) Compound 2 administered orally at 15 mg/day in a single dose. During the study patients were evaluated for safety and tolerability, CSF and plasma biomarkers (glucosylceramide, GL-1; glucosylsphingosine, lyso-GL1), pharmacokinetics, markers for systemic disease (spleen and liver volume measured by magnetic resonance imaging (MRI), platelet count, hemoglobin levels), indicia of interstitial lung disease (high resolution pulmonary computed tomography (CT)), and horizontal saccadic eye movement.

At baseline, four patients had mild neurological involvement and one had moderate neurological involvement, as measured using the Modified Severity Scoring Tool (mSST; Davies, et al., 2011). All patients showed evidence of interstitial lung disease based on chest CT. One patient had anemia, as evidenced by a plasma hemoglobin level of 10.6 g/dL.

All patients reported no serious or lasting treatment-emergent adverse events. The most frequently reported events were headache and backache, and these were only considered mild to moderate and transient in duration (likely related to lumbar puncture performed for CSF testing).

It was found that Compound 2 effectively cross the blood-brain barrier in all patients, as demonstrated in the Table below:

| Compound 2 in plasma | Day 1 (N = 5) |
|---|---|
| $AUC_{0\_24}$, ng · h/mL (mean ± SD) | 715 ± 225 |
| $C_{max}$, ng/mL (mean ± SD) | 48.2 ± 19.2 |
| $t_{max}$, h (median) | 2.00 |

| Compound 2 in CSF | Week 4 (N = 5) | Week 26 (N = 4) |
|---|---|---|
| Concentration 4 hours post dose, ng/mL (mean ± SD) | 4.17 ± 0.83 | 4.71 ± 2.50 |

The higher variability of CSF concentration of Compound 2 seen at 26 weeks is attributed to a reduction in exposure of one of the patients (Patient 5) at weeks 12 to 26 for unknown reasons. Patient 1 was excluded from the Week 26 CSF determination because of an error in sample collection.

It was found that there were significant improvements in plasma and CSF biomarkers for GD-3 at 26 weeks. At baseline, the mean (±SD) GL-1 concentration in CSF was 7.1±2.8 ng/mL (range 4.4-11.1 ng/mL), while the mean (±SD) lyso-GL-1 concentration in CSF was 39.3±22.9 pg/mL (range 20.1-67.6 pg/mL). For comparison, the healthy GL-1 concentration in CSF is 4.5-5.9 ng/mL, and the healthy level of lyso-GL-1 in CSF is less than 5.0 pg/mL. At 4 weeks and at 26 weeks, individual reductions in the CSF biomarkers was found to be as follows (shown as percent reduction from the baseline CSF concentration):

| | Patient 1 | Patient 2 | Patient 3 | Patient 4 | Patient 5 | Mean (n = 4)* |
|---|---|---|---|---|---|---|
| GL-1 at 4 weeks | −86% | −55% | −53% | −62% | −36% | −64% |
| GL-1 at 26 weeks | −86% | −78% | −58% | −78% | +4% | −75% |
| Lyso-GL1 at 4 weeks | −38% | −16% | −34% | −39% | −11% | −32% |
| Lyso-GL1 at 26 weeks | −52% | −42% | −41% | −57% | +94% | −48% |

*Excludes Patient 5, who showed reduced exposure on PK analysis of week 12-26 results Severity of interstitial lung disease was characterized by the percent of lung volume affect by ILD as measured by high-resolution CT in four lung regions (aortic arch, carina, lower zone L3, lower zone L4). Patients were rated as having severe ILD (51-100% of lung volume affected), moderate ILD (26-50% of lung volume affected), mild ILD (1-25% of lung volume affected) or normal (0% of lung volume showing ILD). All patients showed ILD at baseline, and 4 out of 5 patients showed regression of ILD after 26 weeks of treatment (patient 5 showed slight progression of ILD):

| | | Aortic Arch | | Carina | | Zone L3 | | Zone L4 | |
|---|---|---|---|---|---|---|---|---|---|
| | | Left | Right | Left | Right | Left | Right | Left | Right |
| Patient 1 | Initial | Mild | Mild | Mild | Mild | Norm | Norm | Mild | Mild |
| | Week 26 | Norm | Norm | Norm | Norm | Norm | Norm | Norm | Norm |
| Patient 2 | Initial | Mild | Mild | Mild | Mild | Mild | Norm | Mod | Mod |
| | Week 26 | Norm | Norm | Norm | Mild | Norm | Norm | Norm | Norm |
| Patient 3 | Initial | Mild | Mild | Mod | Mild | Severe | Mod | Severe | Severe |
| | Week 26 | Norm | Norm | Norm | Norm | Mild | Mild | Mod | Mod |
| Patient 4 | Initial | Norm | Mild | Norm | Norm | Norm | Norm | Norm | Norm |
| | Week 26 | Norm | Norm | Norm | Norm | Norm | Norm | Norm | Norm |
| Patient 5 | Initial | Mild | Mild | Mild | Mild | Mild | Mild | Mild | Mild |
| | Week 26 | Mild | Mild | Mild | Mod | Mild | Mild | Mod | Mod |

All patients showed an absence of systemic deterioration. Two patients showed reductions in splenic volume of 10% or more. There were no clinically meaningful changes in hemoglobin levels. On average, platelet counts rose 17% from baseline to week 26, and the three patients with lowest baseline platelet counts showed individual increase at 26 weeks of 23-42%. Individual patient data for platelet counts are shown in the table below (shown as $10^9$ platelets/L):

| | Patient 1 | Patient 2 | Patient 3 | Patient 4 | Patient 5 |
|---|---|---|---|---|---|
| Screening | 192 | 207 | 259* | 313 | 149 |
| Day 1 | 186* | 192* | n/a | 307* | 127* |
| Week 4 | 203 | 243 | 247 | 239 | 154 |
| Week 12 | 214 | 294 | 264 | 314 | 180 |
| Week 26 | 264 | 236 | 248 | 267 | 173 |
| % Change from baseline to 26 weeks | +42% | +23% | −4.3% | −13% | +36% |

*indicates figure used as baseline

Quantification of horizontal and vertical saccadic eye movements (HSEM and VSEM, respectively) was performed in all 5 patients. In the five patients, mean peak velocity (PV) of horizontal rightward 150 saccades was 50.8°/s (+/−8.1°/s) at baseline and 47.5 V/min (+/−12.6°/s) at Week 26: and the mean PV of horizontal leftward 150 saccades was 44.7°/s (+/−17.9°/s) at baseline and 32.3°/s (+/−15.9°/s) at Week 26. A slower velocity implies a more significant degree of neurological impairment. The mean PV of horizontal rightward 300 saccades was 77.7°/s (+/−16.4°/s) at baseline and 68.1°/min (+/−24.7°/s) at Week 26; and the mean PV of horizontal leftward 300 saccades was 58.7°/s (+/−21.5°/s) at baseline and 49.9°/s (+/−8.5°/s) at Week 26. The normal range for 150 and 300 horizontal saccades has previously been reported as >200°/s and >400°/s (Bremova-Ertl et al, 2018). In summary, no clinically meaningful changes in HSEM were observed over the 26-week treatment period. As with HSEM, VSEM measurements were stable between baseline and week 26.

Four exploratory biomarkers were quantified in plasma, serum and/or CSF of GD3 patients at week 4 and week 26: chitotriosidase (CHITO; an enzyme known to be elevated in GD patients) was measured in CSF and serum; GM3 (a glycosphingolipid marker known to be elevated in GD patients) was measured in CSF and plasma; and glycoprotein nonmetastatic melanoma protein B (GPNMB; reportedly a biomarker of neuropathic GD3) was measured in CSF. The results are shown in the table below as percent change from baseline at week 4 and week 26 for each parameter:

| | Patient 1 | Patient 2 | Patient 3 | Patient 4 | Patient 5 |
|---|---|---|---|---|---|
| CHITO | | | | | |
| CSF-Week 4 | −5% | +11% | +9% | −6% | −6% |
| CSF-Week 26 | −10% | −11% | +20% | −1% | +68% |
| Serum-Week 4 | −11% | +8% | −7% | −12% | −1% |
| Serum-Week 26 | −43% | −55% | −1% | +98% | −11% |
| GM3 | | | | | |
| CSF-Week 4 | −51% | 0% | −59% | −59% | 0% |
| CSF-Week 26 | −51% | 0% | −59% | −59% | 0% |
| Plasma-Week 4 | −70% | −63% | −65% | −62% | −47% |
| Plasma-Week 26 | −86% | −69% | −74% | −72% | +10% |
| GPNMB | | | | | |
| CSF-Week 4 | −63% | +30% | +9% | −6% | −2% |
| CSF-Week 26 | −14% | 0% | +45% | +10% | −8% |

(B) 52-Week Interim Analysis

A second interim analysis was performed when the first 6 patients had reached 52-weeks of treatment, as described above in section (A). This analysis included Patients 1-5 as described in section (A), as well as new Patient 6. All six patients had L444P (1448T/C) homozygous Gaucher phenotype.

At 52 weeks, all patients remained enrolled in the study. There were a total of 30 treatment-emergent adverse events reported among the six patients, all of which were mild or moderate in severity, and none of which were considered related to treatment with Compound 2 or imiglucerase. The events were primarily headache and back pain, likely related to lumbar puncture.

Analysis of plasma and CSF concentrations of Compound 2 shows largely comparable values to the values obtained at Week 26. Patient 5, however, is found to have about 50% lower concentrations of Compound 2 in plasma and CSF at Week 26, and undetectable concentrations at Week 52. It is believed that this is due to either compliance or dosing errors, and therefore, analysis is repeated without Patient 5's Week 26 and 52 data included. The data supports the conclusion that a steady state concentration of Compound 2 is reached in plasma and CSF at or prior to Week 4:

| Compound 2 in plasma | Day 1 (N = 6) |
|---|---|
| $AUC_{0\_24}$, ng · h/mL (mean ± SD) | 729 ± 205 |
| $C_{max}$, ng/mL (mean ± SD) | 49.1 ± 17.3 |
| $t_{max}$, h (median) | 2.00 |

| Compound 2 in Plasma | Day 1 (N = 6) | Week 4 (N = 6) | Week 26 (N = 6) | Week 52 (N = 6) |
|---|---|---|---|---|
| Concentration 2-4 hours post dose, ng/mL (mean ± SD) | 39.7 ± 12.6 | 92.3 ± 36.4 | 102.0 ± 49.5 | 69.8 ± 58.3 |
| Excluding Patient 5 | | | 112 | 84 |
| **Compound 2 in CSF** | **Day 1 (N = 6)** | **Week 4 (N = 6)** | **Week 26 (N = 6)** | **Week 52 (N = 6)** |
| Concentration 2-4 hours post dose, ng/mL (mean ± SD) | <LLOQ | 4.56 ± 1.20 | 5.26 ± 2.49 | 4.43 ± 3.23 |
| Excluding Patient 5 | | | 6.13 | 5.32 |

At 52 weeks, the data further shows sustained significant improvements in plasma and CSF biomarkers for GD-3. The results are similar to those obtained at 26 weeks. Over all six GD3 patients, plasma and CSF GL-1 and lyso-GL-1 concentrations were as follows:

| | Lyso-GL-1 | | GL-1 | |
|---|---|---|---|---|
| | Baseline | 52-weeks | Baseline | 52-weeks |
| Plasma | 29.3 ng/mL (6.3-159.0) | 15.2 ng/mL (2.5-46.8) | 6.21 μg/mL (4.2-8.3) | 1.59 μg/mL (0.9-2.7) |
| CSF | 34.0 pg/mL (20.1-67.6) | 17.3 pg/mL (5.8-37.4) | 6.36 ng/mL (4.4-11.1) | 2.48 ng/mL (1.0-6.1) |

Thus, at 52-weeks compared to baseline, plasma and CSF concentrations had changed as follows:

| | Lyso-GL-1 (% change) | GL-1 (% change) |
|---|---|---|
| Plasma Concentration | −56.7% | −71.6% |
| CSF Concentration | −55.9% | −55.4% |

In addition, exploratory biomarkers were quantified in CSF of GD3 patients: ceramide (the precursor of GL-1), chitotriosidase (CHITO), GM3, and GPNMB. After 52 weeks of treatment, no significant changes were observed in CSF concentrations of ceramide, CHITO or GPNMB. Four of the six patients had measurable concentrations of GM3 in CSF at baseline, and each of these patients was found to have undetectable GM3 in CSF at 4 weeks, 26 weeks and 52 weeks.

At 52 weeks, quantification of horizontal and vertical saccadic eye movements was performed in all six patients in a similar manner as described in section (A). However, it was determined that the methodology used to account for noise (e.g., caused by blinking or head movements) may have introduced bias into the results. The method of accounting for noise was therefore modified, and a set of control criteria were developed to assess validity of the datasets obtained by the eye movement reader. On reevaluation of the 26-week saccadic eye movement data, and on evaluation of the 52-week data, it was found that the level noise was too high to permit drawing any conclusions from the data.

In addition, at 52 weeks, 5 of 6 patients showed improvements in ataxia. The degree of ataxia at baseline and throughout the study was evaluated by the Scale for Assessment and Rating of Ataxia (SARA; Schmitz-Hubsch et al. [2006]), which assesses eight distinct attributes of cerebellar ataxia on a scale of 0-40. The eight attributes are gait, stance, sitting, speech disturbance, finger chase, nose-finger test, fast alternate hand movement, and heel-shin slide. SARA ataxia scoring results for all six patients is presented in the chart below:

| SARA Cumulative Score | At Screening | Week 26 | Week 52 |
|---|---|---|---|
| Patient 1 | 3.0 | 1.0 | 0.0 |
| Patient 2 | 3.0 | 2.0 | 1.5 |
| Patient 3 | 3.5 | 0.0 | 0.0 |
| Patient 4 | 3.0 | 5.0 | 7.5 |
| Patient 5 | 0.5 | 0.0 | 0.0 |
| Patient 6 | 4.0 | 2.0 | 3.0 |
| Average Score | 2.83 | 1.67 | 2.00 |
| Average Score excluding Patient 4 | 2.80 | 1.00 | 0.90 |

As shown in the table, five of the six patients were mildly ataxic at baseline, with the mean cumulative SARA score being 2.8 (SD=1.2). The most common deficits at baseline were gait disorders. Excluding Patient 5 due to the low level of Compound 2 exposure in this patient and the patient's substantially normal baseline ataxia score (only 0.5), then 4 out of 5 patients exhibited an improvement in ataxia at Week 52 (mean improvement=−0.9; SD=3.2). Patient 4 exhibited an increase in ataxia scoring, with the score at baseline being 3 and at Week 52, 7.5. It should be noted that this apparent deterioration was driven almost entirely by a change in the 'stance' scoring parameter (stance score at baseline and Week 26=1; score at Week 52=5) and that the patient was complaining of left knee pain at the time of the exam. Additionally, the subject had injured his left great toe prior to the exam; this injury was considered resolved 11 days after the exam. Excluding these outlier effect of Patient 4, treatment with Compound 2 resulted in a significantly decreased mean SARA Score by Week 26 which was further slightly improved upon by Week 52.

The trail making test (TMT) was used to evaluate cognitive function in the patients. The TMT is one of the most widely used neuropsychological tests and is included in most test batteries. The TMT is a diagnostic tool to assess general intelligence and cognitive dysfunctions (Tombaugh et al. [2004]; Cavaco et al. [2013]). In part A of the TMT, subjects are asked to connect a cluster of numbers in ascending order. This task is a combination of visual search and general visual and motor processing speed. Part B presents a sequence which alternates between numbers and letters. Subjects must actively switch between both categories when connecting them in ascending, but alternating order. Hence, this task is considered to include an executive function component since the subject must actively switch between categories while connecting the symbols (MacPherson et al. [2017]).

TMT-A evaluates mainly perceptual and psychomotor speed. TMT-B assesses more specifically mental flexibility and shifting abilities. TMT B minus TMT A score is used to remove the variance attributable to the graphomotor and visual scanning components of TMT A. This derived score reflects the unique task requirements of TMT B.

In a study of normative data for TMT A and TMT B in community-dwelling individuals aged 18-89 years (n=911), mean (SD) values in the 18-24 years age group (n=155) were 22.9 s (6.9) for TMT A and 49 s (12.7) for TMT B (Tombauch et al. [2004]). In contrast, the mean times taken to complete Trail A and Trail B for patients in the study were 67.8 s (SD=60.3 s) and 193.8 s (SD=197.0), respectively. At baseline, the mean difference in time taken to complete Trail B minus Trail A was 126.0 s (SD=142.9 s). This shows that the GD-3 patients in this study demonstrated some degree of cognitive dysfunction at baseline.

At Week 52, the mean time taken to complete Trail A was 56.5 s (SD=55.2 s) and Trail B was 122.7 s (SD=91.8 s). Four of six patients exhibited reduction in time taken to complete Trail A and six of six exhibited reduction in time taken to complete Trail B. Excluding Patient 5 due to the low level of Compound 2 exposure in this patient, four of five patients exhibited a TMT-A reduction and five of five patients exhibited a TMT-B reduction.

At Week 52, 5 of 6 patients exhibited a reduction in the (TMT B-TMT A) time. Individual results are shown in the table below.

| TMT-A-TMT-B (s) | At Screening | Week 26 | Week 52 | Change (%) from Baseline to Week 52 |
|---|---|---|---|---|
| Patient 1 | 13 | 21 | 16 | +23% |
| Patient 2 | 71 | 37 | 57 | −20% |
| Patient 3 | 72 | 56 | 20 | −72% |
| Patient 4 | 116 | (no data) | 66 | −43% |
| Patient 5 | 74 | 60 | 72 | −3% |
| Patient 6 | 410 | 440 | 166 | −60% |
| Average | 126 (n = 6) | 123 (n = 5) | 66 (n = 6) | −29% |

At 52 weeks, the mean difference in time taken to complete Trail B minus Trail A was 66.2 s (SD=54.3). Excluding Patient 5, four of five patients exhibited an improvement in Trail B minus Trial A at Week 52, with a mean improvement of −71.4 s (−31.6%) (SD 99.3 s (37.6%)).

Neurological function—was further evaluated using functional magnetic resonance imaging (fMRI). Patient 2 was excluded because no fMRI data was collected at the Week 52 session. Resting-state fMRI screening sessions were performed at baseline screening, Week 26, and Week 52 visits. Connectivity estimates from four subjects (Patients 1, 3, 4 and 5) were entered into second-level analyses as a "compliant" group. Patient 5 was isolated due to likely noncompliance with study medication, as described above. Analyses were performed as described elsewhere (Smith et al. [2009]).

It was found that the compliant subjects demonstrate an enhanced connectivity between a more broadly distributed set of brain regions than the non-compliant subject, with increasing strength between posterior and anterior aspects as the most prominent feature. At the anatomic level, compliant subjects demonstrate a widespread and robust strengthening of connections between occipital-parietal structures and frontal, temporal and limbic targets. Connectivity changes in Patient 5 were more modest and restricted within spatially proximal structures. At the functional level, enhanced connectivity between default mode and medial frontal networks is seen in every subject except Patient 5. This suggests signal within these disparate networks becomes more coherent, such that brain activity can be more efficiently transferred between cognitive reserve (posterior) and higher-order executive functions (anterior). A consistent reciprocal mapping of resting state networks (RSNs) 2 and 3 ("cognition-language-orthography" and "cognition-space") to RSNs 8 and 9 (executive and left frontoparietal) is also evident. The spatial distribution of connectivity changes is much more focal for Patient 5, primarily reflecting overlap between medial-frontal and frontoparietal networks. Both perspectives suggest that patient who fully complied with the treatment protocol developed greater coherence between posterior and anterior aspects of the brain, such that the entire brain becomes amenable to efficient information transfer. Where apparent, altered connectivity for Patient 5 appears within a narrower set of anterior brain regions and represents less holistic evidence of therapeutic benefit.

The results are summarized in the table below. Spatial analysis of the connectivity between different anatomic regions of the brain is performed to define a correlation coefficient for regressed voxelwise mean intensity. The results show that connectivity between the default mode (resting) network and the executive function network increased in Patients 1, 3, 4 and 6, but decreased in Patient 5.

| | Patient 1 | Patient 3 | Patient 4 | Patient 5 | Patient 6 |
|---|---|---|---|---|---|
| Change in Correlation Coefficient | +0.20 | +0.20 | +0.20 | −0.13 | +0.70 |

It was additionally found that two patients experience spleen volume reductions at Week 52, and mean platelet concentration increased by 9.3% on average (range −8.2% to +45.3%), all patients maintaining the therapeutic goal of greater than $120\times10^9$/L platelet count. The increase in mean platelet concentration was primarily driven by increases in 3 of the 6 patients. There were no clinically meaningful changes in hemoglobin levels.

Example 6: Pharmacokinetics of Compound 2 in Healthy Human Volunteers

Two Phase 1 clinical studies were conducted to assess the pharmacokinetics, pharmacodynamics, safety and tolerability of Compound 2 in healthy, human volunteers in the presence and absence of food. Compound 2 is also known as venglustat.

Study 1

Study 1 was a 2-part single-center trial in healthy adult male volunteers. Part 1 was a double-blind, randomized, placebo-controlled sequential ascending single-dose study of Compound 2 for safety, tolerability, and PK. Part 2 was an open-label, single-cohort, randomized, 2-sequence, 2-period, 2-treatment crossover study of Compound 2 for PK with and without a high-fat meal.

Part 1 of the study enrolled and randomized 55 healthy men (placebo, n=14; 2-, 5-, 15, 25-, 50, and 100-mg doses, n=6 each; 150-mg dose, n=5). Eight healthy men participated in Part 2.

In Part 1 the subjects were randomized to receive 2, 5, 15, 25, 50, 100, or 150 mg of Compound 2 (L-malic salt form) or matching placebo on the morning of the first day after at least a 10-hour fast. In Part 2, the subjects were randomized to receive a single oral dose of 5 mg Compound 2 either while fasting (at least 10 hours before and 4 hours after administration) or 30 minutes after a standardized high-fat breakfast (~815 kcal). After a 7-day washout period, participants were crossed over to the other condition.

In Study 1, Part 1, blood was sampled for plasma concentrations of Compound 2 at the time of study drug administration (0 hour) and 0.5, 1, 2, 3, 4, 5, 6, 8, 10, 12, 16, 24, 48, 72, and 96 hours post-dose. Urine samples were collected for analysis of Compound 2 concentrations beginning 2 hours before study drug administration through 48 hours afterward.

In Study 1, Part 2, blood was sampled for plasma concentrations if Compound 2 at 0, 0.5, 1, 2, 3, 4, 5, 6, 8, 10, 12, 16, 24, and 48 hours post-dose.

From Part 1, it was found that following single oral doses of 2 to 150 mg doses of Compound 2, maximal plasma concentration ($C_m$ax) occurred at a median time of 3-5.5 hours before plasma concentrations began to decline exponentially, with a geometric mean $t_{1/2}$ of 28.9 hours. Exposure increased close to dose-proportionally throughout the dose range: a 75-fold dose increase resulted in 97.3-, 89.2-, and 85.9-fold increases in geometric mean $C_{max}$, $AUC_{last}$, and $AUC_{inf}$ values, respectively. PK results are shown in the following table (AUC=area under the time concentration curve, either to last measurable concentration or extrapolated to infinity; $t_{1/2}$=terminal half-life; CL/F=apparent total clearance from plasma; CV=coefficient of variation; SD=standard deviation; $t_{max}$=time to $C_{max}$; Vss/F=apparent volume of distribution at steady state):

| Parameter | 2 mg (N = 6) | 5 mg (N = 6) | 15 mg (N = 6) | 25 mg (N = 6) | 50 mg (N = 6) | 100 mg (N = 6) | 150 mg (N = 5) |
|---|---|---|---|---|---|---|---|
| | | | | $C_{max}$, ng/mL | | | |
| Mean (SD) | 5.7 (1.2) | 14.7 (1.61) | 53.0 (16.7) | 84.4 (31.8) | 181 (56) | 374 (38) | 529 (109) |
| Geometric mean (CV) | 5.6 (21.4) | 14.6 (10.9) | 50.7 (31.5) | 79.9 (37.7) | 173 (31) | 372 (10.3) | 520 (21) |
| $t_{max}$, median h (range) | 3.50 (3.00-8.00) | 5.50 (4.00-8.00) | 3.50 (2.00-5.00) | 5.00 (4.00-8.00) | 4.00 (3.00-6.00) | 3.00 (2.00-4.00) | 4.00 (1.00-8.00) |
| | | | | $AUC_{last}$, ng · h/mL | | | |
| Mean (SD) | 214 (52) | 560 (71) | 1,830 (520) | 3,380 (1100) | 6,310 (1880) | 13,000 (2330) | 18,600 (5480) |
| Geometric mean (CV) | 209 (24.3) | 556 (12.7) | 1,760 (29) | 3,240 (33) | 6,070 (30) | 12,800 (18) | 18,000 (30) |

-continued

| Parameter | 2 mg (N = 6) | 5 mg (N = 6) | 15 mg (N = 6) | 25 mg (N = 6) | 50 mg (N = 6) | 100 mg (N = 6) | 150 mg (N = 5) |
|---|---|---|---|---|---|---|---|
| $AUC_{inf}$, ng · h/mL | | | | | | | |
| Mean (SD) | 243 (61) | 652 (122) | 2,070 (600) | 3,810 (1,080) | 7,130 (2,320) | 14,400 (3,010) | 20,600 (6,640) |
| Geometric mean (CV) | 237 (25) | 643 (19) | 1,990 (29) | 3,690 (28) | 6,800 (33) | 14,100 (21) | 19,900 (32) |
| $t_{1/2}$, h | | | | | | | |
| Mean (SD) | 29.2 (43) | 33.3 (8.1) | 29.7 (7.1) | 30.2 (5.5) | 28.9 (5.3) | 27.8 (3.6) | 26.9 (5.7) |
| Geometric mean (CV) | 28.9 (14.8) | 32.5 (24.4) | 29.0 (24.0) | 29.8 (18.1) | 28.5 (18.4) | 27.6 (12.8) | 26.4 (21.3) |
| CL/F, L/h | | | | | | | |
| Mean (SD) | 6.43 (1.41) | 5.86 (1.01) | 5.85 (1.89) | 5.18 (1.31) | 5.75 (2.01) | 5.38 (1.25) | 5.80 (1.55) |
| Geometric mean (CV) | 6.3 (22.0) | 5.8 (17.3) | 5.6 (32.2) | 5.0 (25.3) | 5.5 (34.9) | 5.3 (23.4) | 5.6 (26.7) |
| $V_{ss}$/F, L | | | | | | | |
| Mean (SD) | 275 (54) | 274 (30) | 245 (81) | 240 (78) | 239 (62) | 213 (22) | 228 (50) |
| Geometric mean (CV) | 270 (20) | 273 (11) | 233 (33) | 228 (33) | 232 (26) | 212 (10) | 223 (22) |

From Part 2, it was found that administration of a 5 mg dose with a high-fat meal had no effect on Compound 2 exposure compared with fasting conditions. Median $t_{max}$ was 6.00 hours whether fed or fasting. Fed/fasted geometric mean ratios were 0.92 and 0.91 for $C_m$ax and $AUC_{last}$, respectively. Within-subject variability (i.e., fed vs fasted) accounted for less than half the total subject variability.

Study 2

Study 2 was a single-center, double-blind, randomized, placebo-controlled, sequential ascending repeated-dose study of the safety, tolerability, PK, and pharmacodynamics of Compound 2 in healthy adult male and female volunteers.

The study enrolled and randomized 36 healthy adults (19 men and 17 women) (n=9 each to group). The subjects were randomized to receive once-daily doses of Compound 2 at 5, 10, or 20 mg (provided as 5-mg capsules of the L-malic salt form) or placebo for 14 days after at least a 10-hour fast.

Blood was sampled for plasma concentrations of Compound 2 as follows: Day 1 at 0, 0.5, 1, 2, 3, 4, 5, 6, 8, 10, 12, and 16 hours post-dose; On Days 2-5, 8, 11, and 13, at 0 h; On Day 14, at 0.5, 1, 2, 3, 4, 5, 6, 8, 10, 12 hours post-dose; On Days 15-17, at 24, 48, and 72 hours, respectively, after the Day 14 dose. Urine samples were collected for analysis of Compound 2 concentrations on Day 1 (0 hours post-dose) and continuously on Day 14 from 0-24 hours post-dose. Pharmacodynamic endpoints (plasma GL-1, GL-3, and GM3 concentrations) were assessed on Days 1-5, 8, 11, 13, and 14, at 0 hours post-dose; and on Day 15, at 24 hours after the Day 14 dose.

It was found that in subjects receiving 5, 10, or 20 mg of Compound 2 once daily for 14 days, plasma $C_{max}$ occurred at a median time of 2-5 hours post-dose on Days 1 and 14. $C_{trough}$ values reached a plateau after Day 5. Compound 2 exposure increased close to dose-proportionally over the dose range of 5-20 mg: this 4-fold dose increase resulted in 3.76- and 3.69-fold increases in geometric mean $C_m$ax and $AUC_{0-24}$ values on Day 14, respectively. PK results from Study 2 are summarized in the following table:

| Parameter | 5 mg (N = 9) | 10 mg (N = 9) | 20 mg (N = 9) |
|---|---|---|---|
| Day 1 | | | |
| $C_{max}$, ng/mL | | | |
| Mean (SD) | 18.5 (3.2) | 38.5 (7.4) | 68.0 (15.7) |
| Geometric mean (CV) | 18.2 (17.3) | 37.8 (19.3) | 66.5 (23.1) |
| $t_{max}$, median h (range) | 5.00 (2.00-8.17) | 3.00 (2.00-5.00) | 3.07 (2.00-6.00) |
| $AUC_{0-24}$, ng · h/mL | | | |
| Mean (SD) | 296 (54) | 635 (132) | 1,100 (211) |
| Geometric mean (CV) | 292 (18) | 623 (21) | 1,080 (19) |
| Day 14 | | | |
| $C_{max}$, ng/mL | | | |
| Mean (SD) | 37.0 (6.4) | 89.7 (29.1) | 142 (40) |
| Geometric mean (CV) | 36.5 (17.2) | 86.0 (32.5) | 137 (28.3) |
| $t_{max}$, median h (range) | 3.00 (2.00-6.00) | 2.00 (2.00-6.00) | 3.00 (2.00-8.00) |
| $AUC_{0-24}$, ng · h/mL | | | |
| Mean (SD) | 642 (121) | 1,550 (464) | 2,420 (705) |
| Geometric mean (CV) | 632 (19) | 1,490 (30) | 2,340 (29) |
| $C_{trough}$, ng/mL | | | |
| Mean (SD) | 19.4 (4.0) | 49.9 (19.3) | 73.3 (24.4) |
| Geometric mean (CV) | 19.0 (20.5) | 47.5 (38.7) | 69.9 (33.2) |
| $t_{1/2}$, h | | | |
| Mean (SD) | 29.3 (4.6) | 31.3 (3.3) | 35.0 (6.3) |
| Geometric mean (CV) | 29.0 (15.8) | 31.2 (10.5) | 34.5 (18.0) |
| CLss/F, L/h | | | |
| Mean (SD) | 5.98 (1.17) | 5.13 (1.25) | 6.58 (1.70) |
| Geometric mean (CV) | 5.9 (19.5) | 5.0 (24.4) | 6.4 (25.8) |
| $CL_{R\ (0-24)}$, L/h | | | |
| Mean (SD) | 1.55 (0.68) | 1.49 (0.41) | 2.07 (0.58) |
| Geometric mean (CV) | NA[a] (44.0) | 1.4 (27.7) | 2.0 (28.0) |

After 14 once-daily doses of Compound 2, its 24-hour unchanged urinary excretion fraction (mean $fe_{0-24}$) ranged between 26.3% and 33.1% without any obvious dose-relatedness. Mean CLR(a24) ranged between 1.49/h and 2.07/h, approximately 3.18-3.86-fold lower than observed plasma CL/F.

Plasma GL-1, GL-3, and GM3 in placebo recipients remained similar to baseline throughout, whereas plasma GL-1 and GM3 levels decreased from baseline time- and dose-dependently across the 3 Compound 2 dose groups, as shown in the following table (Point estimates of treatment ratios for glucosylceramide (GL-1), globotriaosylceramide (GL-3), and GM3 ganglioside (GM3) on Day 15 in the repeated ascending dose study):

| Parameter | Comparison | Estimate | 90% Confidence Interval |
|---|---|---|---|
| GL-1 | 5 mg vs placebo | 0.39 | 0.29-0.50 |
| | 10 mg vs placebo | 0.32 | 0.25-0.42 |
| | 20 mg vs placebo | 0.23 | 0.17-0.30 |
| GL-3 | 5 mg vs placebo | 0.61 | 0.47-0.79 |
| | 10 mg vs placebo | 0.69 | 0.53-0.89 |
| | 20 mg vs placebo | 0.67 | 0.51-0.89 |
| GM3 | 5 mg vs placebo | 0.56 | 0.45-0.70 |
| | 10 mg vs placebo | 0.49 | 0.39-0.60 |
| | 20 mg vs placebo | 0.40 | 0.32-0.50 |

Maximal sustained effects on GL-1 occurred on Day 11 in the 5- and 10-mg groups and by Day 8 in the 20-mg group. Mean calculated GL-1 reductions from baseline at Day 15 were 41.9%, 69.6%, and 74.6% in the respective 5-, 10- and 20-mg groups. GL-1 values were below the lower limit quantification (LLOQ) at baseline in 1 5-mg Compound 2 recipient and at Day 15 in 3, 5, and 9 subjects in the 5-, 10-, and 20-mg groups, respectively.

Maximal sustained GM3 decreases occurred across all Compound 2 dose groups starting on Day 13. Mean Day 15 plasma GM3 levels were 42.7%, 49.4%, and 57.8% of baseline for the 5-, 10-, and 20-mg dose groups, respectively. GM3 was below the LLOQ at Day 15 in 1 and 2 subjects in the 10- and 20-mg dose groups, respectively.

Plasma GL-3 also decreased with time in all Compound 2 dose groups, but variable and low baseline GL-3 values relative to LLOQ limited mean calculated GL-3 reductions. In the placebo, 5-, 10-, and 20-mg dose groups, GL-3 values were below LLOQ in 1, 3, 1, and 6 subjects, respectively, at baseline and in 4, 9, 7, and 9 subjects, respectively, at Day 15.

Mean estimated plasma GL-1 reductions from baseline (90% CI) attributable to Compound 2 $C_{trough}$ in the 5, 10, and 20 mg dose groups (19.0, 47.5, and 69.9 ng/mL, respectively) were 67.0% (54.4-79.7%), 74.4% (63.7-85.2%), and 76.3% (64.8-87.8%), respectively.

CONCLUSIONS

In these studies, Compound 2 exposure in healthy subjects ($C_{max}$ and AUC) was close-to-dose-proportional when administered as single doses ranging from 2-150 mg or as repeated, once-daily doses ranging from 5-20 mg for 14 days. Compared with fasting, a high-fat meal had no effect on exposure in subjects who received a single 5-mg dose. With repeated once-daily doses from 5-20 mg, steady state was achieved within 5 days; neither age nor gender affected accumulation. Pharmacodynamically, repeated once-daily doses of Compound 2 reduced plasma concentrations of GL-1 and GM3 in a time- and dose-dependent manner, consistent with Compound 2-mediated GCS inhibition, although baseline levels of GL-3 were too low to be useful as a pharmacodynamic biomarker. The dose-dependent GL-1 reduction corroborated the intended mechanism of action of Compound 2: inhibition of GL-1 formation from ceramide by GCS.

In all studies, safety profile was assessed by monitoring treatment-emergent adverse events (TEAEs) through 10 days after last dose of study medication, including serious adverse events [SAEs]), ECG monitoring, laboratory values, and physical examinations. There were no deaths, SAEs, severe TEAEs, or TEAEs leading to study discontinuation in any of the studies.

No clinically relevant hematologic or biochemical abnormalities were reported in any of the studies. Vital signs showed no relevant changes from baseline in any of the studies. ECG parameters showed no relevant changes in the single ascending dose and food effect studies; in the multiple ascending dose study no ECG parameters changed statistically significantly from average baseline versus placebo in recipients of Compound 2 at any dose. It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Example 7: Clinical Study of Compound 2 in Fabry Disease Patients

Method

A three-year open-label investigation of Compound 2 in young classic Fabry disease patients was conducted in order to evaluate the long-term safety, pharmacodynamics and exploratory efficacy of Compound 2 in adult male Fabry patients. Eleven subjects enrolled in the study, and seven subjects completed all aspects of the study. All subjects were males diagnosed with classic Fabry disease confirmed by genotype and residual alpha-galactosidase activity below detection levels (9 of the 11 had nonsense mutation in the GLA gene). All subjects had lyso-GL3 levels in plasma of at least 65 ng/mL and had no prior Fabry disease-specific treatment. The median age of subject was 24 years (range 19-37).

Patients were administered a daily oral dose of 15 mg of Compound 2. The clearance of GL-3 deposits in the skin was monitored by taking biopsies at weeks 12, 26, 52 and 156, which were evaluated semi-quantitatively by light microscopy (focusing on skin capillary endothelial cells). Each sample was scored independently by 3 pathologists for the presence of GL-3 inclusions on a four-point scale, and rated as 0 (no/trace), 1 (mild), 2 (moderate), or 3 (severe) according to Eng et al., N. Engl. J. Med. 345:9-16 (2001). A single score per patient per time point was derived by taking the score rated by the majority of the three pathologists. If a majority score could not be derived, then the median score was used (resulting in some fractional scores). Plasma samples were also analyzed for GL-3, lyso-GL-3, GL-1 and GM3 at baseline and weeks 12, 26, 52 and 156. Pain scores and abdominal symptoms were analyzed at baseline and weeks 12, 26, 52, 104 and 156 using the SF-36 scoring protocol.

Patients were assessed using the Short Form-36 (SF-36) questionnaire on numerous visits from baseline to week 156. This is a 36-item questionnaire used to measure 8 various aspects of health (vitality, physical functioning, bodily pain, general health perceptions, physical role functioning, emotional role functioning, social role functioning and mental health). The score for each of the eight aspects ranges from 0 (maximum disability) to 100 (no disability), and thus, higher scores indicate good health condition. In addition, gastrointestinal symptoms, including abdominal pain, abdominal distention, and bowel movements, were assessed using a modified version of the inflammatory bowel severity scoring system. Particular questions asked as part of these assessments included: (1) whether the patient suffered abdominal pain within the last ten days, (2) what was the severity of abdominal pain suffered in the last ten days using a 0 (no pain) to 100 (very severe pain) scale, and (3) on how many days within the last ten days did the patient have abdominal pain.

Results

By week 156, five patients showed a 1-point reduction in skin GL-3 score, two patients had complete clearance of GL-3 inclusions, one patient had no change, and one patient lacked samples. Over the course of the 156-week study, mean plasma GL-1 levels dropped by 69%, mean plasma GM3 levels dropped by 60%, mean plasma GL-3 levels dropped by 77%, and mean plasma lyso-GL3 levels dropped by 52%. Plasma GL-1 and GM3 showed a very rapid drop within the first 2-4 weeks of treatment. All four measures showed a sustained maintenance of reduced plasma load which was largely stabilized by week 52.

Plasma and urine data are summarized in the table below:

| | Change from baseline measurement at: | | | |
|---|---|---|---|---|
| Parameter Measured: | 26 weeks (n = 9) | 52 weeks (n = 7) | 104 weeks (n = 7) | 156 weeks (n = 7) |
| Plasma GL-3 (μg/mL) | −3.62 μg/mL | −5.06 μg/mL | −6.32 μg/mL | −6.97 μg/mL |
| Plasma lyso-GL-3 (ng/mL) | −30.99 ng/mL | −37.10 ng/mL | −39.84 ng/mL | −48.13 ng/mL |
| Plasma GL-1 (μg/mL) | −3.26 μg/mL | −3.58 μg/mL | −3.70 μg/mL | −3.23 μg/mL |
| Plasma GM3 (μg/mL) | −10.77 μg/mL | −8.84 μg/mL | −9.92 μg/mL | −8.12 μg/mL |
| Urine GL-3 (mg per urine creatinine) | −0.25 mg/mmol (n = 8) | −0.20 mg/mmol (n = 7) | −0.18 mg/mmol (n = 7) | −0.18 mg/mmol (n = 7) |

These results demonstrate that the Compound 2 administered at 15 mg/day consistently reduces the levels of GL-1, lyso-GL-1 and GM3 in the body in a generally progressive manner.

In addition, data from a previously completed placebo-controlled phase 3 trial of agalsidase beta (Fabrazyme) was analyzed for comparison (see Eng et al., N. Eng. J. Med., 345:9 (2001). For comparison to agalsidase beta, the historical control arm was patients treated with agalsidase beta in the phase 3 trial, and change in plasma GL-3 was compared at multiple time points up to three years. Entry criteria and baseline characteristics were similar between the two studies. To strengthen the comparison, patients receiving Compound 2 were matched with phase 3 study patients based on propensity scores using baseline variables of age, plasma GL-3, gender, UPCR (<500 mg/g versus 500-1000 mg/g versus >1000 mg/g), and eGFR (<80 versus ≥80 mL/min/1.73 $m^2$). 11 patients receiving Compound 2 were matched to 19 patients for the placebo comparison and to 28 patients for the agalsidase beta comparison. All patients in all three groups were male and demonstrated elevated plasma GL-3, UPCR of <500 mg/g, and eGFR >80 mL/min/1.73 $m^2$. Mean ages were similar across the three groups. The comparison shows that treatment with Compound 2 for 26 weeks led to a significant reduction in plasma GL-3 compared to placebo, −3.62 μg/mL versus −1.06 μg/mL (P<0.0001). While treatment with Compound 2 yielded a similar reduction in plasma GL-3 at 52 weeks compared to agalsidase beta, at 104 weeks and at 156 weeks, the plasma GL-3 reduction from Compound treatment was significantly greater (p=0.0351 at 104 weeks; p=0.0081 at 156 weeks). Plasma GL-3 levels after 156 weeks were 1.90 μg/mL for patients treated with Compound 2, compared to 4.44 μg/mL for patients treated with agalsidase beta.

Detailed results for the skin GL-3 inclusion scores are shown in the tables below (score of 0 indicates no GL-3 inclusions):

| Endothelial Cells, Superficial Vessels | | | | |
|---|---|---|---|---|
| Skin GL-3 Score | Number of Patients in Each Change Category (changes compared to baseline skin score) at: | | | |
| Change | 12 weeks | 26 weeks | 52 weeks | 156 weeks |
| Score 1 dropped to 0 | | | | 2/6 (33%) |
| Score 1 unchanged | 4/9 (44%) | 4/9 (44%) | 3/6 (50%) | 1/6 (17%) |
| Score 1 raised to 2 | 1/9 (11%) | 1/9 (11%) | | |
| Score 2 dropped to 1 | 3/9 (33%) | 3/9 (33%) | 2/6 (33%) | 3/6 (50%) |
| Score 2 unchanged | 1/9 (11%) | 1/9 (11%) | 1/6 (17%) | |

| Endothelial Cells, Deep Vessels | | | | |
|---|---|---|---|---|
| Skin GL-3 Score | Number of Patients in Each Change Category (changes compared to baseline skin score) at: | | | |
| Change | 12 weeks | 26 weeks | 52 weeks | 156 weeks |
| Score 1 unchanged | 1/9 (11%) | 1/9 ( 11%) | | 1/6 (17%) |
| Score 2 dropped to 0.5 | | | | 1/6 (17%) |
| Score 2 dropped to 1 | 2/9 (22%) | 2/9 (22%) | 3/6 (50%) | 3/6 (50%) |
| Score 2 dropped to 1.5 | | | 1/6 (17%) | |
| Score 2 unchanged | 6/9 (67%) | 6/9 (67%) | 2/6 (33%) | 1/6 (17%) |

| Smooth Muscle Cells, Deep Vessels | | | | |
|---|---|---|---|---|
| Skin GL-3 Score | Number of Patients in Each Change Category (changes compared to baseline skin score) at: | | | |
| Change | 12 weeks | 26 weeks | 52 weeks | 156 weeks |
| Score 1.5 unchanged | | 2/9 (22%) | | |
| Score 1.5 raised to 2 | 2/9 (22%) | | 1/5 (20%) | 1/6 (17%) |
| Score 2 dropped to 0.5 | | | | |
| Score 2 dropped to 1 | | | | 1/6 (17%) |
| Score 2 dropped to 1.5 | | | | 1/6 (17%) |
| Score 2 unchanged | 7/9 (78%) | 7/9 (78%) | 4/5 (80%) | 3/6 (50%) |

| Perineurium Cells | | | | |
|---|---|---|---|---|
| Skin GL-3 Score | Number of Patients in Each Change Category (changes compared to baseline skin score) at: | | | |
| Change | 12 weeks | 26 weeks | 52 weeks | 156 weeks |
| Score 1 unchanged | | | | 1/6 (17%) |
| Score 1 raised to 2 | 1/9 (11%) | 1/9 (11%) | 1/6 (17%) | |
| Score 2 dropped to 1 | | | 1/6 (17%) | |
| Score 2 dropped to 1.5 | | | 1/6 (17%) | 1/6 (17%) |
| Score 2 unchanged | 8/9 (89%) | 8/9 (89%) | 3/6 (50%) | 4/6 (67%) |

In addition to scoring GL-3 skin inclusions by light microscopy, the fraction of the volume of endothelial cell cytoplasm occupied by GL-3 inclusions was estimated using point-counting of electron microscopic images by a masked reader. Images from at least 50 superficial endothelial cell capillaries were obtained using electron microscopy at 7500× magnification. Two-sided t tests were used to evaluate differences between baseline and post-treatment values at each time point. The results are shown in the table below:

| | Baseline (N = 9) | 3 months (N = 9) | 6 months (N = 8) | 3 years (N = 6) |
|---|---|---|---|---|
| Volume fraction (volume of inclusions/total cytoplasmic volume) | 0.29 ± 0.03 | 0.29 ± 0.06 | 0.23 ± 0.04 | 0.18 ± 0.03 |
| Change from baseline | | −1.9% | −21.1% | −38.7% |
| P value vs. baseline | | 0.74 | 0.001 | 0.001 |

These results demonstrate that the Compound 2 administered at 15 mg/day consistently reduces the levels of GL-3 inclusions in the skin in a generally progressive manner. Results were generally more pronounced for superficial vessel endothelial compared to deep vessel endothelial cells and other skin tissues.

Seven of nine patients had improved overall bodily pain scores at week 26 (SF-36), while three of six patients had improved overall bodily pain scores at week 156 (SF-36). Among the patients with gastrointestinal pain at baseline, the severity of the pain (abdominal pain) decreased in four out of five at week 26, and in four out of four at week 156. The number of 10 days with gastrointestinal pain was reduced in five of five patients at week 26 and in three of four patients at week 156.

Detailed results for abdominal pain measures are shown in the tables below.

| Abdominal Pain | | | | | | |
|---|---|---|---|---|---|---|
| Number of Patients Reporting "Yes" to Abdominal Pain in 10-Days Preceding Visit | | | | | | |
| Baseline | 4 weeks | 12 weeks | 26 weeks | 52 weeks | 104 weeks | 156 weeks |
| 6/11 (55%) | 4/11 (36%) | 2/10 (20%) | 3/9 (33%) | 2/7 (28%) | 2/7 (28%) | 2/7 (28%) |
| Abdominal Pain Severity Score in 10-Days Preceding Visit (mean value, 0-100 scale) | | | | | | |
| Baseline (n = 6) | 4 weeks (n = 4) | 12 weeks (n = 2) | 26 weeks (n = 3) | 52 weeks (n = 1) | 104 weeks (n = 1) | 156 weeks (n = 2) |
| 52.50 | 29.75 | 40.00 | 31.33 | 21.00 | 21.00 | 15.00 |
| Number of Days within Preceding 10 Days with Abdominal Pain (mean value) | | | | | | |
| Baseline (n = 6) | 4 weeks (n = 4) | 12 weeks (n = 2) | 26 weeks (n = 3) | 52 weeks (n = 3) | 104 weeks (n = 2) | 156 weeks (n = 2) |
| 3.83 | 2.50 | 3.50 | 3.00 | 0.70 | 0.50 | 0.20 |

These results demonstrate that the Compound 2 administered at 15 mg/day consistently reduces abdominal pain and discomfort in the body in a generally progressive manner.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed:

1. A method for treating pain associated with Fabry disease, comprising: administering to a human subject in need thereof an effective amount of a compound of formula (I), (I)

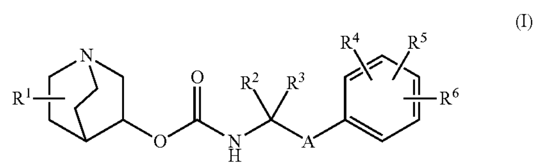

or a pharmaceutically acceptable salt or prodrug thereof, wherein:

$R^1$ is selected from hydrogen, halogen, cyano, nitro, hydroxy, thio, amino, $C_{1-6}$-alkyl, $C_{2-6}$-alkenyl, $C_{2-6}$-alkynyl, $C_{1-6}$-alkyloxy, $C_{2-6}$-alkenyloxy, and $C_{2-6}$-alkynyloxy;

$R^2$ and $R^3$ are independently selected from $C_{1-3}$-alkyl, or $R^2$ and $R^3$ together form a cyclopropyl or cyclobutyl group;

$R^4$, $R^5$ and $R^6$ are each independently selected from hydrogen, halogen, nitro, hydroxy, thio, amino, $C_{1-6}$-alkyl, and $C_{1-6}$-alkyloxy; and A is a 5- or 6-membered aryl or heteroaryl group.

2. The method of claim 1, wherein $R^2$ and $R^3$ are each independently selected from $C_{1-2}$-alkyl.

3. The method of claim 1, wherein $R^4$ is selected from a halogen, $C_{1-3}$-alkyl, and $C_{1-3}$-alkyloxy.

4. The method of claim 1, wherein $R^4$ is fluorine or 2-methoxyethoxy, and $R^5$ and $R^6$ are hydrogen.

5. The method of claim 1, wherein A is chosen from phenyl and a 5-membered heteroaryl group comprising 1 or 2 heteroatoms selected from N and S.

6. The method of claim 1, wherein said compound is a compound of formula (II), (III), (IV), (V), (VI), (VII), (VIII), (IX) or (XI), (II)

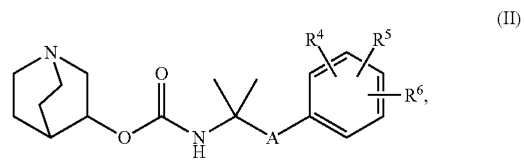

(III)

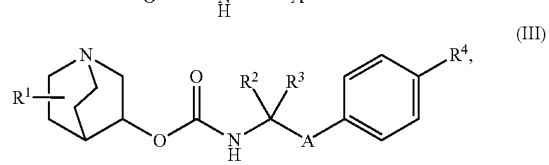

-continued (IV)

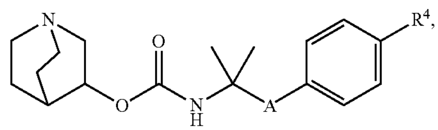

(V)

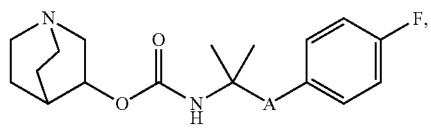

(VI)

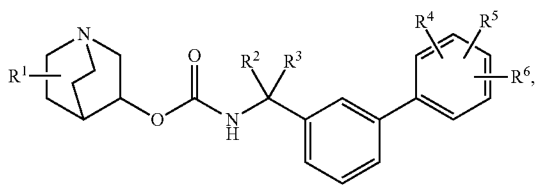

(VII)

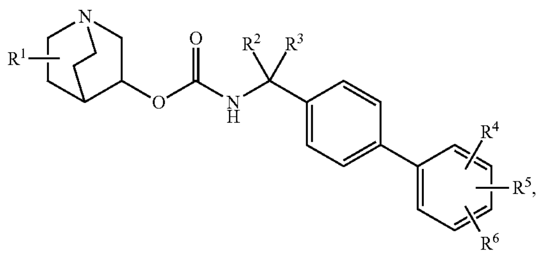

(VIII)

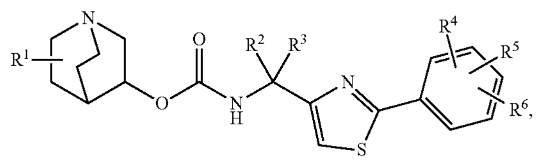

(IX)

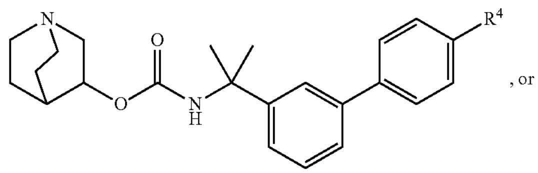

, or

-continued (XI)

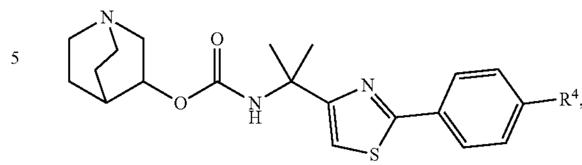

or a pharmaceutically acceptable salt or prodrug thereof.

7. The method of claim 1, wherein said compound is selected from: quinuclidin-3-yl (2-(4'-fluoro-[1,1'-biphenyl]-3-yl) propan-2-yl) carbamate; (S)-quinuclidin-3-yl (2-(2-(4-fluorophenyl) thiazol-4-yl) propan-2-yl) carbamate; (S)-quinuclidin-3-yl (2-(4'-(2-methoxyethoxy)-[1,1'-biphenyl]-4-yl) propan-2-yl) carbamate; and the pharmaceutically acceptable salts and prodrugs thereof; and (S)-quinuclidin-3-yl (2-(2-(4-fluorophenyl) thiazol-4-yl) propan-2-yl) carbamate in malate salt form.

8. The method of claim 1, wherein the pain is selected from the group consisting of neuropathic pain, gastrointestinal pain, and peripheral neuropathy.

9. The method of claim 1, wherein the method comprises administering the compound of formula (I) by systemic administration.

10. The method of claim 1, wherein the method comprises administering the compound of formula (I) in a single daily dose of 5 mg, 10 mg, 15 mg, or 20 mg.

11. The method of claim 1, wherein the pain is abdominal pain.

12. The method of claim 1, wherein the method comprises administering the compound of formula (I) in a daily dose of about 1 mg to about 150 mg of the compound.

13. The method of claim 1, wherein the method comprises administering the compound of formula (I) by systemic administration in a daily dose of about 1 mg to about 150 mg of the compound.

14. The method of claim 1, wherein the compound of formula (I) is (S)-quinuclidin-3-yl (2-(2-(4-fluorophenyl) thiazol-4-yl) propan-2-yl) carbamate or a pharmaceutically acceptable salt thereof.

15. The method of claim 14, wherein the method comprises administering (S)-quinuclidin-3-yl (2-(2-(4-fluorophenyl) thiazol-4-yl) propan-2-yl) carbamate in a single daily dose of 15 mg, or an equivalent amount of a pharmaceutically acceptable salt thereof.

16. The method of claim 8, wherein the compound of formula (I) is(S)-quinuclidin-3-yl (2-(2-(4-fluorophenyl)thiazol-4-yl) propan-2-yl)carbamate or a pharmaceutically acceptable salt thereof.

17. The method of claim 9, wherein the compound of formula (I) is(S)-quinuclidin-3-yl (2-(2-(4-fluorophenyl)thiazol-4-yl) propan-2-yl)carbamate or a pharmaceutically acceptable salt thereof.

18. The method of claim 10, wherein the compound of formula (I) is(S)-quinuclidin-3-yl (2-(2-(4-fluorophenyl)thiazol-4-yl) propan-2-yl)carbamate or a pharmaceutically acceptable salt thereof.

19. The method of claim 11, wherein the compound of formula (I) is(S)-quinuclidin-3-yl (2-(2-(4-fluorophenyl)thiazol-4-yl) propan-2-yl)carbamate or a pharmaceutically acceptable salt thereof.

* * * * *